US010940199B2

(12) United States Patent
Asimakopoulos et al.

(10) Patent No.: US 10,940,199 B2
(45) Date of Patent: Mar. 9, 2021

(54) VERSIKINE FOR INDUCING AND POTENTIATING AN IMMUNE RESPONSE

(71) Applicant: Wisconsin Alumni Research Foundation, Madison, WI (US)

(72) Inventors: Fotios Asimakopoulos, Madison, WI (US); Chelsea Hope, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 7 days.

(21) Appl. No.: 15/454,496

(22) Filed: Mar. 9, 2017

(65) Prior Publication Data
US 2017/0258898 A1    Sep. 14, 2017

Related U.S. Application Data

(60) Provisional application No. 62/437,418, filed on Dec. 21, 2016, provisional application No. 62/343,414, filed on May 31, 2016, provisional application No. 62/305,761, filed on Mar. 9, 2016.

(51) Int. Cl.
*A61K 39/39* (2006.01)
*C07K 14/47* (2006.01)
*A61K 39/00* (2006.01)

(52) U.S. Cl.
CPC .......... *A61K 39/39* (2013.01); *C07K 14/4725* (2013.01); *A61K 2039/55516* (2013.01); *A61K 2039/572* (2013.01); *C07K 2319/00* (2013.01)

(58) Field of Classification Search
None
See application file for complete search history.

(56) References Cited

U.S. PATENT DOCUMENTS

| 2004/0213762 | A1* | 10/2004 | Wight | ................ | C07K 14/4725 424/93.2 |
| 2006/0239965 | A1* | 10/2006 | Szoka, Jr. | ............... | A61K 38/19 424/85.1 |
| 2011/0008366 | A1* | 1/2011 | Wight | ................ | A61K 31/7105 424/172.1 |

FOREIGN PATENT DOCUMENTS

EP    2078728 A1 *  7/2009    ......... C07K 14/4725

OTHER PUBLICATIONS

Arana P, Zabaleta A, Lasa M, Maiso P, Alignani D, Jelinek T, et al. High-Throughput Characterization and New Insight into the Role of Tumor Associated Macrophages (TAMs) in Multiple Myeloma (MM). Blood 2016;128(22):482-82.
Brasel K, De Smedt T, Smith JL, Maliszewski CR. Generation of murine dendritic cells from flt3-ligand-supplemented bone marrow cultures. Blood 2000;96(9):3029-39.
Broz ML, Binnewies M, Boldajipour B, Nelson AE, Pollack JL, Erle DJ, et al. Dissecting the tumor myeloid compartment reveals rare activating antigen-presenting cells critical for T cell immunity. Cancer Cell 2014;26(5):638-52.
Bupathi M, Wu C. Biomarkers for immune therapy in colorectal cancer: mismatch-repair deficiency and others. J Gastrointest Oncol 2016;7(5):713-20.
Coombes JL, Powrie F. Dendritic cells in intestinal immune regulation. Nat Rev Immunol 2008;8(6):435-46.
Cross NA, Chandrasekharan S, Jokonya N, Fowles A, Hamdy FC, Buttle DJ, et al. The expression and regulation of ADAMTS-1, -4, -5, -9, and -15, and TIMP-3 by TGFbetal in prostate cells: relevance to the accumulation of versican. Prostate 2005;63(3):269-75.
Du WW, Yang W, Yee AJ. Roles of versican in cancer biology—tumorigenesis, progression and metastasis. Histol Histopathol 2013;28(6):701-13.
Foulcer SJ, Day AJ, Apte SS. Isolation and purification of versican and analysis of versican proteolysis. Methods Mol Biol 2015;1229:587-604.
Galon J, Costes A, Sanchez-Cabo F, Kirilovsky A, Mlecnik B, Lagorce-Pages C, et al. Type, density, and location of immune cells within human colorectal tumors predict clinical outcome. Science 2006;313(5795):1960-4.
Gao D, Joshi N, Choi H, Ryu S, Hahn M, Catena R, et al. Myeloid progenitor cells in the premetastatic lung promote metastases by inducing mesenchymal to epithelial transition. Cancer Res 2012;72(6)1384-94.
Goldszmid RS, Dzutsev A, Viaud S, Zitvogel L, Restifo NP, Trinchieri G. Microbiota modulation of myeloid cells in cancer therapy. Cancer Immunol Res 2015;3(2):103-9.
Hope C, Foulcer S, Jagodinsky J, Chen SX, Jensen JL, Patel S, et al. Immunoregulatory roles of versican proteolysis in the myeloma microenvironment. Blood 2016;128(5):680-5.
Hope C, Ollar SJ, Heninger E, Hebron E, Jensen JL, Kim J, et al. TPL2 kinase regulates the inflammatory milieu of the myeloma niche. Blood 2014;123(21):3305-15.
Kim S, Takahashi H, Lin WW, Descargues P, Grivennikov S, Kim Y, et al. Carcinoma-produced factors activate myeloid cells through TLR2 to stimulate metastasis. Nature 2009;457(7225):102-6.
Lind GE, Kleivi K, Meling GI, Teixeira MR, Thiis-Evensen E, Rognum TO, et al. ADAMTS1, CRABP1, and NR3C1 identified as epigenetically deregulated genes in colorectal tumorigenesis. Cell Oncol 2006;28(5-6):259-72.
Lynch D, Murphy A. The emerging role of immunotherapy in colorectal cancer. Ann Trans Med 2016;4(16):305.

(Continued)

*Primary Examiner* — Amy E Juedes
(74) *Attorney, Agent, or Firm* — Quarles & Brady LLP

(57) ABSTRACT

Disclosed are methods, kits, polypeptides, and pharmaceutical compositions for inducing an immune response in a subject, which may include a T-cell mediated immune response. The methods comprise administering to the subject, or to explanted cells of the subject, a pharmaceutical composition comprising an effective amount of versikine or a variant of versikine that induces the T-cell mediated immune response. The methods, kits, polypeptides, and pharmaceutical compositions may be used, in particular, to treat a subject having a cell proliferative disease or disorder.

Figure 1:
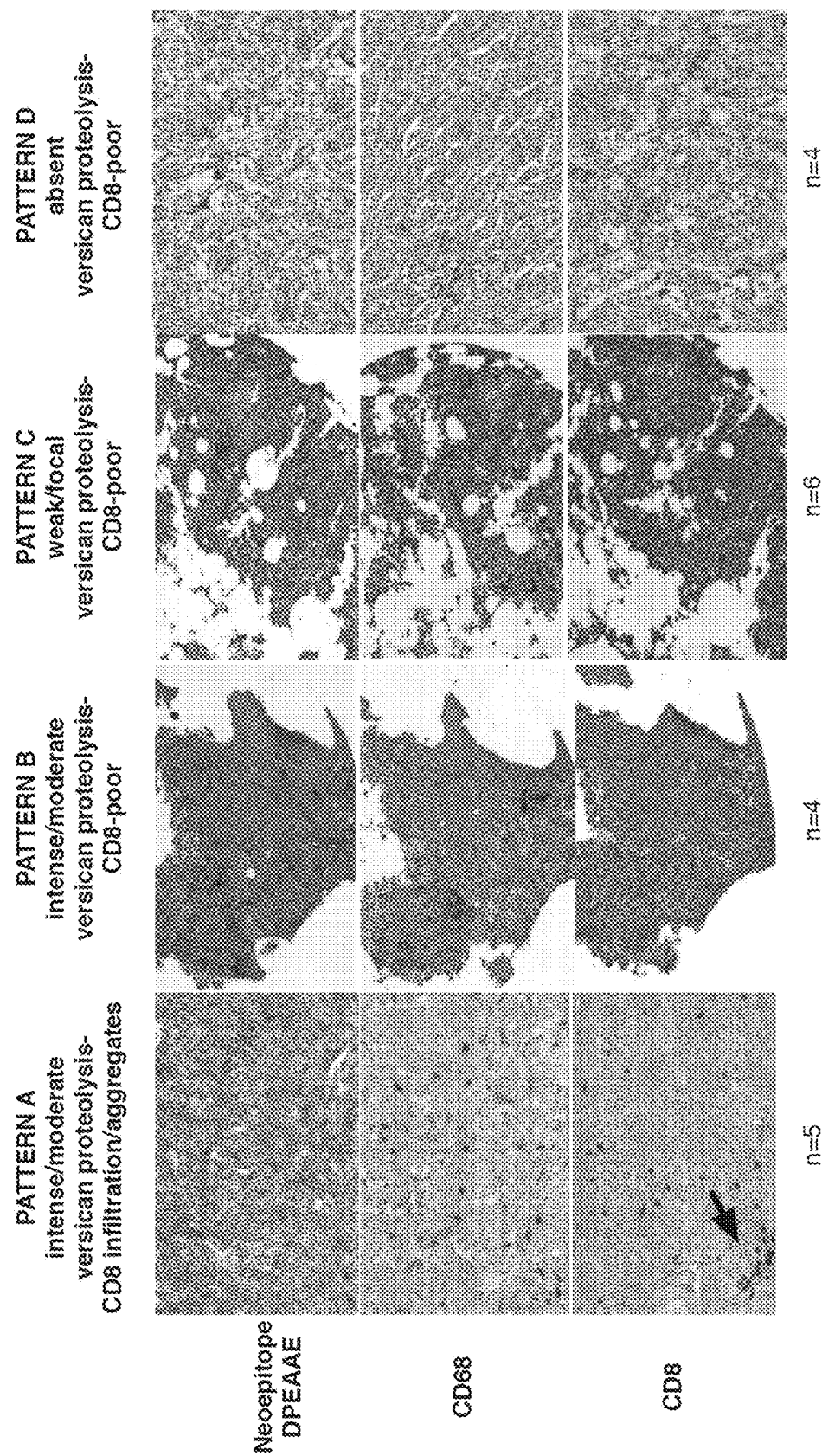

6 Claims, 24 Drawing Sheets
Specification includes a Sequence Listing.

(56) References Cited

OTHER PUBLICATIONS

Markowitz SD, Bertagnolli MM. Molecular origins of cancer: Molecular basis of colorectal cancer. N Engl J Med 2009;361(25):2449-60.

Marley AR, Nan H. Epidemiology of colorectal cancer. Int J Mol Epidemiol Genet 2016;7(3):105-14.

McMahon M, Ye S, Izzard L, Dlugolenski D, Tripp RA, Bean AG, et al. ADAMTS5 is a Critical Regulator of Virus-Specific T Cell Immunity. PLoS Biol 2016;14(11):e1002580.

Nandadasa S, Foulcer S, Apte SS. The multiple, complex roles of versican and its proteolytic turnover by ADAMTS proteases during embryogenesis. Matrix Biol 2014;35:34-41.

Pitt JM, Vetizou M, Waldschmitt N, Kroemer G, Chamaillard M, Boneca IG, et al. Fine-Tuning Cancer Immunotherapy: Optimizing the Gut Microbiome. Cancer Res 2016;76(16):4602-7.

Rekoske BT, McNeel DG. Immunotherapy for prostate cancer: False promises or true hope? Cancer 2016;122(23):3598-607.

Ricciardelli C, Sakko AJ, Ween MP, Russell DL, Horsfall DJ. The biological role and regulation of versican levels in cancer. Cancer Metastasis Rev 2009;28(1-2)233-45.

Salmon H, Idoyaga J, Rahman A, Leboeuf M, Remark R, Jordan S, et al. Expansion and Activation of CD103(+) Dendritic Cell Progenitors at the Tumor Site Enhances Tumor Responses to Therapeutic PD-L1 and BRAF Inhibition. Immunity 2016;44(4):924-38.

Sichien D, Scott CL, Martens L, Vanderkerken M, Van Gassen S, Plantinga M, et al. IRF8 Transcription Factor Controls Survival and Function of Terminally Differentiated Conventional and Plasmacytoid Dendritic Cells, Respectively. Immunity 2016.

Spranger S, Bao R, Gajewski TF. Melanoma-intrinsic beta-catenin signalling prevents anti-tumour immunity. Nature 2015;523(7559)231-5.

Spranger S, Sivan A, Corrales L, Gajewski TF. Tumor and Host Factors Controlling Antitumor Immunity and Efficacy of Cancer Immunotherapy. Adv Immunol 2016;130:75-93.

Tang M, Diao J, Gu H, Khatri I, Zhao J, Cattral MS. Toll-like Receptor 2 Activation Promotes Tumor Dendritic Cell Dysfunction by Regulating IL-6 and IL-10 Receptor Signaling. Cell Rep 2015;13(12):2851-64.

Topalian SL, Hodi FS, Brahmer JR, Gettinger SN, Smith DC, McDermott DF, et al. Safety, activity, and immune correlates of anti-PD-1 antibody in cancer. N Engl J Med 2012;366(26):2443-54.

Wang K, Karin M. Tumor-Elicited Inflammation and Colorectal Cancer. Adv Cancer Res 2015;128:173-96.

Westdorp H, Fennemann FL, Weren RD, Bisseling TM, Ligtenberg MJ, Figdor CG, et al. Opportunities for immunotherapy in microsatellite instable colorectal cancer. Cancer Immunol Immunother 2016;65(10)1249-59.

Wight TN, Kang I, Merrilees MJ. Versican and the control of inflammation. Matrix Biol 2014;35:152-61.

Woo SR, Corrales L, Gajewski TF. Innate immune recognition of cancer. Annu Rev Immunol 2015;33:445-74.

Wu YJ, La Pierre DP, Wu J, Yee AJ, Yang BB. The interaction of versican with its binding partners. Cell Res 2005;15(7):483-94.

Zhang Z, Miao L, Wang L. Inflammation amplification by versican: the first mediator. Int J Mol Sci 2012;13(6):6873-82.

Hope et al., "Versican-derived matrikines regulate Batf3-dendritic cell differentiation and promote T-cell infiltration in colorectal cancer," J. Immunol. Sep. 1, 2017; 199(5): 1933-1941.

Kischel, et al., "Versican overexpression in human breast cancer lesions: known and new isoforms for stromal tumor targeting," Int'l J. Can., 126, 640-650 (2010).

\* cited by examiner

Figure 5

A

| Genes | Log² fold |
|---|---|
| TNFAIP8L2-SCNM1 | 2.771 |
| VCAN | 1.629 |
| MX1 | 1.560 |
| IFI44L | 1.481 |
| IFI44 | 1.447 |
| THBD | 1.393 |
| IFITM1 | 1.392 |
| TRIM22 | 1.342 |
| CCL2 | 1.295 |
| LOC154092 | 1.293 |
| IL8 | 1.281 |
| MMP9 | 1.271 |
| XAF1 | 1.243 |
| IFIT1 | 1.214 |
| ZNF618 | 1.198 |
| GLIS3 | 1.140 |
| MX2 | 1.102 |
| IFI6 | 1.092 |
| PLAU | 1.010 |
| OAS3 | 0.887 |
| OAS2 | 0.534 |
| PARP14 | 0.485 |
| STAT1 | 0.436 |

B

| Genes (1-20) | Log² fold | Genes (20-40) | Log² fold |
|---|---|---|---|
| VCAN | 3.074 | PCDHGA9 | 1.150 |
| MTHFS | 2.723 | CCL7 | 1.140 |
| SIGLEC1 | 1.719 | COL6A2 | 1.113 |
| IFI44L | 1.637 | LIF | 1.080 |
| PLVAP | 1.624 | SIGLEC11 | 1.077 |
| ISG15 | 1.587 | CMPK2 | 1.076 |
| ICAM5 | 1.583 | ANGPTL6 | 1.069 |
| RSAD2 | 1.541 | ASRGL1 | 1.038 |
| IFI44 | 1.460 | FCGBP | 1.020 |
| OASL | 1.454 | LRRC18 | 1.011 |
| TRIM22 | 1.432 | COLEC12 | 1.011 |
| ABHD8 | 1.367 | C9 | 1.008 |
| CD14 | 1.351 | GAA | 1.002 |
| MAP1S | 1.333 | EBI3 | 1.31 |
| IFIT1 | 1.323 | NBPF11 | -8.617 |
| PHLDA2 | 1.312 | ARL2-SNX15 | -4.327 |
| MMRN2 | 1.295 | AGPHD1 | -3.194 |
| CCL2 | 1.277 | MPDZ | -3.180 |
| MMP9 | 1.249 | | |
| MX1 | 1.205 | | |
| ABCA1 | 1.174 | | |
| IFITM1 | 1.171 | | |

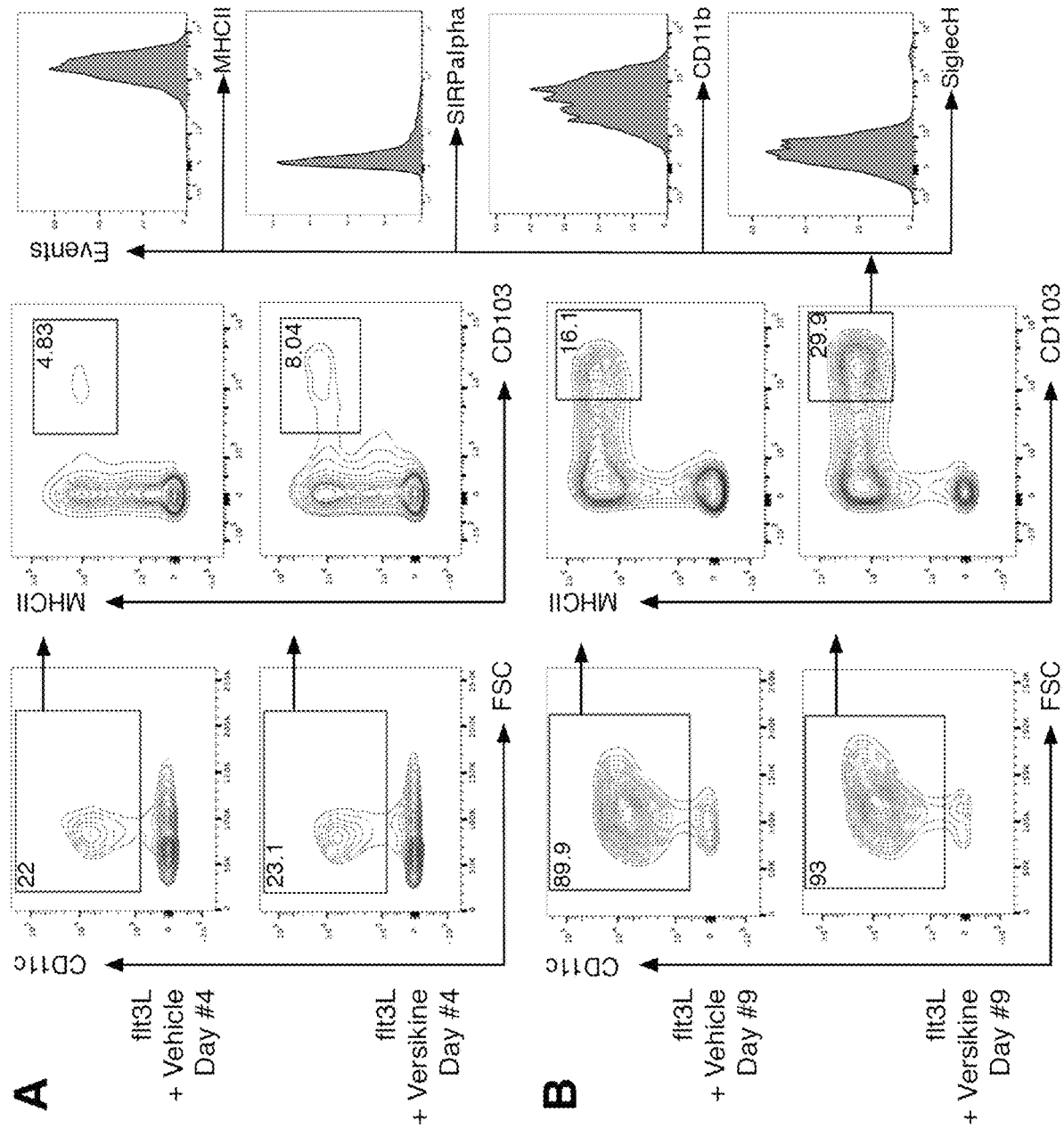

Figure 4:
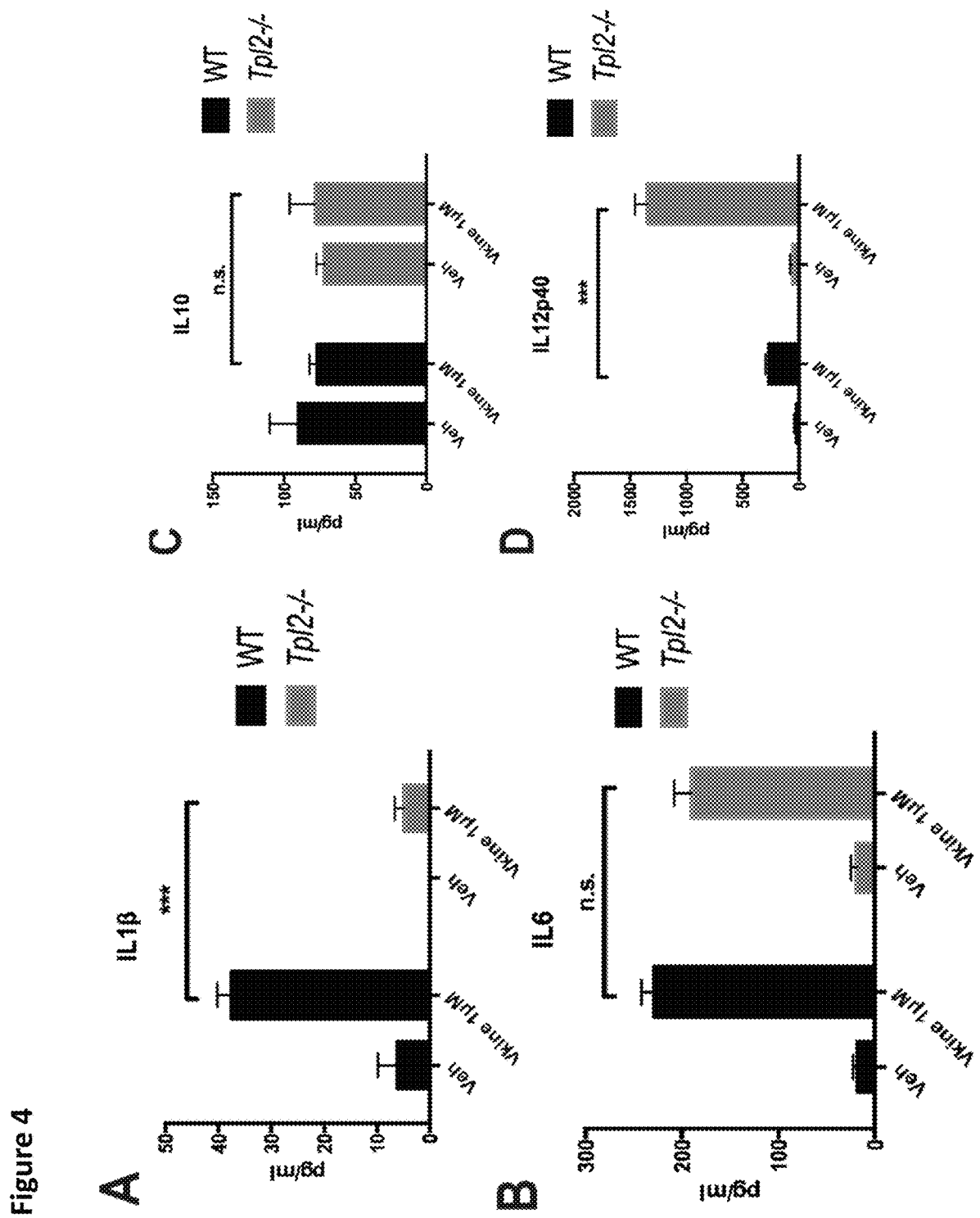
Figure 4:
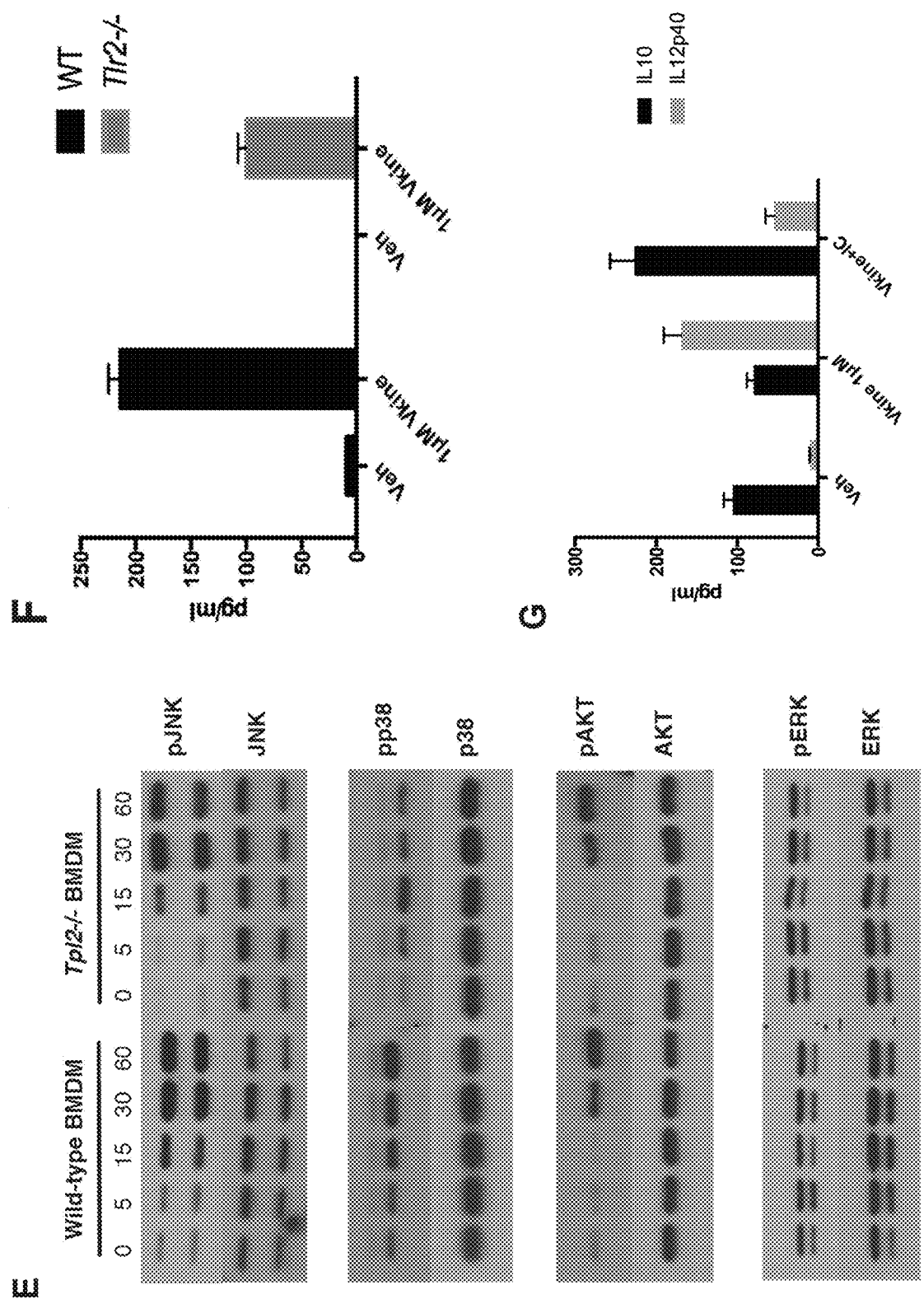

Figure 9
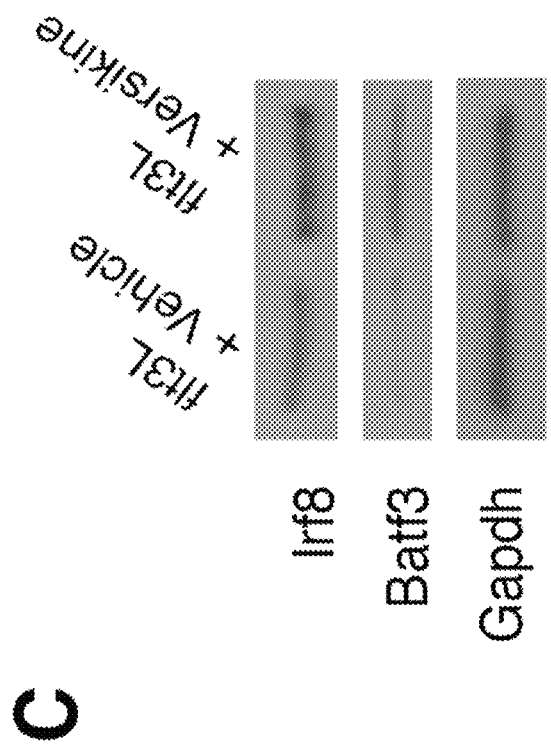
C
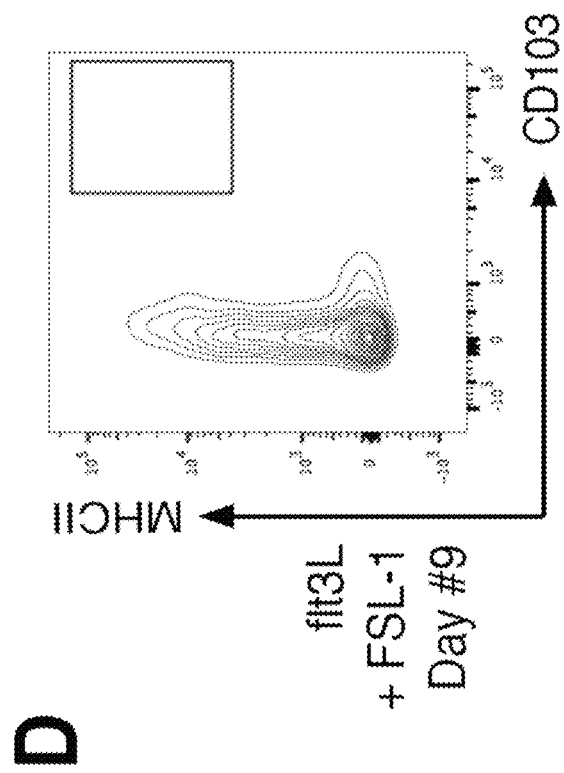
D
FIGURE 4

SEQUENCE LISTING

```
<160> NUMBER OF SEQ ID NOS: 27

<210> SEQ ID NO 1
<211> LENGTH: 2409
<212> TYPE: PRT
<213> ORGANISM: Homo sapiens
```

<400> SEQUENCE: 1

```
Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Arg Met Ser Asp
            340                 345                 350

Leu Ser Val Ile Gly His Pro Ile Asp Ser Glu Ser Lys Glu Asp Glu
        355                 360                 365

Pro Cys Ser Glu Glu Thr Asp Pro Val His Asp Leu Met Ala Glu Ile
    370                 375                 380

Leu Pro Glu Phe Pro Asp Ile Ile Glu Ile Asp Leu Tyr His Ser Glu
385                 390                 395                 400

Glu Asn Glu Glu Glu Glu Glu Cys Ala Asn Ala Thr Asp Val Thr
                405                 410                 415
```

```
Thr Thr Pro Ser Val Gln Tyr Ile Asn Gly Lys His Leu Val Thr Thr
            420                 425                 430
Val Pro Lys Asp Pro Glu Ala Ala Glu Ala Arg Arg Gly Gln Phe Glu
            435                 440                 445
Ser Val Ala Pro Ser Gln Asn Phe Ser Asp Ser Ser Glu Ser Asp Thr
            450                 455                 460
His Pro Phe Val Ile Ala Lys Thr Glu Leu Ser Thr Ala Val Gln Pro
465                 470                 475                 480
Asn Glu Ser Thr Glu Thr Thr Glu Ser Leu Glu Val Thr Trp Lys Pro
                    485                 490                 495
Glu Thr Tyr Pro Glu Thr Ser Glu His Phe Ser Gly Gly Glu Pro Asp
                500                 505                 510
Val Phe Pro Thr Val Pro Phe His Glu Glu Phe Glu Ser Gly Thr Ala
                515                 520                 525
Lys Lys Gly Ala Glu Ser Val Thr Glu Arg Asp Thr Glu Val Gly His
530                 535                 540
Gln Ala His Glu His Thr Glu Pro Val Ser Leu Phe Pro Glu Glu Ser
545                 550                 555                 560
Ser Gly Glu Ile Ala Ile Asp Gln Glu Ser Gln Lys Ile Ala Phe Ala
                    565                 570                 575
Arg Ala Thr Glu Val Thr Phe Gly Glu Glu Val Glu Lys Ser Thr Ser
                580                 585                 590
Val Thr Tyr Thr Pro Thr Ile Val Pro Ser Ser Ala Ser Ala Tyr Val
                595                 600                 605
Ser Glu Glu Glu Ala Val Thr Leu Ile Gly Asn Pro Trp Pro Asp Asp
610                 615                 620
Leu Leu Ser Thr Lys Glu Ser Trp Val Glu Ala Thr Pro Arg Gln Val
625                 630                 635                 640
Val Glu Leu Ser Gly Ser Ser Ile Pro Ile Thr Glu Gly Ser Gly
                    645                 650                 655
Glu Ala Glu Glu Asp Glu Asp Thr Met Phe Thr Met Val Thr Asp Leu
                660                 665                 670
Ser Gln Arg Asn Thr Thr Asp Thr Leu Ile Thr Leu Asp Thr Ser Arg
                    675                 680                 685
Ile Ile Thr Glu Ser Phe Phe Glu Val Pro Ala Thr Thr Ile Tyr Pro
690                 695                 700
Val Ser Glu Gln Pro Ser Ala Lys Val Val Pro Thr Lys Phe Val Ser
705                 710                 715                 720
Glu Thr Asp Thr Ser Glu Trp Ile Ser Ser Thr Thr Val Glu Glu Lys
                    725                 730                 735
Lys Arg Lys Glu Glu Glu Gly Thr Thr Gly Thr Ala Ser Thr Phe Glu
                740                 745                 750
Val Tyr Ser Ser Thr Gln Arg Ser Asp Gln Leu Ile Leu Pro Phe Glu
                755                 760                 765
Leu Glu Ser Pro Asn Val Ala Thr Ser Ser Asp Ser Gly Thr Arg Lys
770                 775                 780
Ser Phe Met Ser Leu Thr Thr Pro Thr Gln Ser Glu Arg Glu Met Thr
785                 790                 795                 800
Asp Ser Thr Pro Val Phe Thr Glu Thr Asn Thr Leu Glu Asn Leu Gly
                    805                 810                 815
Ala Gln Thr Thr Glu His Ser Ser Ile His Gln Pro Gly Val Gln Glu
                820                 825                 830
```

-continued

Gly Leu Thr Thr Leu Pro Arg Ser Pro Ala Ser Val Phe Met Glu Gln
835                 840                 845

Gly Ser Gly Glu Ala Ala Asp Pro Glu Thr Thr Thr Val Ser Ser
850                 855                 860

Phe Ser Leu Asn Val Glu Tyr Ala Ile Gln Ala Glu Lys Glu Val Ala
865                 870                 875                 880

Gly Thr Leu Ser Pro His Val Glu Thr Thr Phe Ser Thr Pro Thr
        885                 890                 895

Gly Leu Val Leu Ser Thr Val Met Asp Arg Val Val Ala Glu Asn Ile
            900                 905                 910

Thr Gln Thr Ser Arg Glu Ile Val Ile Ser Glu Arg Leu Gly Glu Pro
        915                 920                 925

Asn Tyr Gly Ala Glu Ile Arg Gly Phe Ser Thr Gly Phe Pro Leu Glu
        930                 935                 940

Glu Asp Phe Ser Gly Asp Phe Arg Glu Tyr Ser Thr Val Ser His Pro
945                 950                 955                 960

Ile Ala Lys Glu Glu Thr Val Met Met Glu Gly Ser Gly Asp Ala Ala
            965                 970                 975

Phe Arg Asp Thr Gln Thr Ser Pro Ser Thr Val Pro Thr Ser Val His
        980                 985                 990

Ile Ser His Ile Ser Asp Ser Glu Gly Pro Ser Ser Thr Met Val Ser
        995                 1000                1005

Thr Ser Ala Phe Pro Trp Glu Glu Phe Thr Ser Ser Ala Glu Gly
    1010                1015                1020

Ser Gly Glu Gln Leu Val Thr Val Ser Ser Ser Val Val Pro Val
    1025                1030                1035

Leu Pro Ser Ala Val Gln Lys Phe Ser Gly Thr Ala Ser Ser Ile
    1040                1045                1050

Ile Asp Glu Gly Leu Gly Glu Val Gly Thr Val Asn Glu Ile Asp
    1055                1060                1065

Arg Arg Ser Thr Ile Leu Pro Thr Ala Glu Val Glu Gly Thr Lys
    1070                1075                1080

Ala Pro Val Glu Lys Glu Glu Val Lys Val Ser Gly Thr Val Ser
    1085                1090                1095

Thr Asn Phe Pro Gln Thr Ile Glu Pro Ala Lys Leu Trp Ser Arg
    1100                1105                1110

Gln Glu Val Asn Pro Val Arg Gln Glu Ile Glu Ser Glu Thr Thr
    1115                1120                1125

Ser Glu Glu Gln Ile Gln Glu Glu Lys Ser Phe Glu Ser Pro Gln
    1130                1135                1140

Asn Ser Pro Ala Thr Glu Gln Thr Ile Phe Asp Ser Gln Thr Phe
    1145                1150                1155

Thr Glu Thr Glu Leu Lys Thr Thr Asp Tyr Ser Val Leu Thr Thr
    1160                1165                1170

Lys Lys Thr Tyr Ser Asp Asp Lys Glu Met Lys Glu Glu Asp Thr
    1175                1180                1185

Ser Leu Val Asn Met Ser Thr Pro Asp Pro Asp Ala Asn Gly Leu
    1190                1195                1200

Glu Ser Tyr Thr Thr Leu Pro Glu Ala Thr Glu Lys Ser His Phe
    1205                1210                1215

Phe Leu Ala Thr Ala Leu Val Thr Glu Ser Ile Pro Ala Glu His
    1220                1225                1230

-continued

Val Val Thr Asp Ser Pro Ile Lys Lys Glu Glu Ser Thr Lys His
1235                1240                1245

Phe Pro Lys Gly Met Arg Pro Thr Ile Gln Glu Ser Asp Thr Glu
1250                1255                1260

Leu Leu Phe Ser Gly Leu Gly Ser Gly Glu Glu Val Leu Pro Thr
1265                1270                1275

Leu Pro Thr Glu Ser Val Asn Phe Thr Glu Val Glu Gln Ile Asn
1280                1285                1290

Asn Thr Leu Tyr Pro His Thr Ser Gln Val Glu Ser Thr Ser Ser
1295                1300                1305

Asp Lys Ile Glu Asp Phe Asn Arg Met Glu Asn Val Ala Lys Glu
1310                1315                1320

Val Gly Pro Leu Val Ser Gln Thr Asp Ile Phe Glu Gly Ser Gly
1325                1330                1335

Ser Val Thr Ser Thr Thr Leu Ile Glu Ile Leu Ser Asp Thr Gly
1340                1345                1350

Ala Glu Gly Pro Thr Val Ala Pro Leu Pro Phe Ser Thr Asp Ile
1355                1360                1365

Gly His Pro Gln Asn Gln Thr Val Arg Trp Ala Glu Glu Ile Gln
1370                1375                1380

Thr Ser Arg Pro Gln Thr Ile Thr Glu Gln Asp Ser Asn Lys Asn
1385                1390                1395

Ser Ser Thr Ala Glu Ile Asn Glu Thr Thr Thr Ser Ser Thr Asp
1400                1405                1410

Phe Leu Ala Arg Ala Tyr Gly Phe Glu Met Ala Lys Glu Phe Val
1415                1420                1425

Thr Ser Ala Pro Lys Pro Ser Asp Leu Tyr Tyr Glu Pro Ser Gly
1430                1435                1440

Glu Gly Ser Gly Glu Val Asp Ile Val Asp Ser Phe His Thr Ser
1445                1450                1455

Ala Thr Thr Gln Ala Thr Arg Gln Glu Ser Ser Thr Thr Phe Val
1460                1465                1470

Ser Asp Gly Ser Leu Glu Lys His Pro Glu Val Pro Ser Ala Lys
1475                1480                1485

Ala Val Thr Ala Asp Gly Phe Pro Thr Val Ser Val Met Leu Pro
1490                1495                1500

Leu His Ser Glu Gln Asn Lys Ser Ser Pro Asp Pro Thr Ser Thr
1505                1510                1515

Leu Ser Asn Thr Val Ser Tyr Glu Arg Ser Thr Asp Gly Ser Phe
1520                1525                1530

Gln Asp Arg Phe Arg Glu Phe Glu Asp Ser Thr Leu Lys Pro Asn
1535                1540                1545

Arg Lys Lys Pro Thr Glu Asn Ile Ile Ile Asp Leu Asp Lys Glu
1550                1555                1560

Asp Lys Asp Leu Ile Leu Thr Ile Thr Glu Ser Thr Ile Leu Glu
1565                1570                1575

Ile Leu Pro Glu Leu Thr Ser Asp Lys Asn Thr Ile Ile Asp Ile
1580                1585                1590

Asp His Thr Lys Pro Val Tyr Glu Asp Ile Leu Gly Met Gln Thr
1595                1600                1605

Asp Ile Asp Thr Glu Val Pro Ser Glu Pro His Asp Ser Asn Asp
1610                1615                1620

-continued

Glu Ser Asn Asp Asp Ser Thr Gln Val Gln Glu Ile Tyr Glu Ala
1625                1630                1635

Ala Val Asn Leu Ser Leu Thr Glu Glu Thr Phe Glu Gly Ser Ala
1640                1645                1650

Asp Val Leu Ala Ser Tyr Thr Gln Ala Thr His Asp Glu Ser Met
1655                1660                1665

Thr Tyr Glu Asp Arg Ser Gln Leu Asp His Met Gly Phe His Phe
1670                1675                1680

Thr Thr Gly Ile Pro Ala Pro Ser Thr Glu Thr Glu Leu Asp Val
1685                1690                1695

Leu Leu Pro Thr Ala Thr Ser Leu Pro Ile Pro Arg Lys Ser Ala
1700                1705                1710

Thr Val Ile Pro Glu Ile Glu Gly Ile Lys Ala Glu Ala Lys Ala
1715                1720                1725

Leu Asp Asp Met Phe Glu Ser Ser Thr Leu Ser Asp Gly Gln Ala
1730                1735                1740

Ile Ala Asp Gln Ser Glu Ile Ile Pro Thr Leu Gly Gln Phe Glu
1745                1750                1755

Arg Thr Gln Glu Glu Tyr Glu Asp Lys Lys His Ala Gly Pro Ser
1760                1765                1770

Phe Gln Pro Glu Phe Ser Ser Gly Ala Glu Glu Ala Leu Val Asp
1775                1780                1785

His Thr Pro Tyr Leu Ser Ile Ala Thr His Leu Met Asp Gln
1790                1795                1800

Ser Val Thr Glu Val Pro Asp Val Met Glu Gly Ser Asn Pro Pro
1805                1810                1815

Tyr Tyr Thr Asp Thr Thr Leu Ala Val Ser Thr Phe Ala Lys Leu
1820                1825                1830

Ser Ser Gln Thr Pro Ser Ser Pro Leu Thr Ile Tyr Ser Gly Ser
1835                1840                1845

Glu Ala Ser Gly His Thr Glu Ile Pro Gln Pro Ser Ala Leu Pro
1850                1855                1860

Gly Ile Asp Val Gly Ser Ser Val Met Ser Pro Gln Asp Ser Phe
1865                1870                1875

Lys Glu Ile His Val Asn Ile Glu Ala Thr Phe Lys Pro Ser Ser
1880                1885                1890

Glu Glu Tyr Leu His Ile Thr Glu Pro Pro Ser Leu Ser Pro Asp
1895                1900                1905

Thr Lys Leu Glu Pro Ser Glu Asp Asp Gly Lys Pro Glu Leu Leu
1910                1915                1920

Glu Glu Met Glu Ala Ser Pro Thr Glu Leu Ile Ala Val Glu Gly
1925                1930                1935

Thr Glu Ile Leu Gln Asp Phe Gln Asn Lys Thr Asp Gly Gln Val
1940                1945                1950

Ser Gly Glu Ala Ile Lys Met Phe Pro Thr Ile Lys Thr Pro Glu
1955                1960                1965

Ala Gly Thr Val Ile Thr Thr Ala Asp Glu Ile Glu Leu Glu Gly
1970                1975                1980

Ala Thr Gln Trp Pro His Ser Thr Ser Ala Ser Ala Thr Tyr Gly
1985                1990                1995

Val Glu Ala Gly Val Val Pro Trp Leu Ser Pro Gln Thr Ser Glu
2000                2005                2010

```
Arg Pro Thr Leu Ser Ser Ser Pro Glu Ile Asn Pro Glu Thr Gln
2015                2020                2025

Ala Ala Leu Ile Arg Gly Gln Asp Ser Thr Ile Ala Ala Ser Glu
2030                2035                2040

Gln Gln Val Ala Ala Arg Ile Leu Asp Ser Asn Asp Gln Ala Thr
2045                2050                2055

Val Asn Pro Val Glu Phe Asn Thr Glu Val Ala Thr Pro Pro Phe
2060                2065                2070

Ser Leu Leu Glu Thr Ser Asn Glu Thr Asp Phe Leu Ile Gly Ile
2075                2080                2085

Asn Glu Glu Ser Val Glu Gly Thr Ala Ile Tyr Leu Pro Gly Pro
2090                2095                2100

Asp Arg Cys Lys Met Asn Pro Cys Leu Asn Gly Gly Thr Cys Tyr
2105                2110                2115

Pro Thr Glu Thr Ser Tyr Val Cys Thr Cys Val Pro Gly Tyr Ser
2120                2125                2130

Gly Asp Gln Cys Glu Leu Asp Phe Asp Glu Cys His Ser Asn Pro
2135                2140                2145

Cys Arg Asn Gly Ala Thr Cys Val Asp Gly Phe Asn Thr Phe Arg
2150                2155                2160

Cys Leu Cys Leu Pro Ser Tyr Val Gly Ala Leu Cys Glu Gln Asp
2165                2170                2175

Thr Glu Thr Cys Asp Tyr Gly Trp His Lys Phe Gln Gly Gln Cys
2180                2185                2190

Tyr Lys Tyr Phe Ala His Arg Arg Thr Trp Asp Ala Ala Glu Arg
2195                2200                2205

Glu Cys Arg Leu Gln Gly Ala His Leu Thr Ser Ile Leu Ser His
2210                2215                2220

Glu Glu Gln Met Phe Val Asn Arg Val Gly His Asp Tyr Gln Trp
2225                2230                2235

Ile Gly Leu Asn Asp Lys Met Phe Glu His Asp Phe Arg Trp Thr
2240                2245                2250

Asp Gly Ser Thr Leu Gln Tyr Glu Asn Trp Arg Pro Asn Gln Pro
2255                2260                2265

Asp Ser Phe Phe Ser Ala Gly Glu Asp Cys Val Val Ile Ile Trp
2270                2275                2280

His Glu Asn Gly Gln Trp Asn Asp Val Pro Cys Asn Tyr His Leu
2285                2290                2295

Thr Tyr Thr Cys Lys Lys Gly Thr Val Ala Cys Gly Gln Pro Pro
2300                2305                2310

Val Val Glu Asn Ala Lys Thr Phe Gly Lys Met Lys Pro Arg Tyr
2315                2320                2325

Glu Ile Asn Ser Leu Ile Arg Tyr His Cys Lys Asp Gly Phe Ile
2330                2335                2340

Gln Arg His Leu Pro Thr Ile Arg Cys Leu Gly Asn Gly Arg Trp
2345                2350                2355

Ala Ile Pro Lys Ile Thr Cys Met Asn Pro Ser Ala Tyr Gln Arg
2360                2365                2370

Thr Tyr Ser Met Lys Tyr Phe Lys Asn Ser Ser Ser Ala Lys Asp
2375                2380                2385
```

```
Asn Ser Ile Asn Thr Ser Lys His Asp His Arg Trp Ser Arg Arg
    2390            2395                2400

Trp Gln Glu Ser Arg Arg
    2405
```

<210> SEQ ID NO 2
<211> LENGTH: 2389
<212> TYPE: PRT
<213> ORGANISM: Homo sapiens

<400> SEQUENCE: 2

```
Leu His Lys Val Lys Val Gly Lys Ser Pro Val Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
                35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
                100                 105                 110

Met Tyr Gly Ile Glu Asp Thr Gln Asp Thr Val Ser Leu Thr Val Asp
                115                 120                 125

Gly Val Val Phe His Tyr Arg Ala Ala Thr Ser Arg Tyr Thr Leu Asn
130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
                180                 185                 190

Pro Arg Val Gly Cys Tyr Gly Asp Lys Met Gly Lys Ala Gly Val Arg
                195                 200                 205

Thr Tyr Gly Phe Arg Ser Pro Gln Glu Thr Tyr Asp Val Tyr Cys Tyr
210                 215                 220

Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
                245                 250                 255

Leu Ala Thr Val Gly Glu Leu Gln Ala Ala Trp Arg Asn Gly Phe Asp
                260                 265                 270

Gln Cys Asp Tyr Gly Trp Leu Ser Asp Ala Ser Val Arg His Pro Val
                275                 280                 285

Thr Val Ala Arg Ala Gln Cys Gly Gly Gly Leu Leu Gly Val Arg Thr
                290                 295                 300

Leu Tyr Arg Phe Glu Asn Gln Thr Gly Phe Pro Pro Asp Ser Arg
305                 310                 315                 320

Phe Asp Ala Tyr Cys Phe Lys Arg Arg Met Ser Asp Leu Ser Val Ile
                325                 330                 335

Gly His Pro Ile Asp Ser Glu Ser Lys Glu Asp Glu Pro Cys Ser Glu
                340                 345                 350
```

-continued

```
Glu Thr Asp Pro Val His Asp Leu Met Ala Glu Ile Leu Pro Glu Phe
            355                 360                 365

Pro Asp Ile Ile Glu Ile Asp Leu Tyr His Ser Glu Glu Asn Glu Glu
        370                 375                 380

Glu Glu Glu Glu Cys Ala Asn Ala Thr Asp Val Thr Thr Thr Pro Ser
385                 390                 395                 400

Val Gln Tyr Ile Asn Gly Lys His Leu Val Thr Thr Val Pro Lys Asp
            405                 410                 415

Pro Glu Ala Ala Glu Ala Arg Arg Gly Gln Phe Glu Ser Val Ala Pro
        420                 425                 430

Ser Gln Asn Phe Ser Asp Ser Ser Glu Ser Asp Thr His Pro Phe Val
            435                 440                 445

Ile Ala Lys Thr Glu Leu Ser Thr Ala Val Gln Pro Asn Glu Ser Thr
        450                 455                 460

Glu Thr Thr Glu Ser Leu Glu Val Thr Trp Lys Pro Glu Thr Tyr Pro
465                 470                 475                 480

Glu Thr Ser Glu His Phe Ser Gly Gly Glu Pro Asp Val Phe Pro Thr
            485                 490                 495

Val Pro Phe His Glu Glu Phe Glu Ser Gly Thr Ala Lys Lys Gly Ala
        500                 505                 510

Glu Ser Val Thr Glu Arg Asp Thr Glu Val Gly His Gln Ala His Glu
            515                 520                 525

His Thr Glu Pro Val Ser Leu Phe Pro Glu Glu Ser Ser Gly Glu Ile
        530                 535                 540

Ala Ile Asp Gln Glu Ser Gln Lys Ile Ala Phe Ala Arg Ala Thr Glu
545                 550                 555                 560

Val Thr Phe Gly Glu Glu Val Glu Lys Ser Thr Ser Val Thr Tyr Thr
            565                 570                 575

Pro Thr Ile Val Pro Ser Ser Ala Ser Ala Tyr Val Ser Glu Glu Glu
        580                 585                 590

Ala Val Thr Leu Ile Gly Asn Pro Trp Pro Asp Asp Leu Leu Ser Thr
            595                 600                 605

Lys Glu Ser Trp Val Glu Ala Thr Pro Arg Gln Val Val Glu Leu Ser
        610                 615                 620

Gly Ser Ser Ser Ile Pro Ile Thr Glu Gly Ser Gly Glu Ala Glu Glu
625                 630                 635                 640

Asp Glu Asp Thr Met Phe Thr Met Val Thr Asp Leu Ser Gln Arg Asn
            645                 650                 655

Thr Thr Asp Thr Leu Ile Thr Leu Asp Thr Ser Arg Ile Ile Thr Glu
        660                 665                 670

Ser Phe Phe Glu Val Pro Ala Thr Thr Ile Tyr Pro Val Ser Glu Gln
            675                 680                 685

Pro Ser Ala Lys Val Val Pro Thr Lys Phe Val Ser Glu Thr Asp Thr
        690                 695                 700

Ser Glu Trp Ile Ser Ser Thr Thr Val Glu Glu Lys Lys Arg Lys Glu
705                 710                 715                 720

Glu Glu Gly Thr Thr Gly Thr Ala Ser Thr Phe Glu Val Tyr Ser Ser
            725                 730                 735

Thr Gln Arg Ser Asp Gln Leu Ile Leu Pro Phe Glu Leu Glu Ser Pro
        740                 745                 750

Asn Val Ala Thr Ser Ser Asp Ser Gly Thr Arg Lys Ser Phe Met Ser
            755                 760                 765
```

-continued

Leu Thr Thr Pro Thr Gln Ser Glu Arg Glu Met Thr Asp Ser Thr Pro
770                 775                 780

Val Phe Thr Glu Thr Asn Thr Leu Glu Asn Leu Gly Ala Gln Thr Thr
785                 790                 795                 800

Glu His Ser Ser Ile His Gln Pro Gly Val Gln Glu Gly Leu Thr Thr
                805                 810                 815

Leu Pro Arg Ser Pro Ala Ser Val Phe Met Glu Gln Gly Ser Gly Glu
            820                 825                 830

Ala Ala Ala Asp Pro Glu Thr Thr Val Ser Ser Phe Ser Leu Asn
                835                 840                 845

Val Glu Tyr Ala Ile Gln Ala Glu Lys Glu Val Ala Gly Thr Leu Ser
850                 855                 860

Pro His Val Glu Thr Thr Phe Ser Thr Glu Pro Thr Gly Leu Val Leu
865                 870                 875                 880

Ser Thr Val Met Asp Arg Val Ala Glu Asn Ile Thr Gln Thr Ser
                885                 890                 895

Arg Glu Ile Val Ile Ser Glu Arg Leu Gly Pro Asn Tyr Gly Ala
                900                 905                 910

Glu Ile Arg Gly Phe Ser Thr Gly Phe Pro Leu Glu Glu Asp Phe Ser
            915                 920                 925

Gly Asp Phe Arg Glu Tyr Ser Thr Val Ser His Pro Ile Ala Lys Glu
930                 935                 940

Glu Thr Val Met Met Glu Gly Ser Gly Asp Ala Ala Phe Arg Asp Thr
945                 950                 955                 960

Gln Thr Ser Pro Ser Thr Val Pro Thr Ser Val His Ile Ser His Ile
                965                 970                 975

Ser Asp Ser Glu Gly Pro Ser Ser Thr Met Val Ser Thr Ser Ala Phe
            980                 985                 990

Pro Trp Glu Glu Phe Thr Ser Ser Ala Glu Gly Ser Gly Glu Gln Leu
            995                 1000                1005

Val Thr Val Ser Ser Ser Val Val Pro Val Leu Pro Ser Ala Val
    1010                1015                1020

Gln Lys Phe Ser Gly Thr Ala Ser Ser Ile Ile Asp Glu Gly Leu
    1025                1030                1035

Gly Glu Val Gly Thr Val Asn Glu Ile Asp Arg Arg Ser Thr Ile
    1040                1045                1050

Leu Pro Thr Ala Glu Val Glu Gly Thr Lys Ala Pro Val Glu Lys
    1055                1060                1065

Glu Glu Val Lys Val Ser Gly Thr Val Ser Thr Asn Phe Pro Gln
    1070                1075                1080

Thr Ile Glu Pro Ala Lys Leu Trp Ser Arg Gln Glu Val Asn Pro
    1085                1090                1095

Val Arg Gln Glu Ile Glu Ser Glu Thr Thr Ser Glu Glu Gln Ile
    1100                1105                1110

Gln Glu Glu Lys Ser Phe Glu Ser Pro Gln Asn Ser Pro Ala Thr
    1115                1120                1125

Glu Gln Thr Ile Phe Asp Ser Gln Thr Phe Thr Glu Thr Glu Leu
    1130                1135                1140

Lys Thr Thr Asp Tyr Ser Val Leu Thr Thr Lys Lys Thr Tyr Ser
    1145                1150                1155

Asp Asp Lys Glu Met Lys Glu Glu Asp Thr Ser Leu Val Asn Met
    1160                1165                1170

-continued

Ser Thr Pro Asp Pro Asp Ala Asn Gly Leu Glu Ser Tyr Thr Thr
1175                1180                1185

Leu Pro Glu Ala Thr Glu Lys Ser His Phe Phe Leu Ala Thr Ala
1190                1195                1200

Leu Val Thr Glu Ser Ile Pro Ala Glu His Val Val Thr Asp Ser
1205                1210                1215

Pro Ile Lys Lys Glu Glu Ser Thr Lys His Phe Pro Lys Gly Met
1220                1225                1230

Arg Pro Thr Ile Gln Glu Ser Asp Thr Glu Leu Leu Phe Ser Gly
1235                1240                1245

Leu Gly Ser Gly Glu Val Leu Pro Thr Leu Pro Thr Glu Ser
1250                1255                1260

Val Asn Phe Thr Glu Val Glu Gln Ile Asn Asn Thr Leu Tyr Pro
1265                1270                1275

His Thr Ser Gln Val Glu Ser Thr Ser Ser Asp Lys Ile Glu Asp
1280                1285                1290

Phe Asn Arg Met Glu Asn Val Ala Lys Glu Val Gly Pro Leu Val
1295                1300                1305

Ser Gln Thr Asp Ile Phe Glu Gly Ser Gly Ser Val Thr Ser Thr
1310                1315                1320

Thr Leu Ile Glu Ile Leu Ser Asp Thr Gly Ala Glu Gly Pro Thr
1325                1330                1335

Val Ala Pro Leu Pro Phe Ser Thr Asp Ile Gly His Pro Gln Asn
1340                1345                1350

Gln Thr Val Arg Trp Ala Glu Glu Ile Gln Thr Ser Arg Pro Gln
1355                1360                1365

Thr Ile Thr Glu Gln Asp Ser Asn Lys Asn Ser Ser Thr Ala Glu
1370                1375                1380

Ile Asn Glu Thr Thr Thr Ser Ser Thr Asp Phe Leu Ala Arg Ala
1385                1390                1395

Tyr Gly Phe Glu Met Ala Lys Glu Phe Val Thr Ser Ala Pro Lys
1400                1405                1410

Pro Ser Asp Leu Tyr Tyr Glu Pro Ser Gly Glu Gly Ser Gly Glu
1415                1420                1425

Val Asp Ile Val Asp Ser Phe His Thr Ser Ala Thr Thr Gln Ala
1430                1435                1440

Thr Arg Gln Glu Ser Ser Thr Thr Phe Val Ser Asp Gly Ser Leu
1445                1450                1455

Glu Lys His Pro Glu Val Pro Ser Ala Lys Ala Val Thr Ala Asp
1460                1465                1470

Gly Phe Pro Thr Val Ser Val Met Leu Pro Leu His Ser Glu Gln
1475                1480                1485

Asn Lys Ser Ser Pro Asp Pro Thr Ser Thr Leu Ser Asn Thr Val
1490                1495                1500

Ser Tyr Glu Arg Ser Thr Asp Gly Ser Phe Gln Asp Arg Phe Arg
1505                1510                1515

Glu Phe Glu Asp Ser Thr Leu Lys Pro Asn Arg Lys Lys Pro Thr
1520                1525                1530

Glu Asn Ile Ile Ile Asp Leu Asp Lys Glu Asp Lys Asp Leu Ile
1535                1540                1545

Leu Thr Ile Thr Glu Ser Thr Ile Leu Glu Ile Leu Pro Glu Leu
1550                1555                1560

```
Thr Ser Asp Lys Asn Thr Ile Ile Asp Ile Asp His Thr Lys Pro
1565                1570                1575

Val Tyr Glu Asp Ile Leu Gly Met Gln Thr Asp Ile Asp Thr Glu
    1580                1585                1590

Val Pro Ser Glu Pro His Asp Ser Asn Asp Ser Asn Asp Asp
1595                1600                1605

Ser Thr Gln Val Gln Glu Ile Tyr Glu Ala Ala Val Asn Leu Ser
    1610                1615                1620

Leu Thr Glu Glu Thr Phe Glu Gly Ser Ala Asp Val Leu Ala Ser
    1625                1630                1635

Tyr Thr Gln Ala Thr His Asp Glu Ser Met Thr Tyr Glu Asp Arg
    1640                1645                1650

Ser Gln Leu Asp His Met Gly Phe His Phe Thr Thr Gly Ile Pro
    1655                1660                1665

Ala Pro Ser Thr Glu Thr Glu Leu Asp Val Leu Leu Pro Thr Ala
    1670                1675                1680

Thr Ser Leu Pro Ile Pro Arg Lys Ser Ala Thr Val Ile Pro Glu
    1685                1690                1695

Ile Glu Gly Ile Lys Ala Glu Ala Lys Ala Leu Asp Asp Met Phe
    1700                1705                1710

Glu Ser Ser Thr Leu Ser Asp Gly Gln Ala Ile Ala Asp Gln Ser
    1715                1720                1725

Glu Ile Ile Pro Thr Leu Gly Gln Phe Glu Arg Thr Gln Glu Glu
    1730                1735                1740

Tyr Glu Asp Lys Lys His Ala Gly Pro Ser Phe Gln Pro Glu Phe
    1745                1750                1755

Ser Ser Gly Ala Glu Glu Ala Leu Val Asp His Thr Pro Tyr Leu
    1760                1765                1770

Ser Ile Ala Thr Thr His Leu Met Asp Gln Ser Val Thr Glu Val
    1775                1780                1785

Pro Asp Val Met Glu Gly Ser Asn Pro Pro Tyr Tyr Thr Asp Thr
    1790                1795                1800

Thr Leu Ala Val Ser Thr Phe Ala Lys Leu Ser Ser Gln Thr Pro
    1805                1810                1815

Ser Ser Pro Leu Thr Ile Tyr Ser Gly Ser Glu Ala Ser Gly His
    1820                1825                1830

Thr Glu Ile Pro Gln Pro Ser Ala Leu Pro Gly Ile Asp Val Gly
    1835                1840                1845

Ser Ser Val Met Ser Pro Gln Asp Ser Phe Lys Glu Ile His Val
    1850                1855                1860

Asn Ile Glu Ala Thr Phe Lys Pro Ser Ser Glu Glu Tyr Leu His
    1865                1870                1875

Ile Thr Glu Pro Pro Ser Leu Ser Pro Asp Thr Lys Leu Glu Pro
    1880                1885                1890

Ser Glu Asp Asp Gly Lys Pro Glu Leu Leu Glu Glu Met Glu Ala
    1895                1900                1905

Ser Pro Thr Glu Leu Ile Ala Val Glu Gly Thr Glu Ile Leu Gln
    1910                1915                1920

Asp Phe Gln Asn Lys Thr Asp Gly Gln Val Ser Gly Glu Ala Ile
    1925                1930                1935

Lys Met Phe Pro Thr Ile Lys Thr Pro Glu Ala Gly Thr Val Ile
    1940                1945                1950
```

-continued

Thr Thr Ala Asp Glu Ile Glu Leu Glu Gly Ala Thr Gln Trp Pro
1955             1960                1965

His Ser Thr Ser Ala Ser Ala Thr Tyr Gly Val Glu Ala Gly Val
1970             1975                1980

Val Pro Trp Leu Ser Pro Gln Thr Ser Glu Arg Pro Thr Leu Ser
1985             1990                1995

Ser Ser Pro Glu Ile Asn Pro Glu Thr Gln Ala Ala Leu Ile Arg
2000             2005                2010

Gly Gln Asp Ser Thr Ile Ala Ala Ser Glu Gln Gln Val Ala Ala
2015             2020                2025

Arg Ile Leu Asp Ser Asn Asp Gln Ala Thr Val Asn Pro Val Glu
2030             2035                2040

Phe Asn Thr Glu Val Ala Thr Pro Pro Phe Ser Leu Leu Glu Thr
2045             2050                2055

Ser Asn Glu Thr Asp Phe Leu Ile Gly Ile Asn Glu Glu Ser Val
2060             2065                2070

Glu Gly Thr Ala Ile Tyr Leu Pro Gly Pro Asp Arg Cys Lys Met
2075             2080                2085

Asn Pro Cys Leu Asn Gly Gly Thr Cys Tyr Pro Thr Glu Thr Ser
2090             2095                2100

Tyr Val Cys Thr Cys Val Pro Gly Tyr Ser Gly Asp Gln Cys Glu
2105             2110                2115

Leu Asp Phe Asp Glu Cys His Ser Asn Pro Cys Arg Asn Gly Ala
2120             2125                2130

Thr Cys Val Asp Gly Phe Asn Thr Phe Arg Cys Leu Cys Leu Pro
2135             2140                2145

Ser Tyr Val Gly Ala Leu Cys Glu Gln Asp Thr Glu Thr Cys Asp
2150             2155                2160

Tyr Gly Trp His Lys Phe Gln Gly Gln Cys Tyr Lys Tyr Phe Ala
2165             2170                2175

His Arg Arg Thr Trp Asp Ala Ala Glu Arg Glu Cys Arg Leu Gln
2180             2185                2190

Gly Ala His Leu Thr Ser Ile Leu Ser His Glu Glu Gln Met Phe
2195             2200                2205

Val Asn Arg Val Gly His Asp Tyr Gln Trp Ile Gly Leu Asn Asp
2210             2215                2220

Lys Met Phe Glu His Asp Phe Arg Trp Thr Asp Gly Ser Thr Leu
2225             2230                2235

Gln Tyr Glu Asn Trp Arg Pro Asn Gln Pro Asp Ser Phe Phe Ser
2240             2245                2250

Ala Gly Glu Asp Cys Val Val Ile Ile Trp His Glu Asn Gly Gln
2255             2260                2265

Trp Asn Asp Val Pro Cys Asn Tyr His Leu Thr Tyr Thr Cys Lys
2270             2275                2280

Lys Gly Thr Val Ala Cys Gly Gln Pro Pro Val Val Glu Asn Ala
2285             2290                2295

Lys Thr Phe Gly Lys Met Lys Pro Arg Tyr Glu Ile Asn Ser Leu
2300             2305                2310

Ile Arg Tyr His Cys Lys Asp Gly Phe Ile Gln Arg His Leu Pro
2315             2320                2325

Thr Ile Arg Cys Leu Gly Asn Gly Arg Trp Ala Ile Pro Lys Ile
2330             2335                2340

```
Thr Cys Met Asn Pro Ser Ala Tyr Gln Arg Thr Tyr Ser Met Lys
    2345                2350                2355

Tyr Phe Lys Asn Ser Ser Ser Ala Lys Asp Asn Ser Ile Asn Thr
    2360                2365                2370

Ser Lys His Asp His Arg Trp Ser Arg Arg Trp Gln Glu Ser Arg
    2375                2380                2385

Arg

<210> SEQ ID NO 3
<211> LENGTH: 2390
<212> TYPE: PRT
<213> ORGANISM: Artificial
<220> FEATURE:
<223> OTHER INFORMATION: Full length human versican (V1) (minus signal
      peptide, plus N-terminal methionine)

<400> SEQUENCE: 3

Met Leu His Lys Val Lys Val Gly Lys Ser Pro Pro Val Arg Gly Ser
1               5                   10                  15

Leu Ser Gly Lys Val Ser Leu Pro Cys His Phe Ser Thr Met Pro Thr
                20                  25                  30

Leu Pro Pro Ser Tyr Asn Thr Ser Glu Phe Leu Arg Ile Lys Trp Ser
            35                  40                  45

Lys Ile Glu Val Asp Lys Asn Gly Lys Asp Leu Lys Glu Thr Thr Val
50                  55                  60

Leu Val Ala Gln Asn Gly Asn Ile Lys Ile Gly Gln Asp Tyr Lys Gly
65                  70                  75                  80

Arg Val Ser Val Pro Thr His Pro Glu Ala Val Gly Asp Ala Ser Leu
                85                  90                  95

Thr Val Val Lys Leu Leu Ala Ser Asp Ala Gly Leu Tyr Arg Cys Asp
            100                 105                 110

Val Met Tyr Gly Ile Glu Asp Thr Gln Asp Thr Val Ser Leu Thr Val
        115                 120                 125

Asp Gly Val Val Phe His Tyr Arg Ala Ala Thr Ser Arg Tyr Thr Leu
130                 135                 140

Asn Phe Glu Ala Ala Gln Lys Ala Cys Leu Asp Val Gly Ala Val Ile
145                 150                 155                 160

Ala Thr Pro Glu Gln Leu Phe Ala Ala Tyr Glu Asp Gly Phe Glu Gln
                165                 170                 175

Cys Asp Ala Gly Trp Leu Ala Asp Gln Thr Val Arg Tyr Pro Ile Arg
            180                 185                 190

Ala Pro Arg Val Gly Cys Tyr Gly Asp Lys Met Gly Lys Ala Gly Val
        195                 200                 205

Arg Thr Tyr Gly Phe Arg Ser Pro Gln Glu Thr Tyr Asp Val Tyr Cys
210                 215                 220

Tyr Val Asp His Leu Asp Gly Asp Val Phe His Leu Thr Val Pro Ser
225                 230                 235                 240

Lys Phe Thr Phe Glu Glu Ala Ala Lys Glu Cys Glu Asn Gln Asp Ala
                245                 250                 255

Arg Leu Ala Thr Val Gly Glu Leu Gln Ala Ala Trp Arg Asn Gly Phe
            260                 265                 270

Asp Gln Cys Asp Tyr Gly Trp Leu Ser Asp Ala Ser Val Arg His Pro
        275                 280                 285

Val Thr Val Ala Arg Ala Gln Cys Gly Gly Gly Leu Leu Gly Val Arg
290                 295                 300
```

```
Thr Leu Tyr Arg Phe Glu Asn Gln Thr Gly Phe Pro Pro Asp Ser
305                 310                 315                 320

Arg Phe Asp Ala Tyr Cys Phe Lys Arg Arg Met Ser Asp Leu Ser Val
            325                 330                 335

Ile Gly His Pro Ile Asp Ser Glu Ser Lys Glu Asp Glu Pro Cys Ser
            340                 345                 350

Glu Glu Thr Asp Pro Val His Asp Leu Met Ala Glu Ile Leu Pro Glu
            355                 360                 365

Phe Pro Asp Ile Ile Glu Ile Asp Leu Tyr His Ser Glu Glu Asn Glu
            370                 375                 380

Glu Glu Glu Glu Cys Ala Asn Ala Thr Asp Val Thr Thr Thr Pro
385                 390                 395                 400

Ser Val Gln Tyr Ile Asn Gly Lys His Leu Val Thr Thr Val Pro Lys
            405                 410                 415

Asp Pro Glu Ala Ala Glu Ala Arg Arg Gly Gln Phe Glu Ser Val Ala
            420                 425                 430

Pro Ser Gln Asn Phe Ser Asp Ser Ser Glu Ser Asp Thr His Pro Phe
            435                 440                 445

Val Ile Ala Lys Thr Glu Leu Ser Thr Ala Val Gln Pro Asn Glu Ser
450                 455                 460

Thr Glu Thr Thr Glu Ser Leu Glu Val Thr Trp Lys Pro Glu Thr Tyr
465                 470                 475                 480

Pro Glu Thr Ser Glu His Phe Ser Gly Gly Pro Asp Val Phe Pro
            485                 490                 495

Thr Val Pro Phe His Glu Glu Phe Glu Ser Gly Thr Ala Lys Lys Gly
            500                 505                 510

Ala Glu Ser Val Thr Glu Arg Asp Thr Glu Val Gly His Gln Ala His
            515                 520                 525

Glu His Thr Glu Pro Val Ser Leu Phe Pro Glu Glu Ser Ser Gly Glu
530                 535                 540

Ile Ala Ile Asp Gln Glu Ser Gln Lys Ile Ala Phe Ala Arg Ala Thr
545                 550                 555                 560

Glu Val Thr Phe Gly Glu Glu Val Glu Lys Ser Thr Ser Val Thr Tyr
            565                 570                 575

Thr Pro Thr Ile Val Pro Ser Ser Ala Ser Ala Tyr Val Ser Glu Glu
            580                 585                 590

Glu Ala Val Thr Leu Ile Gly Asn Pro Trp Pro Asp Asp Leu Leu Ser
            595                 600                 605

Thr Lys Glu Ser Trp Val Glu Ala Thr Pro Arg Gln Val Val Glu Leu
            610                 615                 620

Ser Gly Ser Ser Ser Ile Pro Ile Thr Glu Gly Ser Gly Glu Ala Glu
625                 630                 635                 640

Glu Asp Glu Asp Thr Met Phe Thr Met Val Thr Asp Leu Ser Gln Arg
            645                 650                 655

Asn Thr Thr Asp Thr Leu Ile Thr Leu Asp Thr Ser Arg Ile Ile Thr
            660                 665                 670

Glu Ser Phe Phe Glu Val Pro Ala Thr Thr Ile Tyr Pro Val Ser Glu
            675                 680                 685

Gln Pro Ser Ala Lys Val Val Pro Thr Lys Phe Val Ser Glu Thr Asp
            690                 695                 700

Thr Ser Glu Trp Ile Ser Ser Thr Thr Val Glu Glu Lys Lys Arg Lys
705                 710                 715                 720
```

```
Glu Glu Glu Gly Thr Thr Gly Thr Ala Ser Thr Phe Glu Val Tyr Ser
                725                 730                 735

Ser Thr Gln Arg Ser Asp Gln Leu Ile Leu Pro Phe Glu Leu Glu Ser
        740                 745                 750

Pro Asn Val Ala Thr Ser Ser Asp Ser Gly Thr Arg Lys Ser Phe Met
    755                 760                 765

Ser Leu Thr Thr Pro Thr Gln Ser Glu Arg Glu Met Thr Asp Ser Thr
770                 775                 780

Pro Val Phe Thr Glu Thr Asn Thr Leu Glu Asn Leu Gly Ala Gln Thr
785                 790                 795                 800

Thr Glu His Ser Ser Ile His Gln Pro Gly Val Gln Glu Gly Leu Thr
                805                 810                 815

Thr Leu Pro Arg Ser Pro Ala Ser Val Phe Met Glu Gln Gly Ser Gly
            820                 825                 830

Glu Ala Ala Ala Asp Pro Glu Thr Thr Thr Val Ser Ser Phe Ser Leu
        835                 840                 845

Asn Val Glu Tyr Ala Ile Gln Ala Glu Lys Glu Val Ala Gly Thr Leu
    850                 855                 860

Ser Pro His Val Glu Thr Thr Phe Ser Thr Glu Pro Thr Gly Leu Val
865                 870                 875                 880

Leu Ser Thr Val Met Asp Arg Val Val Ala Glu Asn Ile Thr Gln Thr
                885                 890                 895

Ser Arg Glu Ile Val Ile Ser Glu Arg Leu Gly Glu Pro Asn Tyr Gly
            900                 905                 910

Ala Glu Ile Arg Gly Phe Ser Thr Gly Phe Pro Leu Glu Glu Asp Phe
        915                 920                 925

Ser Gly Asp Phe Arg Glu Tyr Ser Thr Val Ser His Pro Ile Ala Lys
    930                 935                 940

Glu Glu Thr Val Met Met Glu Gly Ser Gly Asp Ala Ala Phe Arg Asp
945                 950                 955                 960

Thr Gln Thr Ser Pro Ser Thr Val Pro Thr Ser Val His Ile Ser His
                965                 970                 975

Ile Ser Asp Ser Glu Gly Pro Ser Ser Thr Met Val Ser Thr Ser Ala
            980                 985                 990

Phe Pro Trp Glu Glu Phe Thr Ser  Ser Ala Glu Gly Ser  Gly Glu Gln
        995                 1000                1005

Leu Val  Thr Val Ser Ser  Val Val Pro Val Leu  Pro Ser Ala
    1010                1015                1020

Val Gln  Lys Phe Ser Gly  Thr Ala Ser Ser Ile Ile  Asp Glu Gly
    1025                1030                1035

Leu Gly  Glu Val Gly Thr Val  Asn Glu Ile Asp Arg  Arg Ser Thr
    1040                1045                1050

Ile Leu  Pro Thr Ala Glu Val  Glu Gly Thr Lys Ala  Pro Val Glu
    1055                1060                1065

Lys Glu  Glu Val Lys Val Ser  Gly Thr Val Ser Thr  Asn Phe Pro
    1070                1075                1080

Gln Thr  Ile Glu Pro Ala Lys  Leu Trp Ser Arg Gln  Glu Val Asn
    1085                1090                1095

Pro Val  Arg Gln Glu Ile Glu  Ser Glu Thr Thr Ser  Glu Glu Gln
    1100                1105                1110

Ile Gln  Glu Glu Lys Ser Phe  Glu Ser Pro Gln Asn  Ser Pro Ala
    1115                1120                1125
```

-continued

```
Thr Glu Gln Thr Ile Phe Asp Ser Gln Thr Phe Thr Glu Thr Glu
    1130                1135                1140
Leu Lys Thr Thr Asp Tyr Ser Val Leu Thr Thr Lys Lys Thr Tyr
    1145                1150                1155
Ser Asp Asp Lys Glu Met Lys Glu Glu Asp Thr Ser Leu Val Asn
    1160                1165                1170
Met Ser Thr Pro Asp Pro Asp Ala Asn Gly Leu Glu Ser Tyr Thr
    1175                1180                1185
Thr Leu Pro Glu Ala Thr Glu Lys Ser His Phe Phe Leu Ala Thr
    1190                1195                1200
Ala Leu Val Thr Glu Ser Ile Pro Ala Glu His Val Val Thr Asp
    1205                1210                1215
Ser Pro Ile Lys Lys Glu Glu Ser Thr Lys His Phe Pro Lys Gly
    1220                1225                1230
Met Arg Pro Thr Ile Gln Glu Ser Asp Thr Glu Leu Leu Phe Ser
    1235                1240                1245
Gly Leu Gly Ser Gly Glu Glu Val Leu Pro Thr Leu Pro Thr Glu
    1250                1255                1260
Ser Val Asn Phe Thr Glu Val Glu Gln Ile Asn Asn Thr Leu Tyr
    1265                1270                1275
Pro His Thr Ser Gln Val Glu Ser Thr Ser Ser Asp Lys Ile Glu
    1280                1285                1290
Asp Phe Asn Arg Met Glu Asn Val Ala Lys Glu Val Gly Pro Leu
    1295                1300                1305
Val Ser Gln Thr Asp Ile Phe Glu Gly Ser Gly Ser Val Thr Ser
    1310                1315                1320
Thr Thr Leu Ile Glu Ile Leu Ser Asp Thr Gly Ala Glu Gly Pro
    1325                1330                1335
Thr Val Ala Pro Leu Pro Phe Ser Thr Asp Ile Gly His Pro Gln
    1340                1345                1350
Asn Gln Thr Val Arg Trp Ala Glu Glu Ile Gln Thr Ser Arg Pro
    1355                1360                1365
Gln Thr Ile Thr Glu Gln Asp Ser Asn Lys Asn Ser Ser Thr Ala
    1370                1375                1380
Glu Ile Asn Glu Thr Thr Thr Ser Ser Thr Asp Phe Leu Ala Arg
    1385                1390                1395
Ala Tyr Gly Phe Glu Met Ala Lys Glu Phe Val Thr Ser Ala Pro
    1400                1405                1410
Lys Pro Ser Asp Leu Tyr Tyr Glu Pro Ser Gly Glu Gly Ser Gly
    1415                1420                1425
Glu Val Asp Ile Val Asp Ser Phe His Thr Ser Ala Thr Thr Gln
    1430                1435                1440
Ala Thr Arg Gln Glu Ser Ser Thr Thr Phe Val Ser Asp Gly Ser
    1445                1450                1455
Leu Glu Lys His Pro Glu Val Pro Ser Ala Lys Ala Val Thr Ala
    1460                1465                1470
Asp Gly Phe Pro Thr Val Ser Val Met Leu Pro Leu His Ser Glu
    1475                1480                1485
Gln Asn Lys Ser Ser Pro Asp Pro Thr Ser Thr Leu Ser Asn Thr
    1490                1495                1500
Val Ser Tyr Glu Arg Ser Thr Asp Gly Ser Phe Gln Asp Arg Phe
    1505                1510                1515
```

-continued

Arg Glu Phe Glu Asp Ser Thr Leu Lys Pro Asn Arg Lys Lys Pro
1520                1525                1530

Thr Glu Asn Ile Ile Ile Asp Leu Asp Lys Glu Asp Lys Asp Leu
1535                1540                1545

Ile Leu Thr Ile Thr Glu Ser Thr Ile Leu Glu Ile Leu Pro Glu
1550                1555                1560

Leu Thr Ser Asp Lys Asn Thr Ile Ile Asp Ile Asp His Thr Lys
1565                1570                1575

Pro Val Tyr Glu Asp Ile Leu Gly Met Gln Thr Asp Ile Asp Thr
1580                1585                1590

Glu Val Pro Ser Glu Pro His Asp Ser Asn Asp Glu Ser Asn Asp
1595                1600                1605

Asp Ser Thr Gln Val Gln Glu Ile Tyr Glu Ala Ala Val Asn Leu
1610                1615                1620

Ser Leu Thr Glu Glu Thr Phe Glu Gly Ser Ala Asp Val Leu Ala
1625                1630                1635

Ser Tyr Thr Gln Ala Thr His Asp Glu Ser Met Thr Tyr Glu Asp
1640                1645                1650

Arg Ser Gln Leu Asp His Met Gly Phe His Phe Thr Thr Gly Ile
1655                1660                1665

Pro Ala Pro Ser Thr Glu Thr Glu Leu Asp Val Leu Leu Pro Thr
1670                1675                1680

Ala Thr Ser Leu Pro Ile Pro Arg Lys Ser Ala Thr Val Ile Pro
1685                1690                1695

Glu Ile Glu Gly Ile Lys Ala Glu Ala Lys Ala Leu Asp Asp Met
1700                1705                1710

Phe Glu Ser Ser Thr Leu Ser Asp Gly Gln Ala Ile Ala Asp Gln
1715                1720                1725

Ser Glu Ile Ile Pro Thr Leu Gly Gln Phe Glu Arg Thr Gln Glu
1730                1735                1740

Glu Tyr Glu Asp Lys Lys His Ala Gly Pro Ser Phe Gln Pro Glu
1745                1750                1755

Phe Ser Ser Gly Ala Glu Glu Ala Leu Val Asp His Thr Pro Tyr
1760                1765                1770

Leu Ser Ile Ala Thr Thr His Leu Met Asp Gln Ser Val Thr Glu
1775                1780                1785

Val Pro Asp Val Met Glu Gly Ser Asn Pro Pro Tyr Tyr Thr Asp
1790                1795                1800

Thr Thr Leu Ala Val Ser Thr Phe Ala Lys Leu Ser Ser Gln Thr
1805                1810                1815

Pro Ser Ser Pro Leu Thr Ile Tyr Ser Gly Ser Glu Ala Ser Gly
1820                1825                1830

His Thr Glu Ile Pro Gln Pro Ser Ala Leu Pro Gly Ile Asp Val
1835                1840                1845

Gly Ser Ser Val Met Ser Pro Gln Asp Ser Phe Lys Glu Ile His
1850                1855                1860

Val Asn Ile Glu Ala Thr Phe Lys Pro Ser Ser Glu Glu Tyr Leu
1865                1870                1875

His Ile Thr Glu Pro Pro Ser Leu Ser Pro Asp Thr Lys Leu Glu
1880                1885                1890

Pro Ser Glu Asp Asp Gly Lys Pro Glu Leu Leu Glu Glu Met Glu
1895                1900                1905

```
Ala Ser Pro Thr Glu Leu Ile Ala Val Glu Gly Thr Glu Ile Leu
1910                1915                1920

Gln Asp Phe Gln Asn Lys Thr Asp Gly Gln Val Ser Gly Glu Ala
1925                1930                1935

Ile Lys Met Phe Pro Thr Ile Lys Thr Pro Glu Ala Gly Thr Val
1940                1945                1950

Ile Thr Thr Ala Asp Glu Ile Glu Leu Glu Gly Ala Thr Gln Trp
1955                1960                1965

Pro His Ser Thr Ser Ala Ser Ala Thr Tyr Gly Val Glu Ala Gly
1970                1975                1980

Val Val Pro Trp Leu Ser Pro Gln Thr Ser Glu Arg Pro Thr Leu
1985                1990                1995

Ser Ser Ser Pro Glu Ile Asn Pro Glu Thr Gln Ala Ala Leu Ile
2000                2005                2010

Arg Gly Gln Asp Ser Thr Ile Ala Ala Ser Glu Gln Gln Val Ala
2015                2020                2025

Ala Arg Ile Leu Asp Ser Asn Asp Gln Ala Thr Val Asn Pro Val
2030                2035                2040

Glu Phe Asn Thr Glu Val Ala Thr Pro Pro Phe Ser Leu Leu Glu
2045                2050                2055

Thr Ser Asn Glu Thr Asp Phe Leu Ile Gly Ile Asn Glu Glu Ser
2060                2065                2070

Val Glu Gly Thr Ala Ile Tyr Leu Pro Gly Pro Asp Arg Cys Lys
2075                2080                2085

Met Asn Pro Cys Leu Asn Gly Gly Thr Cys Tyr Pro Thr Glu Thr
2090                2095                2100

Ser Tyr Val Cys Thr Cys Val Pro Gly Tyr Ser Gly Asp Gln Cys
2105                2110                2115

Glu Leu Asp Phe Asp Glu Cys His Ser Asn Pro Cys Arg Asn Gly
2120                2125                2130

Ala Thr Cys Val Asp Gly Phe Asn Thr Phe Arg Cys Leu Cys Leu
2135                2140                2145

Pro Ser Tyr Val Gly Ala Leu Cys Glu Gln Asp Thr Glu Thr Cys
2150                2155                2160

Asp Tyr Gly Trp His Lys Phe Gln Gly Gln Cys Tyr Lys Tyr Phe
2165                2170                2175

Ala His Arg Arg Thr Trp Asp Ala Ala Glu Arg Glu Cys Arg Leu
2180                2185                2190

Gln Gly Ala His Leu Thr Ser Ile Leu Ser His Glu Glu Gln Met
2195                2200                2205

Phe Val Asn Arg Val Gly His Asp Tyr Gln Trp Ile Gly Leu Asn
2210                2215                2220

Asp Lys Met Phe Glu His Asp Phe Arg Trp Thr Asp Gly Ser Thr
2225                2230                2235

Leu Gln Tyr Glu Asn Trp Arg Pro Asn Gln Pro Asp Ser Phe Phe
2240                2245                2250

Ser Ala Gly Glu Asp Cys Val Val Ile Ile Trp His Glu Asn Gly
2255                2260                2265

Gln Trp Asn Asp Val Pro Cys Asn Tyr His Leu Thr Tyr Thr Cys
2270                2275                2280

Lys Lys Gly Thr Val Ala Cys Gly Gln Pro Pro Val Val Glu Asn
2285                2290                2295
```

```
Ala Lys Thr Phe Gly Lys Met Lys Pro Arg Tyr Glu Ile Asn Ser
    2300                2305                2310

Leu Ile Arg Tyr His Cys Lys Asp Gly Phe Ile Gln Arg His Leu
    2315                2320                2325

Pro Thr Ile Arg Cys Leu Gly Asn Gly Arg Trp Ala Ile Pro Lys
    2330                2335                2340

Ile Thr Cys Met Asn Pro Ser Ala Tyr Gln Arg Thr Tyr Ser Met
    2345                2350                2355

Lys Tyr Phe Lys Asn Ser Ser Ala Lys Asp Asn Ser Ile Asn
    2360                2365                2370

Thr Ser Lys His Asp His Arg Trp Ser Arg Arg Trp Gln Glu Ser
    2375                2380                2385

Arg Arg
    2390

<210> SEQ ID NO 4
<211> LENGTH: 1968
<212> TYPE: PRT
<213> ORGANISM: Homo sapiens

<400> SEQUENCE: 4

Ala Arg Arg Gly Gln Phe Glu Ser Val Ala Pro Ser Gln Asn Phe Ser
1               5                   10                  15

Asp Ser Ser Glu Ser Asp Thr His Pro Phe Val Ile Ala Lys Thr Glu
                20                  25                  30

Leu Ser Thr Ala Val Gln Pro Asn Glu Ser Thr Glu Thr Thr Glu Ser
            35                  40                  45

Leu Glu Val Thr Trp Lys Pro Glu Thr Tyr Pro Glu Thr Ser Glu His
        50                  55                  60

Phe Ser Gly Gly Glu Pro Asp Val Phe Pro Thr Val Pro Phe His Glu
65                  70                  75                  80

Glu Phe Glu Ser Gly Thr Ala Lys Lys Gly Ala Glu Ser Val Thr Glu
                85                  90                  95

Arg Asp Thr Glu Val Gly His Gln Ala His Glu His Thr Glu Pro Val
            100                 105                 110

Ser Leu Phe Pro Glu Glu Ser Ser Gly Glu Ile Ala Ile Asp Gln Glu
        115                 120                 125

Ser Gln Lys Ile Ala Phe Ala Arg Ala Thr Glu Val Thr Phe Gly Glu
    130                 135                 140

Glu Val Glu Lys Ser Thr Ser Val Thr Tyr Thr Pro Thr Ile Val Pro
145                 150                 155                 160

Ser Ser Ala Ser Ala Tyr Val Ser Glu Glu Glu Ala Val Thr Leu Ile
                165                 170                 175

Gly Asn Pro Trp Pro Asp Asp Leu Leu Ser Thr Lys Glu Ser Trp Val
            180                 185                 190

Glu Ala Thr Pro Arg Gln Val Val Glu Leu Ser Gly Ser Ser Ser Ile
        195                 200                 205

Pro Ile Thr Glu Gly Ser Gly Glu Ala Glu Glu Asp Glu Asp Thr Met
    210                 215                 220

Phe Thr Met Val Thr Asp Leu Ser Gln Arg Asn Thr Thr Asp Thr Leu
225                 230                 235                 240

Ile Thr Leu Asp Thr Ser Arg Ile Ile Thr Glu Ser Phe Phe Glu Val
                245                 250                 255

Pro Ala Thr Thr Ile Tyr Pro Val Ser Glu Gln Pro Ser Ala Lys Val
            260                 265                 270
```

-continued

```
Val Pro Thr Lys Phe Val Ser Glu Thr Asp Thr Ser Glu Trp Ile Ser
            275                 280                 285

Ser Thr Thr Val Glu Glu Lys Lys Arg Lys Glu Glu Glu Gly Thr Thr
    290                 295                 300

Gly Thr Ala Ser Thr Phe Glu Val Tyr Ser Ser Thr Gln Arg Ser Asp
305                 310                 315                 320

Gln Leu Ile Leu Pro Phe Glu Leu Glu Ser Pro Asn Val Ala Thr Ser
                325                 330                 335

Ser Asp Ser Gly Thr Arg Lys Ser Phe Met Ser Leu Thr Thr Pro Thr
            340                 345                 350

Gln Ser Glu Arg Glu Met Thr Asp Ser Thr Pro Val Phe Thr Glu Thr
            355                 360                 365

Asn Thr Leu Glu Asn Leu Gly Ala Gln Thr Thr Glu His Ser Ser Ile
    370                 375                 380

His Gln Pro Gly Val Gln Glu Gly Leu Thr Thr Leu Pro Arg Ser Pro
385                 390                 395                 400

Ala Ser Val Phe Met Glu Gln Gly Ser Gly Glu Ala Ala Ala Asp Pro
                405                 410                 415

Glu Thr Thr Thr Val Ser Ser Phe Ser Leu Asn Val Glu Tyr Ala Ile
            420                 425                 430

Gln Ala Glu Lys Glu Val Ala Gly Thr Leu Ser Pro His Val Glu Thr
    435                 440                 445

Thr Phe Ser Thr Glu Pro Thr Gly Leu Val Leu Ser Thr Val Met Asp
    450                 455                 460

Arg Val Ala Glu Asn Ile Thr Gln Thr Ser Arg Glu Ile Val Ile
465                 470                 475                 480

Ser Glu Arg Leu Gly Glu Pro Asn Tyr Gly Ala Glu Ile Arg Gly Phe
                485                 490                 495

Ser Thr Gly Phe Pro Leu Glu Glu Asp Phe Ser Gly Asp Phe Arg Glu
            500                 505                 510

Tyr Ser Thr Val Ser His Pro Ile Ala Lys Glu Glu Thr Val Met Met
    515                 520                 525

Glu Gly Ser Gly Asp Ala Ala Phe Arg Asp Thr Gln Thr Ser Pro Ser
    530                 535                 540

Thr Val Pro Thr Ser Val His Ile Ser His Ile Ser Asp Ser Glu Gly
545                 550                 555                 560

Pro Ser Ser Thr Met Val Ser Thr Ser Ala Phe Pro Trp Glu Glu Phe
                565                 570                 575

Thr Ser Ser Ala Glu Gly Ser Gly Glu Gln Leu Val Thr Val Ser Ser
            580                 585                 590

Ser Val Val Pro Val Leu Pro Ser Ala Val Gln Lys Phe Ser Gly Thr
    595                 600                 605

Ala Ser Ser Ile Ile Asp Glu Gly Leu Gly Glu Val Gly Thr Val Asn
    610                 615                 620

Glu Ile Asp Arg Arg Ser Thr Ile Leu Pro Thr Ala Glu Val Glu Gly
625                 630                 635                 640

Thr Lys Ala Pro Val Glu Lys Glu Glu Val Lys Val Ser Gly Thr Val
                645                 650                 655

Ser Thr Asn Phe Pro Gln Thr Ile Glu Pro Ala Lys Leu Trp Ser Arg
            660                 665                 670

Gln Glu Val Asn Pro Val Arg Gln Glu Ile Glu Ser Glu Thr Thr Ser
    675                 680                 685
```

```
Glu Glu Gln Ile Gln Glu Glu Lys Ser Phe Glu Ser Pro Gln Asn Ser
690                 695                 700

Pro Ala Thr Glu Gln Thr Ile Phe Asp Ser Gln Thr Phe Thr Glu Thr
705                 710                 715                 720

Glu Leu Lys Thr Thr Asp Tyr Ser Val Leu Thr Thr Lys Lys Thr Tyr
            725                 730                 735

Ser Asp Asp Lys Glu Met Lys Glu Glu Asp Thr Ser Leu Val Asn Met
                740                 745                 750

Ser Thr Pro Asp Pro Asp Ala Asn Gly Leu Glu Ser Tyr Thr Thr Leu
        755                 760                 765

Pro Glu Ala Thr Glu Lys Ser His Phe Phe Leu Ala Thr Ala Leu Val
770                 775                 780

Thr Glu Ser Ile Pro Ala Glu His Val Val Thr Asp Ser Pro Ile Lys
785                 790                 795                 800

Lys Glu Glu Ser Thr Lys His Phe Pro Lys Gly Met Arg Pro Thr Ile
            805                 810                 815

Gln Glu Ser Asp Thr Glu Leu Leu Phe Ser Gly Leu Gly Ser Gly Glu
                820                 825                 830

Glu Val Leu Pro Thr Leu Pro Thr Glu Ser Val Asn Phe Thr Glu Val
        835                 840                 845

Glu Gln Ile Asn Asn Thr Leu Tyr Pro His Thr Ser Gln Val Glu Ser
850                 855                 860

Thr Ser Ser Asp Lys Ile Glu Asp Phe Asn Arg Met Glu Asn Val Ala
865                 870                 875                 880

Lys Glu Val Gly Pro Leu Val Ser Gln Thr Asp Ile Phe Glu Gly Ser
            885                 890                 895

Gly Ser Val Thr Ser Thr Thr Leu Ile Glu Ile Leu Ser Asp Thr Gly
                900                 905                 910

Ala Glu Gly Pro Thr Val Ala Pro Leu Pro Phe Ser Thr Asp Ile Gly
        915                 920                 925

His Pro Gln Asn Gln Thr Val Arg Trp Ala Glu Glu Ile Gln Thr Ser
930                 935                 940

Arg Pro Gln Thr Ile Thr Glu Gln Asp Ser Asn Lys Asn Ser Ser Thr
945                 950                 955                 960

Ala Glu Ile Asn Glu Thr Thr Thr Ser Ser Thr Asp Phe Leu Ala Arg
            965                 970                 975

Ala Tyr Gly Phe Glu Met Ala Lys Glu Phe Val Thr Ser Ala Pro Lys
                980                 985                 990

Pro Ser Asp Leu Tyr Tyr Glu Pro  Ser Gly Glu Gly Ser  Gly Glu Val
        995                 1000                1005

Asp Ile  Val Asp Ser Phe His  Thr Ser Ala Thr Thr  Gln Ala Thr
    1010                1015                1020

Arg Gln  Glu Ser Ser Thr Thr  Phe Val Ser Asp Gly  Ser Leu Glu
    1025                1030                1035

Lys His  Pro Glu Val Pro Ser  Ala Lys Ala Val Thr  Ala Asp Gly
    1040                1045                1050

Phe Pro  Thr Val Ser Val Met  Leu Pro Leu His Ser  Glu Gln Asn
    1055                1060                1065

Lys Ser  Ser Pro Asp Pro Thr  Ser Thr Leu Ser Asn  Thr Val Ser
    1070                1075                1080

Tyr Glu  Arg Ser Thr Asp Gly  Ser Phe Gln Asp Arg  Phe Arg Glu
    1085                1090                1095
```

```
Phe Glu Asp Ser Thr Leu Lys Pro Asn Arg Lys Lys Pro Thr Glu
1100                1105                1110

Asn Ile Ile Ile Asp Leu Asp Lys Glu Asp Lys Asp Leu Ile Leu
1115                1120                1125

Thr Ile Thr Glu Ser Thr Ile Leu Glu Ile Leu Pro Glu Leu Thr
1130                1135                1140

Ser Asp Lys Asn Thr Ile Ile Asp Ile Asp His Thr Lys Pro Val
1145                1150                1155

Tyr Glu Asp Ile Leu Gly Met Gln Thr Asp Ile Asp Thr Glu Val
1160                1165                1170

Pro Ser Glu Pro His Asp Ser Asn Asp Glu Ser Asn Asp Asp Ser
1175                1180                1185

Thr Gln Val Gln Glu Ile Tyr Glu Ala Ala Val Asn Leu Ser Leu
1190                1195                1200

Thr Glu Glu Thr Phe Glu Gly Ser Ala Asp Val Leu Ala Ser Tyr
1205                1210                1215

Thr Gln Ala Thr His Asp Glu Ser Met Thr Tyr Glu Asp Arg Ser
1220                1225                1230

Gln Leu Asp His Met Gly Phe His Phe Thr Thr Gly Ile Pro Ala
1235                1240                1245

Pro Ser Thr Glu Thr Glu Leu Asp Val Leu Leu Pro Thr Ala Thr
1250                1255                1260

Ser Leu Pro Ile Pro Arg Lys Ser Ala Thr Val Ile Pro Glu Ile
1265                1270                1275

Glu Gly Ile Lys Ala Glu Ala Lys Ala Leu Asp Asp Met Phe Glu
1280                1285                1290

Ser Ser Thr Leu Ser Asp Gly Gln Ala Ile Ala Asp Gln Ser Glu
1295                1300                1305

Ile Ile Pro Thr Leu Gly Gln Phe Glu Arg Thr Gln Glu Glu Tyr
1310                1315                1320

Glu Asp Lys Lys His Ala Gly Pro Ser Phe Gln Pro Glu Phe Ser
1325                1330                1335

Ser Gly Ala Glu Glu Ala Leu Val Asp His Thr Pro Tyr Leu Ser
1340                1345                1350

Ile Ala Thr Thr His Leu Met Asp Gln Ser Val Thr Glu Val Pro
1355                1360                1365

Asp Val Met Glu Gly Ser Asn Pro Pro Tyr Tyr Thr Asp Thr Thr
1370                1375                1380

Leu Ala Val Ser Thr Phe Ala Lys Leu Ser Ser Gln Thr Pro Ser
1385                1390                1395

Ser Pro Leu Thr Ile Tyr Ser Gly Ser Glu Ala Ser Gly His Thr
1400                1405                1410

Glu Ile Pro Gln Pro Ser Ala Leu Pro Gly Ile Asp Val Gly Ser
1415                1420                1425

Ser Val Met Ser Pro Gln Asp Ser Phe Lys Glu Ile His Val Asn
1430                1435                1440

Ile Glu Ala Thr Phe Lys Pro Ser Ser Glu Glu Tyr Leu His Ile
1445                1450                1455

Thr Glu Pro Pro Ser Leu Ser Pro Asp Thr Lys Leu Glu Pro Ser
1460                1465                1470

Glu Asp Asp Gly Lys Pro Glu Leu Leu Glu Glu Met Glu Ala Ser
1475                1480                1485
```

```
Pro Thr Glu Leu Ile Ala Val Glu Gly Thr Glu Ile Leu Gln Asp
1490                1495                1500

Phe Gln Asn Lys Thr Asp Gly Gln Val Ser Gly Glu Ala Ile Lys
1505                1510                1515

Met Phe Pro Thr Ile Lys Thr Pro Glu Ala Gly Thr Val Ile Thr
1520                1525                1530

Thr Ala Asp Glu Ile Glu Leu Glu Gly Ala Thr Gln Trp Pro His
1535                1540                1545

Ser Thr Ser Ala Ser Ala Thr Tyr Gly Val Glu Ala Gly Val Val
1550                1555                1560

Pro Trp Leu Ser Pro Gln Thr Ser Glu Arg Pro Thr Leu Ser Ser
1565                1570                1575

Ser Pro Glu Ile Asn Pro Glu Thr Gln Ala Ala Leu Ile Arg Gly
1580                1585                1590

Gln Asp Ser Thr Ile Ala Ala Ser Glu Gln Gln Val Ala Ala Arg
1595                1600                1605

Ile Leu Asp Ser Asn Asp Gln Ala Thr Val Asn Pro Val Glu Phe
1610                1615                1620

Asn Thr Glu Val Ala Thr Pro Pro Phe Ser Leu Leu Glu Thr Ser
1625                1630                1635

Asn Glu Thr Asp Phe Leu Ile Gly Ile Asn Glu Glu Ser Val Glu
1640                1645                1650

Gly Thr Ala Ile Tyr Leu Pro Gly Pro Asp Arg Cys Lys Met Asn
1655                1660                1665

Pro Cys Leu Asn Gly Gly Thr Cys Tyr Pro Thr Glu Thr Ser Tyr
1670                1675                1680

Val Cys Thr Cys Val Pro Gly Tyr Ser Gly Asp Gln Cys Glu Leu
1685                1690                1695

Asp Phe Asp Glu Cys His Ser Asn Pro Cys Arg Asn Gly Ala Thr
1700                1705                1710

Cys Val Asp Gly Phe Asn Thr Phe Arg Cys Leu Cys Leu Pro Ser
1715                1720                1725

Tyr Val Gly Ala Leu Cys Glu Gln Asp Thr Glu Thr Cys Asp Tyr
1730                1735                1740

Gly Trp His Lys Phe Gln Gly Gln Cys Tyr Lys Tyr Phe Ala His
1745                1750                1755

Arg Arg Thr Trp Asp Ala Ala Glu Arg Glu Cys Arg Leu Gln Gly
1760                1765                1770

Ala His Leu Thr Ser Ile Leu Ser His Glu Glu Gln Met Phe Val
1775                1780                1785

Asn Arg Val Gly His Asp Tyr Gln Trp Ile Gly Leu Asn Asp Lys
1790                1795                1800

Met Phe Glu His Asp Phe Arg Trp Thr Asp Gly Ser Thr Leu Gln
1805                1810                1815

Tyr Glu Asn Trp Arg Pro Asn Gln Pro Asp Ser Phe Phe Ser Ala
1820                1825                1830

Gly Glu Asp Cys Val Val Ile Ile Trp His Glu Asn Gly Gln Trp
1835                1840                1845

Asn Asp Val Pro Cys Asn Tyr His Leu Thr Tyr Thr Cys Lys Lys
1850                1855                1860

Gly Thr Val Ala Cys Gly Gln Pro Pro Val Val Glu Asn Ala Lys
1865                1870                1875
```

-continued

```
Thr Phe Gly Lys Met Lys Pro Arg Tyr Glu Ile Asn Ser Leu Ile
    1880                1885                1890

Arg Tyr His Cys Lys Asp Gly Phe Ile Gln Arg His Leu Pro Thr
    1895                1900                1905

Ile Arg Cys Leu Gly Asn Gly Arg Trp Ala Ile Pro Lys Ile Thr
    1910                1915                1920

Cys Met Asn Pro Ser Ala Tyr Gln Arg Thr Tyr Ser Met Lys Tyr
    1925                1930                1935

Phe Lys Asn Ser Ser Ser Ala Lys Asp Asn Ser Ile Asn Thr Ser
    1940                1945                1950

Lys His Asp His Arg Trp Ser Arg Arg Trp Gln Glu Ser Arg Arg
    1955                1960                1965

<210> SEQ ID NO 5
<211> LENGTH: 441
<212> TYPE: PRT
<213> ORGANISM: Homo sapiens

<400> SEQUENCE: 5

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
                20                  25                  30

Arg Gly Ser Leu Ser Gly Lys Val Ser Leu Pro Cys His Phe Ser Thr
            35                  40                  45

Met Pro Thr Leu Pro Pro Ser Tyr Asn Thr Ser Glu Phe Leu Arg Ile
        50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285
```

```
Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Arg Met Ser Asp
                340                 345                 350

Leu Ser Val Ile Gly His Pro Ile Asp Ser Glu Ser Lys Glu Asp Glu
                355                 360                 365

Pro Cys Ser Glu Glu Thr Asp Pro Val His Asp Leu Met Ala Glu Ile
370                 375                 380

Leu Pro Glu Phe Pro Asp Ile Ile Glu Ile Asp Leu Tyr His Ser Glu
385                 390                 395                 400

Glu Asn Glu Glu Glu Glu Glu Cys Ala Asn Ala Thr Asp Val Thr
                405                 410                 415

Thr Thr Pro Ser Val Gln Tyr Ile Asn Gly Lys His Leu Val Thr Thr
                420                 425                 430

Val Pro Lys Asp Pro Glu Ala Ala Glu
                435                 440

<210> SEQ ID NO 6
<211> LENGTH: 421
<212> TYPE: PRT
<213> ORGANISM: Homo sapiens

<400> SEQUENCE: 6

Leu His Lys Val Lys Val Gly Lys Ser Pro Pro Val Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
            35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110

Met Tyr Gly Ile Glu Asp Thr Gln Asp Thr Val Ser Leu Thr Val Asp
            115                 120                 125

Gly Val Val Phe His Tyr Arg Ala Ala Thr Ser Arg Tyr Thr Leu Asn
            130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
            180                 185                 190

Pro Arg Val Gly Cys Tyr Gly Asp Lys Met Gly Lys Ala Gly Val Arg
            195                 200                 205

Thr Tyr Gly Phe Arg Ser Pro Gln Glu Thr Tyr Asp Val Tyr Cys Tyr
            210                 215                 220
```

-continued

```
Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
            245                 250                 255

Leu Ala Thr Val Gly Glu Leu Gln Ala Ala Trp Arg Asn Gly Phe Asp
        260                 265                 270

Gln Cys Asp Tyr Gly Trp Leu Ser Asp Ala Ser Val Arg His Pro Val
    275                 280                 285

Thr Val Ala Arg Ala Gln Cys Gly Gly Gly Leu Leu Gly Val Arg Thr
290                 295                 300

Leu Tyr Arg Phe Glu Asn Gln Thr Gly Phe Pro Pro Pro Asp Ser Arg
305                 310                 315                 320

Phe Asp Ala Tyr Cys Phe Lys Arg Arg Met Ser Asp Leu Ser Val Ile
            325                 330                 335

Gly His Pro Ile Asp Ser Glu Ser Lys Glu Asp Glu Pro Cys Ser Glu
        340                 345                 350

Glu Thr Asp Pro Val His Asp Leu Met Ala Glu Ile Leu Pro Glu Phe
    355                 360                 365

Pro Asp Ile Ile Glu Ile Asp Leu Tyr His Ser Glu Glu Asn Glu Glu
370                 375                 380

Glu Glu Glu Glu Cys Ala Asn Ala Thr Asp Val Thr Thr Thr Pro Ser
385                 390                 395                 400

Val Gln Tyr Ile Asn Gly Lys His Leu Val Thr Val Pro Lys Asp
            405                 410                 415

Pro Glu Ala Ala Glu
            420
```

<210> SEQ ID NO 7
<211> LENGTH: 422
<212> TYPE: PRT
<213> ORGANISM: Artificial
<220> FEATURE:
<223> OTHER INFORMATION: Full length human versikine (minus signal
      peptide, plus N-terminal methionine)

<400> SEQUENCE: 7

```
Met Leu His Lys Val Lys Val Gly Lys Ser Pro Pro Val Arg Gly Ser
1               5                   10                  15

Leu Ser Gly Lys Val Ser Leu Pro Cys His Phe Ser Thr Met Pro Thr
            20                  25                  30

Leu Pro Pro Ser Tyr Asn Thr Ser Glu Phe Leu Arg Ile Lys Trp Ser
        35                  40                  45

Lys Ile Glu Val Asp Lys Asn Gly Lys Asp Leu Lys Glu Thr Thr Val
50                  55                  60

Leu Val Ala Gln Asn Gly Asn Ile Lys Ile Gly Gln Asp Tyr Lys Gly
65                  70                  75                  80

Arg Val Ser Val Pro Thr His Pro Glu Ala Val Gly Asp Ala Ser Leu
                85                  90                  95

Thr Val Val Lys Leu Leu Ala Ser Asp Ala Gly Leu Tyr Arg Cys Asp
            100                 105                 110

Val Met Tyr Gly Ile Glu Asp Thr Gln Asp Thr Val Ser Leu Thr Val
        115                 120                 125

Asp Gly Val Val Phe His Tyr Arg Ala Ala Thr Ser Arg Tyr Thr Leu
    130                 135                 140

Asn Phe Glu Ala Ala Gln Lys Ala Cys Leu Asp Val Gly Ala Val Ile
145                 150                 155                 160
```

Ala Thr Pro Glu Gln Leu Phe Ala Ala Tyr Glu Asp Gly Phe Glu Gln
            165                 170                 175

Cys Asp Ala Gly Trp Leu Ala Asp Gln Thr Val Arg Tyr Pro Ile Arg
        180                 185                 190

Ala Pro Arg Val Gly Cys Tyr Gly Asp Lys Met Gly Lys Ala Gly Val
        195                 200                 205

Arg Thr Tyr Gly Phe Arg Ser Pro Gln Glu Thr Tyr Asp Val Tyr Cys
        210                 215                 220

Tyr Val Asp His Leu Asp Gly Asp Val Phe His Leu Thr Val Pro Ser
225                 230                 235                 240

Lys Phe Thr Phe Glu Glu Ala Ala Lys Glu Cys Glu Asn Gln Asp Ala
            245                 250                 255

Arg Leu Ala Thr Val Gly Glu Leu Gln Ala Ala Trp Arg Asn Gly Phe
        260                 265                 270

Asp Gln Cys Asp Tyr Gly Trp Leu Ser Asp Ala Ser Val Arg His Pro
        275                 280                 285

Val Thr Val Ala Arg Ala Gln Cys Gly Gly Gly Leu Leu Gly Val Arg
        290                 295                 300

Thr Leu Tyr Arg Phe Glu Asn Gln Thr Gly Phe Pro Pro Pro Asp Ser
305                 310                 315                 320

Arg Phe Asp Ala Tyr Cys Phe Lys Arg Arg Met Ser Asp Leu Ser Val
            325                 330                 335

Ile Gly His Pro Ile Asp Ser Glu Ser Lys Glu Asp Glu Pro Cys Ser
        340                 345                 350

Glu Glu Thr Asp Pro Val His Asp Leu Met Ala Glu Ile Leu Pro Glu
        355                 360                 365

Phe Pro Asp Ile Ile Glu Ile Asp Leu Tyr His Ser Glu Glu Asn Glu
        370                 375                 380

Glu Glu Glu Glu Glu Cys Ala Asn Ala Thr Asp Val Thr Thr Thr Pro
385                 390                 395                 400

Ser Val Gln Tyr Ile Asn Gly Lys His Leu Val Thr Thr Val Pro Lys
            405                 410                 415

Asp Pro Glu Ala Ala Glu
            420

<210> SEQ ID NO 8
<211> LENGTH: 146
<212> TYPE: PRT
<213> ORGANISM: Homo sapiens

<400> SEQUENCE: 8

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
            85                  90                  95

Tyr Lys Gly Arg Val Ser Val Pro Thr His Pro Glu Ala Val Gly Asp
            100                 105                 110

-continued

Ala Ser Leu Thr Val Val Lys Leu Leu Ala Ser Asp Ala Gly Leu Tyr
            115                 120                 125

Arg Cys Asp Val Met Tyr Gly Ile Glu Asp Thr Gln Asp Thr Val Ser
        130                 135                 140

Leu Thr
145

<210> SEQ ID NO 9
<211> LENGTH: 126
<212> TYPE: PRT
<213> ORGANISM: Homo sapiens

<400> SEQUENCE: 9

Leu His Lys Val Lys Val Gly Lys Ser Pro Pro Val Arg Gly Ser Leu
1               5                   10                  15

Ser Gly Lys Val Ser Leu Pro Cys His Phe Ser Thr Met Pro Thr Leu
            20                  25                  30

Pro Pro Ser Tyr Asn Thr Ser Glu Phe Leu Arg Ile Lys Trp Ser Lys
        35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110

Met Tyr Gly Ile Glu Asp Thr Gln Asp Thr Val Ser Leu Thr
        115                 120                 125

<210> SEQ ID NO 10
<211> LENGTH: 127
<212> TYPE: PRT
<213> ORGANISM: Artificial
<220> FEATURE:
<223> OTHER INFORMATION: Ig-like domain of human versikine (minus signal
      peptide, plus N-terminal methionine)

<400> SEQUENCE: 10

Met Leu His Lys Val Lys Val Gly Lys Ser Pro Pro Val Arg Gly Ser
1               5                   10                  15

Leu Ser Gly Lys Val Ser Leu Pro Cys His Phe Ser Thr Met Pro Thr
            20                  25                  30

Leu Pro Pro Ser Tyr Asn Thr Ser Glu Phe Leu Arg Ile Lys Trp Ser
        35                  40                  45

Lys Ile Glu Val Asp Lys Asn Gly Lys Asp Leu Lys Glu Thr Thr Val
    50                  55                  60

Leu Val Ala Gln Asn Gly Asn Ile Lys Ile Gly Gln Asp Tyr Lys Gly
65                  70                  75                  80

Arg Val Ser Val Pro Thr His Pro Glu Ala Val Gly Asp Ala Ser Leu
                85                  90                  95

Thr Val Val Lys Leu Leu Ala Ser Asp Ala Gly Leu Tyr Arg Cys Asp
            100                 105                 110

Val Met Tyr Gly Ile Glu Asp Thr Gln Asp Thr Val Ser Leu Thr
        115                 120                 125

<210> SEQ ID NO 11
<211> LENGTH: 96
<212> TYPE: PRT
<213> ORGANISM: Homo sapiens

<400> SEQUENCE: 11

Val Val Phe His Tyr Arg Ala Ala Thr Ser Arg Tyr Thr Leu Asn Phe
1               5                   10                  15

Glu Ala Ala Gln Lys Ala Cys Leu Asp Val Gly Ala Val Ile Ala Thr
            20                  25                  30

Pro Glu Gln Leu Phe Ala Ala Tyr Glu Asp Gly Phe Glu Gln Cys Asp
        35                  40                  45

Ala Gly Trp Leu Ala Asp Gln Thr Val Arg Tyr Pro Ile Arg Ala Pro
50                  55                  60

Arg Val Gly Cys Tyr Gly Asp Lys Met Gly Lys Ala Gly Val Arg Thr
65                  70                  75                  80

Tyr Gly Phe Arg Ser Pro Gln Glu Thr Tyr Asp Val Tyr Cys Tyr Val
                85                  90                  95

<210> SEQ ID NO 12
<211> LENGTH: 97
<212> TYPE: PRT
<213> ORGANISM: Artificial
<220> FEATURE:
<223> OTHER INFORMATION: Linker domain 1 of human versikine (plus N-
      terminal methionine)

<400> SEQUENCE: 12

Met Val Val Phe His Tyr Arg Ala Ala Thr Ser Arg Tyr Thr Leu Asn
1               5                   10                  15

Phe Glu Ala Ala Gln Lys Ala Cys Leu Asp Val Gly Ala Val Ile Ala
            20                  25                  30

Thr Pro Glu Gln Leu Phe Ala Ala Tyr Glu Asp Gly Phe Glu Gln Cys
        35                  40                  45

Asp Ala Gly Trp Leu Ala Asp Gln Thr Val Arg Tyr Pro Ile Arg Ala
    50                  55                  60

Pro Arg Val Gly Cys Tyr Gly Asp Lys Met Gly Lys Ala Gly Val Arg
65                  70                  75                  80

Thr Tyr Gly Phe Arg Ser Pro Gln Glu Thr Tyr Asp Val Tyr Cys Tyr
                85                  90                  95

Val

<210> SEQ ID NO 13
<211> LENGTH: 97
<212> TYPE: PRT
<213> ORGANISM: Homo sapiens

<400> SEQUENCE: 13

Asp Val Phe His Leu Thr Val Pro Ser Lys Phe Thr Phe Glu Glu Ala
1               5                   10                  15

Ala Lys Glu Cys Glu Asn Gln Asp Ala Arg Leu Ala Thr Val Gly Glu
            20                  25                  30

Leu Gln Ala Ala Trp Arg Asn Gly Phe Asp Gln Cys Asp Tyr Gly Trp
        35                  40                  45

Leu Ser Asp Ala Ser Val Arg His Pro Val Thr Val Ala Arg Ala Gln
    50                  55                  60

Cys Gly Gly Gly Leu Leu Gly Val Arg Thr Leu Tyr Arg Phe Glu Asn
65                  70                  75                  80

```
Gln Thr Gly Phe Pro Pro Pro Asp Ser Arg Phe Asp Ala Tyr Cys Phe
                85                  90                  95

Lys

<210> SEQ ID NO 14
<211> LENGTH: 98
<212> TYPE: PRT
<213> ORGANISM: Artificial
<220> FEATURE:
<223> OTHER INFORMATION: Linker domain 2 of human versikine (plus N-
      terminal methionine)

<400> SEQUENCE: 14

Met Asp Val Phe His Leu Thr Val Pro Ser Lys Phe Thr Phe Glu Glu
1               5                   10                  15

Ala Ala Lys Glu Cys Glu Asn Gln Asp Ala Arg Leu Ala Thr Val Gly
                20                  25                  30

Glu Leu Gln Ala Ala Trp Arg Asn Gly Phe Asp Gln Cys Asp Tyr Gly
            35                  40                  45

Trp Leu Ser Asp Ala Ser Val Arg His Pro Val Thr Val Ala Arg Ala
    50                  55                  60

Gln Cys Gly Gly Gly Leu Leu Gly Val Arg Thr Leu Tyr Arg Phe Glu
65                  70                  75                  80

Asn Gln Thr Gly Phe Pro Pro Pro Asp Ser Arg Phe Asp Ala Tyr Cys
                85                  90                  95

Phe Lys

<210> SEQ ID NO 15
<211> LENGTH: 93
<212> TYPE: PRT
<213> ORGANISM: Homo sapiens

<400> SEQUENCE: 15

Arg Met Ser Asp Leu Ser Val Ile Gly His Pro Ile Asp Ser Glu Ser
1               5                   10                  15

Lys Glu Asp Glu Pro Cys Ser Glu Gly Thr Asp Pro Val His Asp Leu
                20                  25                  30

Met Ala Glu Ile Leu Pro Glu Phe Pro Asp Ile Ile Glu Ile Asp Leu
            35                  40                  45

Tyr His Ser Glu Glu Asn Glu Glu Glu Glu Glu Cys Ala Asn Ala
    50                  55                  60

Thr Asp Val Thr Thr Thr Pro Ser Val Gln Tyr Ile Asn Gly Lys His
65                  70                  75                  80

Leu Val Thr Thr Val Pro Lys Asp Pro Glu Ala Ala Glu
                85                  90

<210> SEQ ID NO 16
<211> LENGTH: 245
<212> TYPE: PRT
<213> ORGANISM: Homo sapiens

<400> SEQUENCE: 16

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
                20                  25                  30

Arg Gly Ser Leu Ser Gly Lys Val Ser Leu Pro Cys His Phe Ser Thr
            35                  40                  45
```

```
Met Pro Thr Leu Pro Pro Ser Tyr Asn Thr Ser Glu Phe Leu Arg Ile
    50                  55                  60
Lys Trp Ser Lys Ile Glu Val Asp Lys Asn Gly Lys Asp Leu Lys Glu
 65                  70                  75                  80
Thr Thr Val Leu Val Ala Gln Asn Gly Asn Ile Lys Ile Gly Gln Asp
                 85                  90                  95
Tyr Lys Gly Arg Val Ser Val Pro Thr His Pro Glu Ala Val Gly Asp
                100                 105                 110
Ala Ser Leu Thr Val Val Lys Leu Leu Ala Ser Asp Ala Gly Leu Tyr
            115                 120                 125
Arg Cys Asp Val Met Tyr Gly Ile Glu Asp Thr Gln Asp Thr Val Ser
130                 135                 140
Leu Thr Val Asp Gly Val Val Phe His Tyr Arg Ala Ala Thr Ser Arg
145                 150                 155                 160
Tyr Thr Leu Asn Phe Glu Ala Ala Gln Lys Ala Cys Leu Asp Val Gly
                165                 170                 175
Ala Val Ile Ala Thr Pro Glu Gln Leu Phe Ala Ala Tyr Glu Asp Gly
            180                 185                 190
Phe Glu Gln Cys Asp Ala Gly Trp Leu Ala Asp Gln Thr Val Arg Tyr
            195                 200                 205
Pro Ile Arg Ala Pro Arg Val Gly Cys Tyr Gly Asp Lys Met Gly Lys
        210                 215                 220
Ala Gly Val Arg Thr Tyr Gly Phe Arg Ser Pro Gln Glu Thr Tyr Asp
225                 230                 235                 240
Val Tyr Cys Tyr Val
                245

<210> SEQ ID NO 17
<211> LENGTH: 225
<212> TYPE: PRT
<213> ORGANISM: Homo sapiens

<400> SEQUENCE: 17

Leu His Lys Val Lys Val Gly Lys Ser Pro Pro Val Arg Gly Ser Leu
 1               5                  10                  15
Ser Gly Lys Val Ser Leu Pro Cys His Phe Ser Thr Met Pro Thr Leu
            20                  25                  30
Pro Pro Ser Tyr Asn Thr Ser Glu Phe Leu Arg Ile Lys Trp Ser Lys
        35                  40                  45
Ile Glu Val Asp Lys Asn Gly Lys Asp Leu Lys Glu Thr Thr Val Leu
 50                  55                  60
Val Ala Gln Asn Gly Asn Ile Lys Ile Gly Gln Asp Tyr Lys Gly Arg
 65                  70                  75                  80
Val Ser Val Pro Thr His Pro Glu Ala Val Gly Asp Ala Ser Leu Thr
                 85                  90                  95
Val Val Lys Leu Leu Ala Ser Asp Ala Gly Leu Tyr Arg Cys Asp Val
            100                 105                 110
Met Tyr Gly Ile Glu Asp Thr Gln Asp Thr Val Ser Leu Thr Val Asp
            115                 120                 125
Gly Val Val Phe His Tyr Arg Ala Ala Thr Ser Arg Tyr Thr Leu Asn
130                 135                 140
Phe Glu Ala Ala Gln Lys Ala Cys Leu Asp Val Gly Ala Val Ile Ala
145                 150                 155                 160
Thr Pro Glu Gln Leu Phe Ala Ala Tyr Glu Asp Gly Phe Glu Gln Cys
                165                 170                 175
```

```
Asp Ala Gly Trp Leu Ala Asp Gln Thr Val Arg Tyr Pro Ile Arg Ala
            180                 185                 190

Pro Arg Val Gly Cys Tyr Gly Asp Lys Met Gly Lys Ala Gly Val Arg
        195                 200                 205

Thr Tyr Gly Phe Arg Ser Pro Gln Glu Thr Tyr Asp Val Tyr Cys Tyr
        210                 215                 220

Val
225

<210> SEQ ID NO 18
<211> LENGTH: 226
<212> TYPE: PRT
<213> ORGANISM: Artificial
<220> FEATURE:
<223> OTHER INFORMATION: N-terminal portion of human versikine including
      Ig-like domain and Linker domain 1 (minus signal peptide, plus N-
      terminal methionine)

<400> SEQUENCE: 18

Met Leu His Lys Val Lys Val Gly Lys Ser Pro Pro Val Arg Gly Ser
1               5                   10                  15

Leu Ser Gly Lys Val Ser Leu Pro Cys His Phe Ser Thr Met Pro Thr
            20                  25                  30

Leu Pro Pro Ser Tyr Asn Thr Ser Glu Phe Leu Arg Ile Lys Trp Ser
        35                  40                  45

Lys Ile Glu Val Asp Lys Asn Gly Lys Asp Leu Lys Glu Thr Thr Val
    50                  55                  60

Leu Val Ala Gln Asn Gly Asn Ile Lys Ile Gly Gln Asp Tyr Lys Gly
65                  70                  75                  80

Arg Val Ser Val Pro Thr His Pro Glu Ala Val Gly Asp Ala Ser Leu
                85                  90                  95

Thr Val Val Lys Leu Leu Ala Ser Asp Ala Gly Leu Tyr Arg Cys Asp
            100                 105                 110

Val Met Tyr Gly Ile Glu Asp Thr Gln Asp Thr Val Ser Leu Thr Val
        115                 120                 125

Asp Gly Val Val Phe His Tyr Arg Ala Ala Thr Ser Arg Tyr Thr Leu
    130                 135                 140

Asn Phe Glu Ala Ala Gln Lys Ala Cys Leu Asp Val Gly Ala Val Ile
145                 150                 155                 160

Ala Thr Pro Glu Gln Leu Phe Ala Ala Tyr Glu Asp Gly Phe Glu Gln
                165                 170                 175

Cys Asp Ala Gly Trp Leu Ala Asp Gln Thr Val Arg Tyr Pro Ile Arg
            180                 185                 190

Ala Pro Arg Val Gly Cys Tyr Gly Asp Lys Met Gly Lys Ala Gly Val
        195                 200                 205

Arg Thr Tyr Gly Phe Arg Ser Pro Gln Glu Thr Tyr Asp Val Tyr Cys
    210                 215                 220

Tyr Val
225

<210> SEQ ID NO 19
<211> LENGTH: 348
<212> TYPE: PRT
<213> ORGANISM: Homo sapiens
```

<400> SEQUENCE: 19

```
Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg
            340                 345
```

<210> SEQ ID NO 20
<211> LENGTH: 328
<212> TYPE: PRT
<213> ORGANISM: Homo sapiens

```
<400> SEQUENCE: 20

Leu His Lys Val Lys Val Gly Lys Ser Pro Val Arg Gly Ser Leu
1               5                   10                  15

Ser Gly Lys Val Ser Leu Pro Cys His Phe Ser Thr Met Pro Thr Leu
            20                  25                  30

Pro Pro Ser Tyr Asn Thr Ser Glu Phe Leu Arg Ile Lys Trp Ser Lys
        35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
                100                 105                 110

Met Tyr Gly Ile Glu Asp Thr Gln Asp Thr Val Ser Leu Thr Val Asp
            115                 120                 125

Gly Val Val Phe His Tyr Arg Ala Ala Thr Ser Arg Tyr Thr Leu Asn
130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
            180                 185                 190

Pro Arg Val Gly Cys Tyr Gly Asp Lys Met Gly Lys Ala Gly Val Arg
            195                 200                 205

Thr Tyr Gly Phe Arg Ser Pro Gln Glu Thr Tyr Asp Val Tyr Cys Tyr
210                 215                 220

Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
                245                 250                 255

Leu Ala Thr Val Gly Glu Leu Gln Ala Ala Trp Arg Asn Gly Phe Asp
            260                 265                 270

Gln Cys Asp Tyr Gly Trp Leu Ser Asp Ala Ser Val Arg His Pro Val
            275                 280                 285

Thr Val Ala Arg Ala Gln Cys Gly Gly Gly Leu Leu Gly Val Arg Thr
            290                 295                 300

Leu Tyr Arg Phe Glu Asn Gln Thr Gly Phe Pro Pro Pro Asp Ser Arg
305                 310                 315                 320

Phe Asp Ala Tyr Cys Phe Lys Arg
                325

<210> SEQ ID NO 21
<211> LENGTH: 329
<212> TYPE: PRT
<213> ORGANISM: Artificial
<220> FEATURE:
<223> OTHER INFORMATION: N-terminal portion of human versikine including
      Ig-like domain, Linker domain 1, and Linker domain 2 (minus signal
      peptide, plus N-terminal methionine)
```

```
<400> SEQUENCE: 21

Met Leu His Lys Val Lys Val Gly Lys Ser Pro Pro Val Arg Gly Ser
1               5                   10                  15

Leu Ser Gly Lys Val Ser Leu Pro Cys His Phe Ser Thr Met Pro Thr
                20                  25                  30

Leu Pro Pro Ser Tyr Asn Thr Ser Glu Phe Leu Arg Ile Lys Trp Ser
            35                  40                  45

Lys Ile Glu Val Asp Lys Asn Gly Lys Asp Leu Lys Glu Thr Thr Val
        50                  55                  60

Leu Val Ala Gln Asn Gly Asn Ile Lys Ile Gly Gln Asp Tyr Lys Gly
65                  70                  75                  80

Arg Val Ser Val Pro Thr His Pro Glu Ala Val Gly Asp Ala Ser Leu
                85                  90                  95

Thr Val Val Lys Leu Leu Ala Ser Asp Ala Gly Leu Tyr Arg Cys Asp
            100                 105                 110

Val Met Tyr Gly Ile Glu Asp Thr Gln Asp Thr Val Ser Leu Thr Val
        115                 120                 125

Asp Gly Val Val Phe His Tyr Arg Ala Ala Thr Ser Arg Tyr Thr Leu
    130                 135                 140

Asn Phe Glu Ala Ala Gln Lys Ala Cys Leu Asp Val Gly Ala Val Ile
145                 150                 155                 160

Ala Thr Pro Glu Gln Leu Phe Ala Ala Tyr Glu Asp Gly Phe Glu Gln
                165                 170                 175

Cys Asp Ala Gly Trp Leu Ala Asp Gln Thr Val Arg Tyr Pro Ile Arg
            180                 185                 190

Ala Pro Arg Val Gly Cys Tyr Gly Asp Lys Met Gly Lys Ala Gly Val
        195                 200                 205

Arg Thr Tyr Gly Phe Arg Ser Pro Gln Glu Thr Tyr Asp Val Tyr Cys
    210                 215                 220

Tyr Val Asp His Leu Asp Gly Asp Val Phe His Leu Thr Val Pro Ser
225                 230                 235                 240

Lys Phe Thr Phe Glu Glu Ala Ala Lys Glu Cys Glu Asn Gln Asp Ala
                245                 250                 255

Arg Leu Ala Thr Val Gly Glu Leu Gln Ala Ala Trp Arg Asn Gly Phe
            260                 265                 270

Asp Gln Cys Asp Tyr Gly Trp Leu Ser Asp Ala Ser Val Arg His Pro
        275                 280                 285

Val Thr Val Ala Arg Ala Gln Cys Gly Gly Gly Leu Leu Gly Val Arg
    290                 295                 300

Thr Leu Tyr Arg Phe Glu Asn Gln Thr Gly Phe Pro Pro Pro Asp Ser
305                 310                 315                 320

Arg Phe Asp Ala Tyr Cys Phe Lys Arg
                325

<210> SEQ ID NO 22
<211> LENGTH: 198
<212> TYPE: PRT
<213> ORGANISM: Homo sapiens

<400> SEQUENCE: 22

Val Val Phe His Tyr Arg Ala Ala Thr Ser Arg Tyr Thr Leu Asn Phe
1               5                   10                  15

Glu Ala Ala Gln Lys Ala Cys Leu Asp Val Gly Ala Val Ile Ala Thr
                20                  25                  30
```

```
Pro Glu Gln Leu Phe Ala Ala Tyr Glu Asp Gly Phe Glu Gln Cys Asp
            35                  40                  45

Ala Gly Trp Leu Ala Asp Gln Thr Val Arg Tyr Pro Ile Arg Ala Pro
 50                  55                  60

Arg Val Gly Cys Tyr Gly Asp Lys Met Gly Lys Ala Gly Val Arg Thr
 65                  70                  75                  80

Tyr Gly Phe Arg Ser Pro Gln Glu Thr Tyr Asp Val Tyr Cys Tyr Val
                 85                  90                  95

Asp His Leu Asp Gly Asp Val Phe His Leu Thr Val Pro Ser Lys Phe
            100                 105                 110

Thr Phe Glu Glu Ala Ala Lys Glu Cys Glu Asn Gln Asp Ala Arg Leu
        115                 120                 125

Ala Thr Val Gly Glu Leu Gln Ala Ala Trp Arg Asn Gly Phe Asp Gln
        130                 135                 140

Cys Asp Tyr Gly Trp Leu Ser Asp Ala Ser Val Arg His Pro Val Thr
145                 150                 155                 160

Val Ala Arg Ala Gln Cys Gly Gly Gly Leu Leu Gly Val Arg Thr Leu
                165                 170                 175

Tyr Arg Phe Glu Asn Gln Thr Gly Phe Pro Pro Pro Asp Ser Arg Phe
            180                 185                 190

Asp Ala Tyr Cys Phe Lys
            195

<210> SEQ ID NO 23
<211> LENGTH: 199
<212> TYPE: PRT
<213> ORGANISM: Artificial
<220> FEATURE:
<223> OTHER INFORMATION: Internal portion of human versikine including
      Linker domain 1 and Linker domain 2 (plus N-terminal methionine)

<400> SEQUENCE: 23

Met Val Val Phe His Tyr Arg Ala Ala Thr Ser Arg Tyr Thr Leu Asn
 1               5                  10                  15

Phe Glu Ala Ala Gln Lys Ala Cys Leu Asp Val Gly Ala Val Ile Ala
            20                  25                  30

Thr Pro Glu Gln Leu Phe Ala Ala Tyr Glu Asp Gly Phe Glu Gln Cys
        35                  40                  45

Asp Ala Gly Trp Leu Ala Asp Gln Thr Val Arg Tyr Pro Ile Arg Ala
 50                  55                  60

Pro Arg Val Gly Cys Tyr Gly Asp Lys Met Gly Lys Ala Gly Val Arg
 65                  70                  75                  80

Thr Tyr Gly Phe Arg Ser Pro Gln Glu Thr Tyr Asp Val Tyr Cys Tyr
                 85                  90                  95

Val Asp His Leu Asp Gly Asp Val Phe His Leu Thr Val Pro Ser Lys
            100                 105                 110

Phe Thr Phe Glu Glu Ala Ala Lys Glu Cys Glu Asn Gln Asp Ala Arg
        115                 120                 125

Leu Ala Thr Val Gly Glu Leu Gln Ala Ala Trp Arg Asn Gly Phe Asp
        130                 135                 140

Gln Cys Asp Tyr Gly Trp Leu Ser Asp Ala Ser Val Arg His Pro Val
145                 150                 155                 160

Thr Val Ala Arg Ala Gln Cys Gly Gly Gly Leu Leu Gly Val Arg Thr
                165                 170                 175
```

Leu Tyr Arg Phe Glu Asn Gln Thr Gly Phe Pro Pro Asp Ser Arg
                180                 185                 190

Phe Asp Ala Tyr Cys Phe Lys
            195

<210> SEQ ID NO 24
<211> LENGTH: 292
<212> TYPE: PRT
<213> ORGANISM: Homo sapiens

<400> SEQUENCE: 24

Val Val Phe His Tyr Arg Ala Ala Thr Ser Arg Tyr Thr Leu Asn Phe
1               5                   10                  15

Glu Ala Ala Gln Lys Ala Cys Leu Asp Val Gly Ala Val Ile Ala Thr
            20                  25                  30

Pro Glu Gln Leu Phe Ala Ala Tyr Glu Asp Gly Phe Glu Gln Cys Asp
        35                  40                  45

Ala Gly Trp Leu Ala Asp Gln Thr Val Arg Tyr Pro Ile Arg Ala Pro
    50                  55                  60

Arg Val Gly Cys Tyr Gly Asp Lys Met Gly Lys Ala Gly Val Arg Thr
65                  70                  75                  80

Tyr Gly Phe Arg Ser Pro Gln Glu Thr Tyr Asp Val Tyr Cys Tyr Val
                85                  90                  95

Asp His Leu Asp Gly Asp Val Phe His Leu Thr Val Pro Ser Lys Phe
            100                 105                 110

Thr Phe Glu Glu Ala Ala Lys Glu Cys Glu Asn Gln Asp Ala Arg Leu
        115                 120                 125

Ala Thr Val Gly Glu Leu Gln Ala Ala Trp Arg Asn Gly Phe Asp Gln
    130                 135                 140

Cys Asp Tyr Gly Trp Leu Ser Asp Ala Ser Val Arg His Pro Val Thr
145                 150                 155                 160

Val Ala Arg Ala Gln Cys Gly Gly Gly Leu Leu Gly Val Arg Thr Leu
                165                 170                 175

Tyr Arg Phe Glu Asn Gln Thr Gly Phe Pro Pro Pro Asp Ser Arg Phe
            180                 185                 190

Asp Ala Tyr Cys Phe Lys Arg Arg Met Ser Asp Leu Ser Val Ile Gly
        195                 200                 205

His Pro Ile Asp Ser Glu Ser Lys Glu Asp Glu Pro Cys Ser Glu Glu
    210                 215                 220

Thr Asp Pro Val His Asp Leu Met Ala Glu Ile Leu Pro Glu Phe Pro
225                 230                 235                 240

Asp Ile Ile Glu Ile Asp Leu Tyr His Ser Glu Glu Asn Glu Glu Glu
                245                 250                 255

Glu Glu Glu Cys Ala Asn Ala Thr Asp Val Thr Thr Thr Pro Ser Val
            260                 265                 270

Gln Tyr Ile Asn Gly Lys His Leu Val Thr Thr Val Pro Lys Asp Pro
        275                 280                 285

Glu Ala Ala Glu
    290

<210> SEQ ID NO 25
<211> LENGTH: 293
<212> TYPE: PRT
<213> ORGANISM: Artificial

<220> FEATURE:
<223> OTHER INFORMATION: C-terminal portion of human versikine including
      Linker domain 1, Linker domain 2, and portion of Gag-beta domain
      (plus N-terminal methionine)

<400> SEQUENCE: 25

Met Val Val Phe His Tyr Arg Ala Ala Thr Ser Arg Tyr Thr Leu Asn
1               5                   10                  15

Phe Glu Ala Ala Gln Lys Ala Cys Leu Asp Val Gly Ala Val Ile Ala
            20                  25                  30

Thr Pro Glu Gln Leu Phe Ala Ala Tyr Glu Asp Gly Phe Glu Gln Cys
        35                  40                  45

Asp Ala Gly Trp Leu Ala Asp Gln Thr Val Arg Tyr Pro Ile Arg Ala
    50                  55                  60

Pro Arg Val Gly Cys Tyr Gly Asp Lys Met Gly Lys Ala Gly Val Arg
65                  70                  75                  80

Thr Tyr Gly Phe Arg Ser Pro Gln Glu Thr Tyr Asp Val Tyr Cys Tyr
                85                  90                  95

Val Asp His Leu Asp Gly Asp Val Phe His Leu Thr Val Pro Ser Lys
            100                 105                 110

Phe Thr Phe Glu Glu Ala Ala Lys Glu Cys Glu Asn Gln Asp Ala Arg
        115                 120                 125

Leu Ala Thr Val Gly Glu Leu Gln Ala Ala Trp Arg Asn Gly Phe Asp
    130                 135                 140

Gln Cys Asp Tyr Gly Trp Leu Ser Asp Ala Ser Val Arg His Pro Val
145                 150                 155                 160

Thr Val Ala Arg Ala Gln Cys Gly Gly Gly Leu Leu Gly Val Arg Thr
                165                 170                 175

Leu Tyr Arg Phe Glu Asn Gln Thr Gly Phe Pro Pro Pro Asp Ser Arg
            180                 185                 190

Phe Asp Ala Tyr Cys Phe Lys Arg Arg Met Ser Asp Leu Ser Val Ile
        195                 200                 205

Gly His Pro Ile Asp Ser Glu Ser Lys Glu Asp Glu Pro Cys Ser Glu
    210                 215                 220

Glu Thr Asp Pro Val His Asp Leu Met Ala Glu Ile Leu Pro Glu Phe
225                 230                 235                 240

Pro Asp Ile Ile Glu Ile Asp Leu Tyr His Ser Glu Glu Asn Glu Glu
                245                 250                 255

Glu Glu Glu Glu Cys Ala Asn Ala Thr Asp Val Thr Thr Thr Pro Ser
            260                 265                 270

Val Gln Tyr Ile Asn Gly Lys His Leu Val Thr Thr Val Pro Lys Asp
        275                 280                 285

Pro Glu Ala Ala Glu
    290

<210> SEQ ID NO 26
<211> LENGTH: 191
<212> TYPE: PRT
<213> ORGANISM: Homo sapiens

<400> SEQUENCE: 26

Asp Val Phe His Leu Thr Val Pro Ser Lys Phe Thr Phe Glu Glu Ala
1               5                   10                  15

Ala Lys Glu Cys Glu Asn Gln Asp Ala Arg Leu Ala Thr Val Gly Glu
            20                  25                  30

-continued

```
Leu Gln Ala Ala Trp Arg Asn Gly Phe Asp Gln Cys Asp Tyr Gly Trp
         35                  40                  45
Leu Ser Asp Ala Ser Val Arg His Pro Val Thr Val Ala Arg Ala Gln
 50                  55                  60
Cys Gly Gly Gly Leu Leu Gly Val Arg Thr Leu Tyr Arg Phe Glu Asn
 65                  70                  75                  80
Gln Thr Gly Phe Pro Pro Pro Asp Ser Arg Phe Asp Ala Tyr Cys Phe
                 85                  90                  95
Lys Arg Arg Met Ser Asp Leu Ser Val Ile Gly His Pro Ile Asp Ser
                100                 105                 110
Glu Ser Lys Glu Asp Glu Pro Cys Ser Glu Glu Thr Asp Pro Val His
            115                 120                 125
Asp Leu Met Ala Glu Ile Leu Pro Glu Phe Pro Asp Ile Ile Glu Ile
130                 135                 140
Asp Leu Tyr His Ser Glu Glu Asn Glu Glu Glu Glu Glu Glu Cys Ala
145                 150                 155                 160
Asn Ala Thr Asp Val Thr Thr Thr Pro Ser Val Gln Tyr Ile Asn Gly
                165                 170                 175
Lys His Leu Val Thr Thr Val Pro Lys Asp Pro Glu Ala Ala Glu
                180                 185                 190

<210> SEQ ID NO 27
<211> LENGTH: 192
<212> TYPE: PRT
<213> ORGANISM: Artificial
<220> FEATURE:
<223> OTHER INFORMATION: C-terminal portion of human versikine including
      Linker domain 2 and portion of Gag-beta domain (plus N-terminal
      methionine)

<400> SEQUENCE: 27

Met Asp Val Phe His Leu Thr Val Pro Ser Lys Phe Thr Phe Glu Glu
  1               5                  10                  15
Ala Ala Lys Glu Cys Glu Asn Gln Asp Ala Arg Leu Ala Thr Val Gly
             20                  25                  30
Glu Leu Gln Ala Ala Trp Arg Asn Gly Phe Asp Gln Cys Asp Tyr Gly
         35                  40                  45
Trp Leu Ser Asp Ala Ser Val Arg His Pro Val Thr Val Ala Arg Ala
 50                  55                  60
Gln Cys Gly Gly Gly Leu Leu Gly Val Arg Thr Leu Tyr Arg Phe Glu
 65                  70                  75                  80
Asn Gln Thr Gly Phe Pro Pro Pro Asp Ser Arg Phe Asp Ala Tyr Cys
                 85                  90                  95
Phe Lys Arg Arg Met Ser Asp Leu Ser Val Ile Gly His Pro Ile Asp
                100                 105                 110
Ser Glu Ser Lys Glu Asp Glu Pro Cys Ser Glu Glu Thr Asp Pro Val
            115                 120                 125
His Asp Leu Met Ala Glu Ile Leu Pro Glu Phe Pro Asp Ile Ile Glu
130                 135                 140
Ile Asp Leu Tyr His Ser Glu Glu Asn Glu Glu Glu Glu Glu Glu Cys
145                 150                 155                 160
Ala Asn Ala Thr Asp Val Thr Thr Thr Pro Ser Val Gln Tyr Ile Asn
                165                 170                 175
Gly Lys His Leu Val Thr Thr Val Pro Lys Asp Pro Glu Ala Ala Glu
                180                 185                 190
```

VERSIKINE FOR INDUCING AND POTENTIATING AN IMMUNE RESPONSE

CROSS-REFERENCE TO RELATED PATENT APPLICATIONS

The present application claims the benefit of priority under 35 U.S.C. § 119(e) to U.S. Provisional Application No. 62/437,418, filed on Dec. 21, 2016, and to U.S. Provisional Application No. 62/343,414, filed on May 31, 2016, and to U.S. Provisional Application No. 62/305,761, filed on Mar. 9, 2016, the contents of which are incorporated herein by reference in their entireties.

BACKGROUND

The field of the invention relates to methods and compositions for inducing and/or potentiating an immune response. In particular, the field of the invention relates to methods and compositions that utilize and/or include versikine for inducing and/or potentiating a T-cell mediated immune response.

Versican, also known by the synonyms PG-M and CSPG2, was identified first in the culture of labeled fibroblasts. (See Coster et al., (1979)). Versican is a chondroitin sulfate (CS) proteoglycan that belongs to a family of hyaluronan (HA) binding proteins. The human versican gene is located on chromosome 5q and contains 15 exons. The versican glycoprotein comprises three major functional domains including: an N-terminal globular domain that mediates HA binding via two linking sub-domains, one or two alternatively spliced glycosaminoglycan (GAG) attachment domains referred to as GAGα and GAGβ, and a C-terminal G3 domain. (See Zimmermann et al., (1989)). Five different splice variants result in five different versican isoforms referred to as V0, V1, V2, V3, and V4. (See Dours-Zimmermann, et al., (1994)). Versican V0 contains both GAGα and GAGβ attachment exons and is the largest isoform, containing up to 23 CS chains; versican V1 contains only exon 8 and has up to 15 CS chains; versican V2 contains only exon 7 and has up to 8 GAG attachment sites; versican V3 does not contain either large exon and thus lacks CS chains; versican V4 has a truncated GAGβ domain from utilization of a cryptic splice site in exon 8 and 5 predicted CS attachment sites. (See id.; see also, Kischel et al., 2010).

Versican has been shown to bind to Toll-like receptor-2 (TLR2) receptor complexes on tumor-infiltrating myeloid cells and regulate inflammatory cytokine production (Kim et al., 2009), promote tolerogenic polarization of antigen-presenting cells (Tang et al., 2015), and promote the mesenchymal-epithelial transition in the carcinoma metastatic niche (Gao et al., 2012). Versican is proteolytically cleaved by ADAMTS-type proteases in a highly-regulated manner that involves CS chains. A cleavage product generated by disruption of a Glu-Ala bond at position 441 of versican's V1 isoform, has been previously termed versikine (Nandadasa et al., 2014). Versikine has been shown to be bioactive in development (McCulloch et al., 2009). However, the roles of versican proteolysis and/or versikine in immunomodulation remain unknown.

SUMMARY

Disclosed are methods and compositions for inducing and/or potentiating an immune response. The present inventors have determined that versikine can be administered in order to induce and/or potentiate, in particular, a T-cell mediated immune response, which may be characterized by a T-cell inflamed phenotype. As such, the inventors have determined that versikine can be administered to potentiate T-cell activating immunotherapies, including chimeric antigen receptor (CAR) T-cell therapies, tumor infiltrating lymphocyte (TIL) therapies, and other cellular therapies utilized for treating cell proliferative diseases or disorders. The inventors also have determined that versikine can be administered to potentiate other therapies utilized for treating cell proliferative diseases or disorders whose efficacy is linked to a T-cell inflamed phenotype, including, but not limited to, conventional chemotherapies, targeted therapies, oncolytic viral therapies, and radiotherapy.

The disclosed methods include methods for inducing an immune response in a subject in need thereof. The immune response induced and/or potentiated by the disclosed methods may include a T-cell mediated immune response, optionally characterized by a type 1 interferon signature (i.e., a type 1 interferon expression profile), expression of chemokines that attract T-cells (e.g., CCL2), expression of T-cell specific transcripts, and expression of macrophage-activation markers. The disclosed methods may include administering to the subject in need thereof a pharmaceutical composition comprising an effective amount of versikine or a variant thereof that induces the T-cell mediated immune response. The pharmaceutical composition may be administered by any suitable route including, for example, systemically or by injecting the pharmaceutical composition directly into tissue (e.g., tumor tissue).

The disclosed methods also may include administering the pharmaceutical composition comprising an effective amount of versikine or a variant thereof that induces and/or potentiates a T-cell mediated immune response to explanted cells from a subject, for example, in a method in which the explanted cells are treated with the pharmaceutical composition ex vivo. The explanted cells thus treated may then be administered back to the subject, for example, by re-infusion. The explanted cells may include immune cells (e.g., T-cells or dendritic cells), which optionally are treated, contacted, or primed with an antigen (e.g., a tumor antigen), either before, concurrently with, or after treatment with the pharmaceutical composition comprising an effective amount of versikine or a variant thereof. The explanted cells may include tumor cells.

The disclosed methods include methods for treating cell proliferative diseases and disorders such as cancers in a subject by administering to the subject a pharmaceutical composition comprising an effective amount of versikine or a variant thereof that induces and/or potentiates a T-cell mediated immune response. As such, cancers treated by the disclosed methods may include cancers that are characterized by an impaired T-cell mediated immune response, and in particular, an impaired T-cell inflamed phenotype. As an example, the disclosed methods may include methods of administering versikine or a variant thereof to a subject having a non-T-cell inflamed tumor. In the disclosed methods for treating cancer in a subject, the methods further may include administering to the subject cancer therapy before, concurrently with, or after administering the pharmaceutical composition comprising versikine or the variant thereof. Suitable cancer therapies may include, but are not limited to, administering chemotherapeutic agents.

Also disclosed are methods for determining whether a subject will benefit from a method that includes administering to the subject a pharmaceutical composition comprising an effective amount of versikine or a variant thereof that induces and/or potentiates a T-cell mediated immune response. The methods may include determining the concentration of versikine in a biological sample from the subject (e.g., a blood product), and if the determined level is determined to be below a selected baseline, then administering the pharmaceutical composition comprising versikine or the variant thereof that induces and/or potentiates a T-cell mediated immune response.

Also disclosed are kits comprising components that optionally may be utilized to perform the methods disclosed herein. The kits may include one or more of (a) versikine or a variant thereof, where the versikine or the variant thereof optionally is provided as a pharmaceutical composition; and (b) a reagent for detecting the concentration of versikine in a biological sample (e.g., an anti-versikine antibody which optionally is labelled with a detectable label).

Also disclosed are isolated polypeptides which may include non-naturally occurring isolated polypeptides. The isolated polypeptides typically exhibit one or more biological activities associated with versikine, which include, but are not limited to, inducing and/or potentiating a T-cell mediated immune response. The isolated polypeptides may be formulated as a pharmaceutical composition, which preferably comprises an effective amount of the polypeptides for inducing and/or potentiating a T-cell mediated immune response in a subject in need thereof. The isolated polypeptides may be fused and/or conjugated to other therapeutic polypeptides, including but not limited to, therapeutic antibodies, therapeutic bi-specific antibodies, and/or therapeutic ligands.

Also disclosed are isolated polynucleotides encoded any of the isolated polypeptides disclosed herein. The isolated polynucleotide may be present in vectors for replication of the polynucleotides or for expression of the encoded polypeptides, for example, where the polynucleotides are operably linked to a promoter. Also disclosed are isolated cells that comprise the isolated polynucleotides, particular the isolated polynucleotides as present in the disclosed vectors. Also disclosed are methods for expressing the encoded polypeptides, which methods include culturing the isolated cells as disclosed herein.

BRIEF DESCRIPTION OF THE DRAWINGS

FIG. 1. CD8+ aggregate infiltration in myeloma bone marrows with active versican proteolysis. Staining of bone marrow biopsies with antibodies against neoepitope DPEAAE generated by V1-versican cleavage at $Glu^{441}$-$Ala^{442}$, macrophage marker CD68 and T-cell marker CD8. Four patterns of staining were observed in 19 informative punches, as shown. Arrow points at a CD8+ lymphocytic aggregate (>5 CD8+ cells in cluster). CD8–"poor" pattern refers to single CD8+ cells (occasionally doublets) sparsely distributed within tumor.

FIG. 2. Cellular origin of versican and versican-degrading proteases in the myeloma microenvironment. A. Isoform-specific primers detected expression of versican isoforms by MAM (CD14+) but not myeloma tumor cells (CD138+) or myeloma BM-MSC isolated from the cases indicated. B. Relative expression of ADAMTS1, ADAMTS4, and ADAMTS5 mRNA in myeloma bone marrow stromal cells (BM-MSC) compared to normal BM-MSC. C. ADAMTS1 mRNA was robustly expressed in BM-MSC (note logarithmic scale). * $p<0.05$.

FIG. 3. Versikine stimulates inflammatory cytokine production by primary MAM. A. and B. Freshly explanted MAM were exposed to 1 μM versikine for 12 hours. Relative expression of IL6 and IL1β transcripts is shown. C. MM1.S myeloma cells were exposed to 1 μM versikine overnight and labeled with BrdU for 30 minutes prior to analysis. Anti-BrdU/PI FACS analysis was employed to determine the relative proportion of cells in each phase of the cell cycle. * $p<0.05$;  $p<0.01$; * $p<0.001$.

FIG. 4. Tpl2 and Tlr2 are implicated in versikine signaling. Tpl2–/– bone-marrow-derived macrophages (BMDM) were treated with 1 μM versikine and cytokine concentrations were measured in the culture supernatant at 12 hours post-exposure. A., IL1β; B., IL6; C., IL10; D, IL12p40. E. Signaling mediators induced by versikine stimulation of BMDM were evaluated. BMDM were collected following stimulation with versikine at designed timepoints (each number reflects minutes) and subjected to immunoblot analysis with the antibodies shown. F. Tlr2–/– BMDM were stimulated by versikine for 12 hours and IL6 protein was measured in the supernatant. G. Versikine modulates macrophage polarization. BMDM were exposed to versikine alone (A) or versikine+OVA/anti-OVA immune complexes (IC), as previously described (Edwards et al., 2006). Versikine exposure resulted in M1-like phenotype ($IL12^{hi}$, $IL10^{lo}$) in the absence of concurrent Fcγ ligation. Versikine+IC promoted macrophage polarization towards an M2b-like, immunoregulatory phenotype ($IL12^{lo}$, $IL10^{hi}$). ***$p<0.001$.

FIG. 5. Versikine induces upregulation of IRF8 and interferon-stimulated-genes (ISG). A. RNA-seq analysis of MM1.S myeloma cells exposed to versikine-producing macrophages for 48 h. Only 23 genes were differentially expressed and all were upregulated. 13 of 23 upregulated genes were interferon-stimulated-genes (ISG, highlighted yellow). VCAN gene transcription changes are highlighted in blue. B. RNA-seq analysis of THP-1 cells expressing versikine following co-culture with MM1.S cells for 48 hours. Genes shown were differentially expressed at least 2-fold ($log^2$ fold change > or equal to 1 for overexpressed, < or equal to 1 for underexpressed) with a threshold false discovery rate (FDR) of 0.05. ISGs are highlighted in yellow; VCAN gene transcription changes are highlighted in blue; EBI3 transcription changes are highlighted in grey (FDR for EBI3 was 0.053). C and D. MM1.S and THP-1-derived macrophage co-cultures were exposed to 0.5 μM of purified versikine for 4, 18 or 48 hours. RNA was collected from each cell type and analyzed by RT-PCR using an interferon signaling RT-PCR array (see Materials and Methods). Representative ISG transcription is shown for MM1.S (FIG. 5C) and THP-1 cells (FIG. 5D). E. Interferon regulatory factor (IRF) transcription in MM1.S cells following treatment with versikine (Vkn) versus vehicle (Veh). Expression is normalized to Veh-only levels at 4 h. F. IRF9 mRNA levels in MM1.S cells co-cultured with macrophages and treated with versikine and compared to vehicle-only control at each timepoint. G. EBI3 transcription in MM1.S cells co-cultured with macrophages and treated with versikine (grey bars) or vehicle (black bars) for designated time-lengths. H. RT-PCR analysis for EBI3 transcripts in patient-derived, freshly-explanted MAM treated with 0.5 μM versikine for 12 hours. Relative expression is normalized to vehicle-only control (=1). * $p<0.05$;  $p<0.01$; * $p<0.001$.

FIG. 6. VCAN accumulation and processing in colorectal cancer. A tissue microarray containing matched cores from colorectal cancers and the tumor-associated normal colon was stained for total VCAN and αDPEAAE, a neoepitope generated from VCAN cleavage at $Glu^{441}$-$Ala^{442}$ (V1-enumeration) (A). VCAN staining was observed variably within the stroma of CRCs, however overall an increase in the intensity of VCAN staining was observed in the tumor tissues compared to the normal colon (Chi-square test, p<0.001, A and B). VCAN proteolysis, as determined by αDPEAAE staining, was extensive in the stroma of normal tissue and markedly reduced in numerous CRCs (Chi-square test, p<0.001, A and C). Scale bar in A=100 µm.

Figure 7:
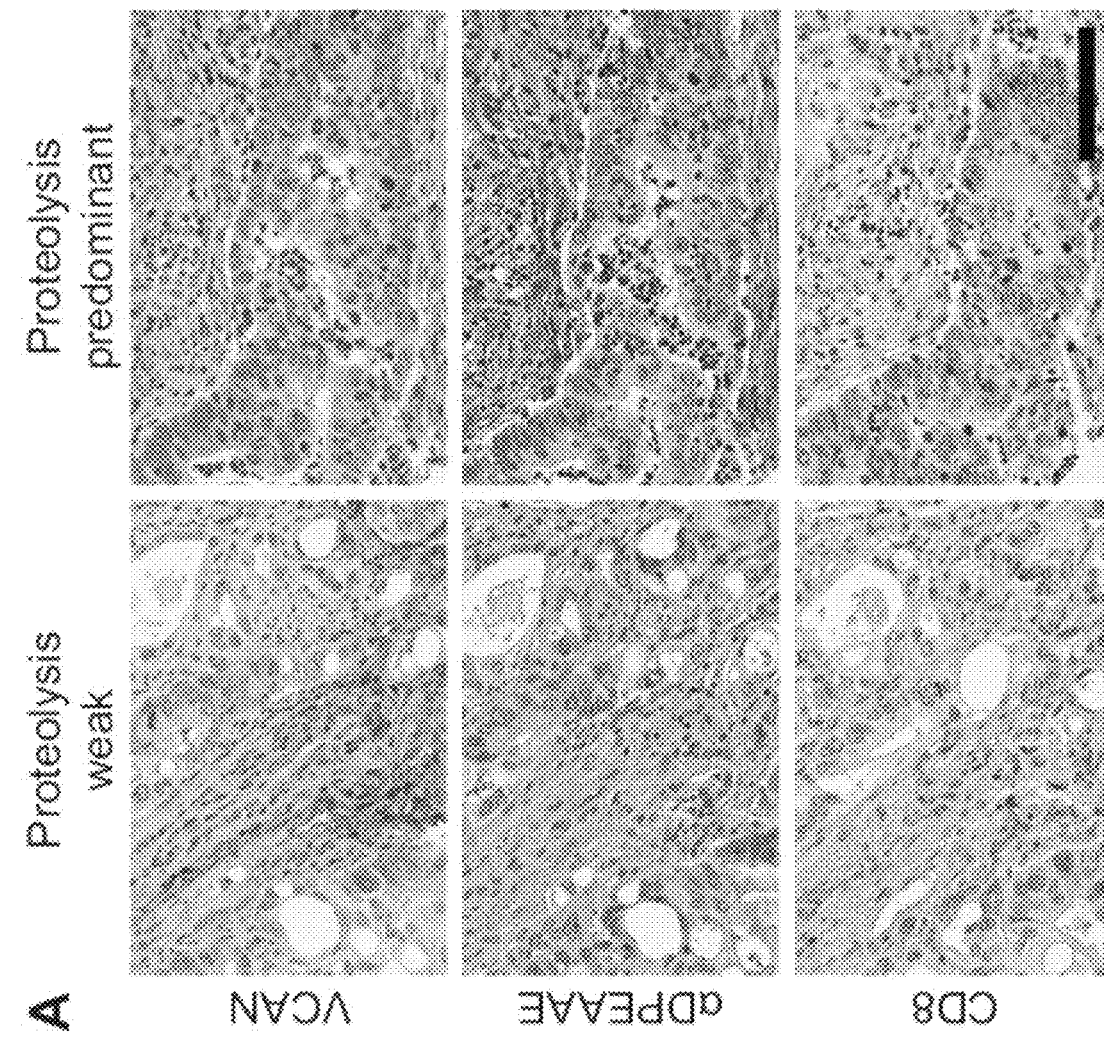
Figure 7:
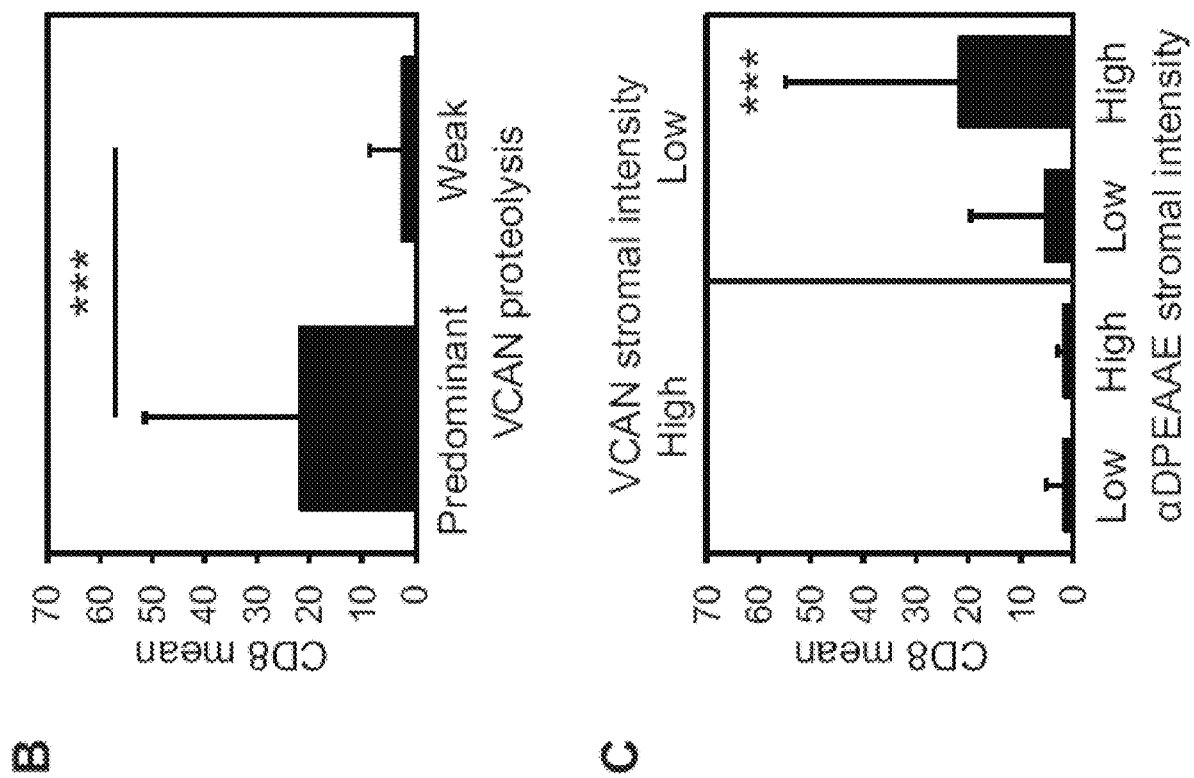

FIG. 7. Robust CD8+ T-cell infiltration in "VCAN proteolysis-predominant" tumors. Colorectal cancers were classified as "VCAN proteolysis-predominant" if their staining for total VCAN was weak (≤1+) and staining for versican proteolysis was strong (αDPEAAE intensity ≥2+). Tumors that did not meet those criteria were classified as "proteolysis-weak" (A). Given the immunoregulatory properties of VCAN and the immunostimulatory properties of its proteolytic product, versikine, CD8+ T-cell infiltration was assessed comparing VCAN proteolysis-predominant cancers versus proteolysis-weak cancers. Proteolysis-predominant tumors display 10-fold higher CD8 scores on average than proteolysis-weak tumors (Wilcoxon rank sum test, p<0.001; B). CD8+ T-cell infiltration is greatest in cancers with intensive VCAN proteolysis and low total VCAN (Wilcoxon rank sum test, p<0.001, C). Scale bar in A=100 µm.

Figure 8:
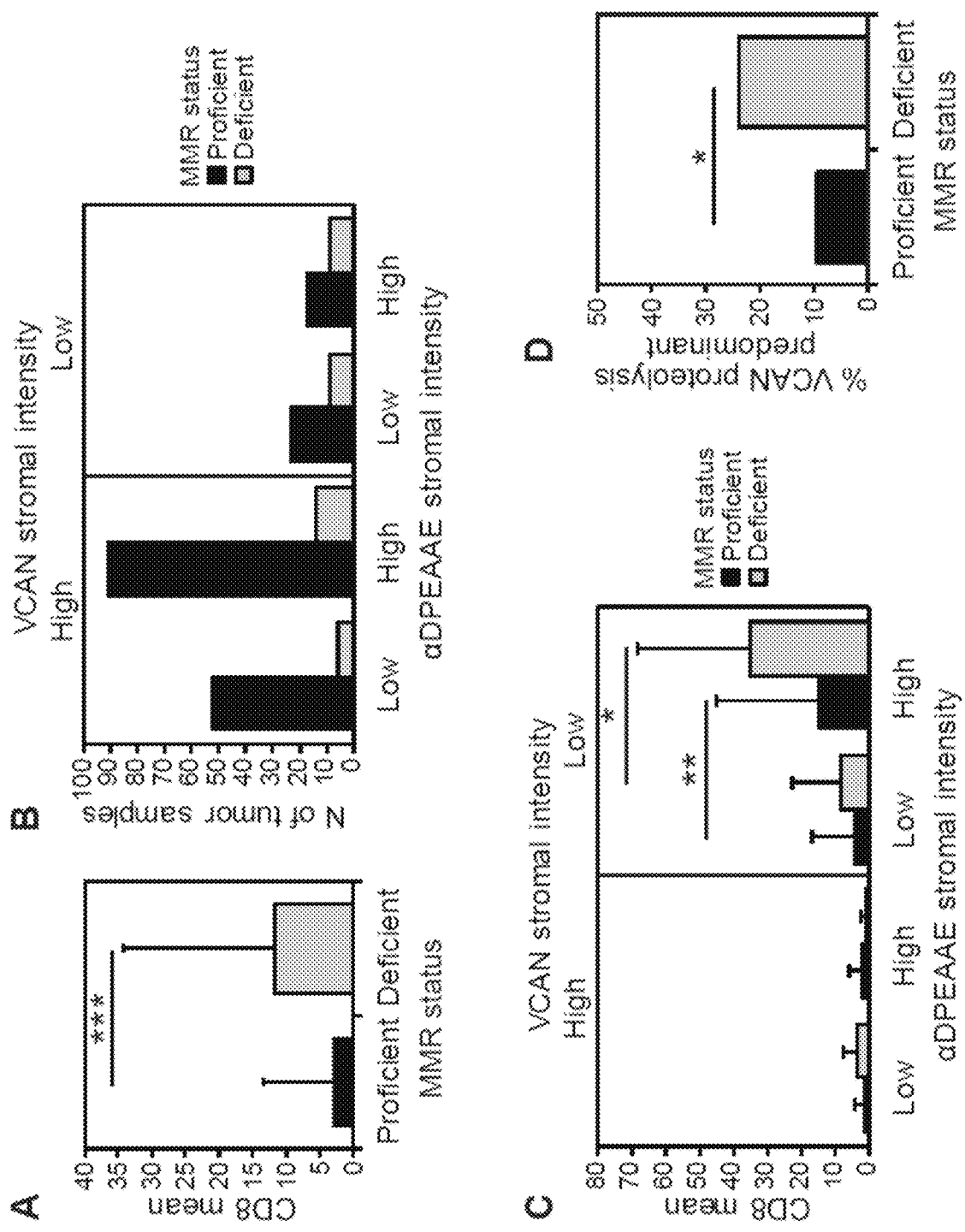
Figure 8:
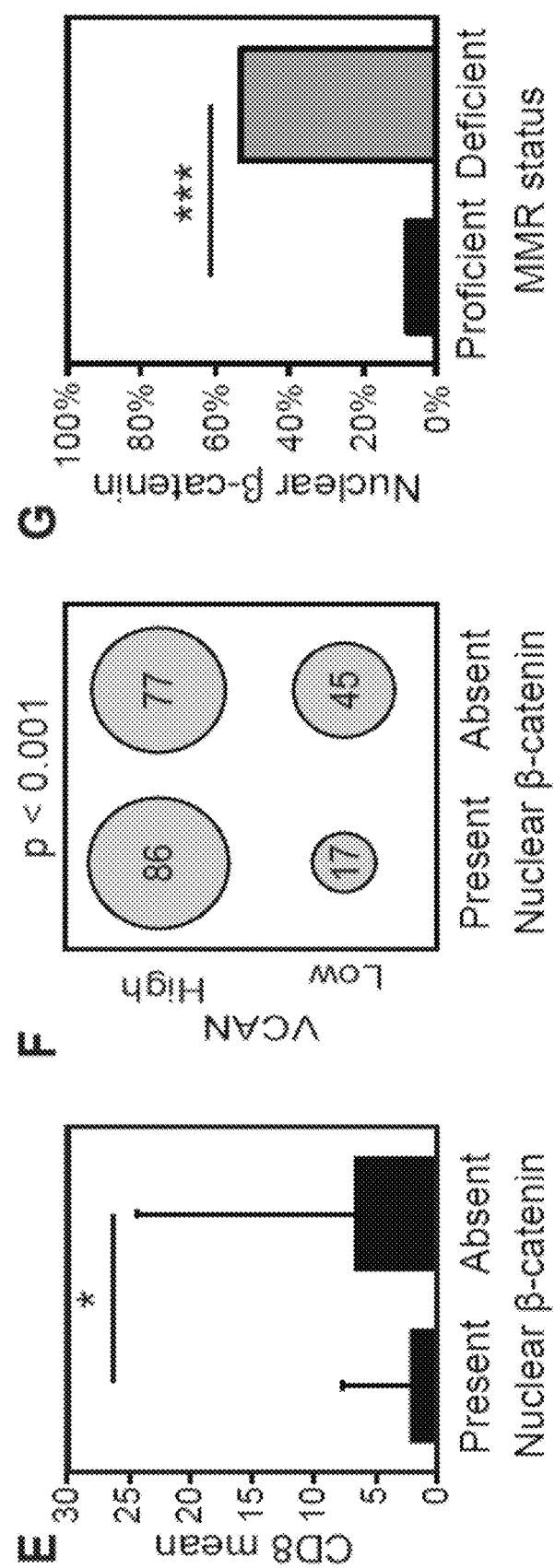

FIG. 8. Impact of VCAN proteolysis on CD8+ T-cell infiltration in MMR proficient and deficient cancers. Identification of cases within the TMA with MMR deficiency was performed by IHC analysis for MLH1, MSH2, PMS2 and MSH6. Loss of staining for any of these proteins confirmed MMR deficiency. Non-tumor cells were utilized as an internal control. Increased CD8+ T-cell infiltration in dMMR cancers was confirmed in the TMA CRC cores with a mean of 11.7 CD8+ T-cells per HPF in dMMR tumors compared to 3.1 per HPF in pMMR (Wilcoxon rank sum test, p<0.001; A). The intensity of staining for both VCAN and αDPEAAE varied across both dMMR and pMMR cancers with a trend toward more intense VCAN stromal staining in pMMR cancers (B). In both pMMR and dMMR cancers, the VCAN proteolysis predominant cancers had the greatest infiltration of CD8+ T-cells (Wilcoxon rank sum test, dMMR p=0.031, pMMR p=0.006; C). Comparing the VCAN proteolysis-predominant tumors, the dMMR cancers had increased CD8+ T-cell infiltration compared to the pMMR cancers (Wilcoxon rank sum test, p=0.04; C). The proportion of VCAN proteolysis predominant tumors varies depending on the MMR status with this being more common in dMMR tumors (Wilcoxon rank sum test, p=0.01; D). Truncating mutations in APC are commonly encountered in CRC and activation of WNT signaling has demonstrated immunoregulatory properties (20). To examine the impact of activation of WNT signaling, IHC staining for β-catenin was performed and the presence of nuclear localization of β-catenin was assessed. Those tumors with nuclear β-catenin had a significant reduction in CD8+ T-cell infiltration (Wilcoxon rank sum test, p=0.01; E). In addition, those tumors with nuclear localization of β-catenin had a higher rate of intense staining for VCAN (Chi-square test, p<0.001; F). Nuclear β-catenin was more common in the pMMR cancers (8 vs. 53%, Chi-square test, p<0.001, G).

FIG. 9. Versikine, a product of VCAN proteolysis, promotes CD103+CD11c$^{hi}$MHCII$^{hi}$ DC generation from flt3L-mobilized bone marrow progenitors. A. Bone marrow (BM) from C57BL/6J animals was isolated and cultured in the presence of 200 ng/mL flt3L for 9 days, as previously described (19). At conclusion of culture, a mixture of DC precursors and mature DC is obtained in this well-characterized system. Addition of versikine (1 mM) at D#0, alongside flt3L, resulted in reproducible expansion of CD103+CD11c$^{hi}$MHCII$^{hi}$ DC (at least 5 independent experiments). Although the total number of CD11c+ cells was similar between vehicle- and versikine-supplemented cultures, there was a consistent skewing towards CD103+ differentiation, measurable at both earlier culture timepoints (4 days, A) and later culture timepoints (9 days, B). CD103+ MHCII$^{hi}$ cells were SIRPa$^{lo}$, CD11b$^{lo-int}$ and SiglecH$^{lo}$ confirming their identity as CD103+ conventional DC (cDC) (B). Versikine-supplemented flt3L-mobilized BM cultures demonstrate increased expression of the CD103+DC terminal selector, Irf8, as well as transcription factor Batf3 (C). Intact VCAN acts through TLR2/6 heterodimers. Addition of the TLR2/6 ligand, FSL-1, to flt3L-supplemented cultures results in a disadvantage to CD103+MHCII$^{hi}$ expansion, suggesting that versikine acts through mechanisms distinct from intact VCAN (D).

Figure 10:
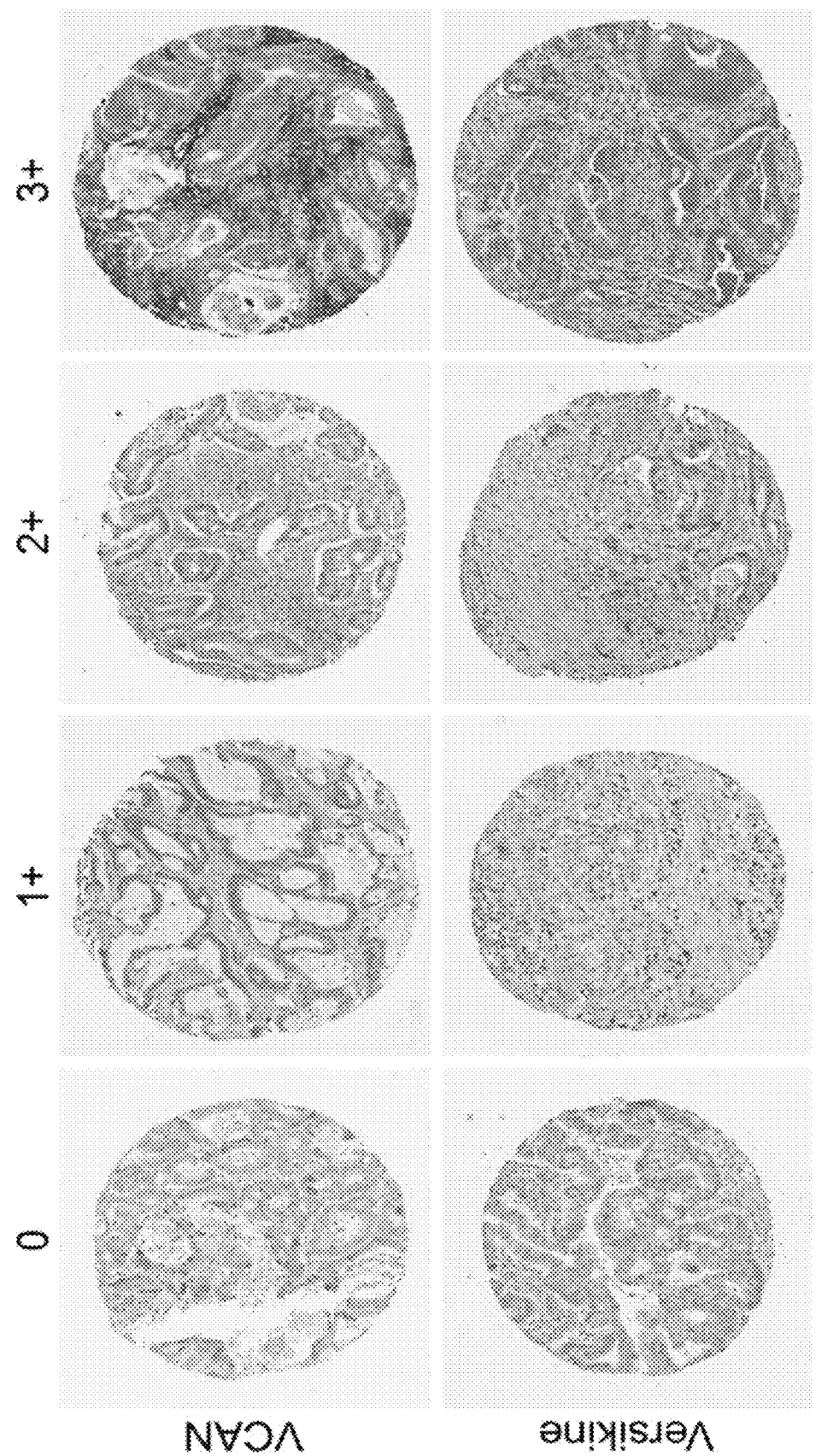

FIG. 10. VCAN and αDPEAAE staining intensity scoring. The normal colon tissue and CRCs on the TMA were stained for VCAN and αDPEAAE. The staining intensity of each core was categorized as 0 for no staining, 1 for low/weak staining, 2 for moderate staining and 3 for strong/intense staining.

Figure 11:
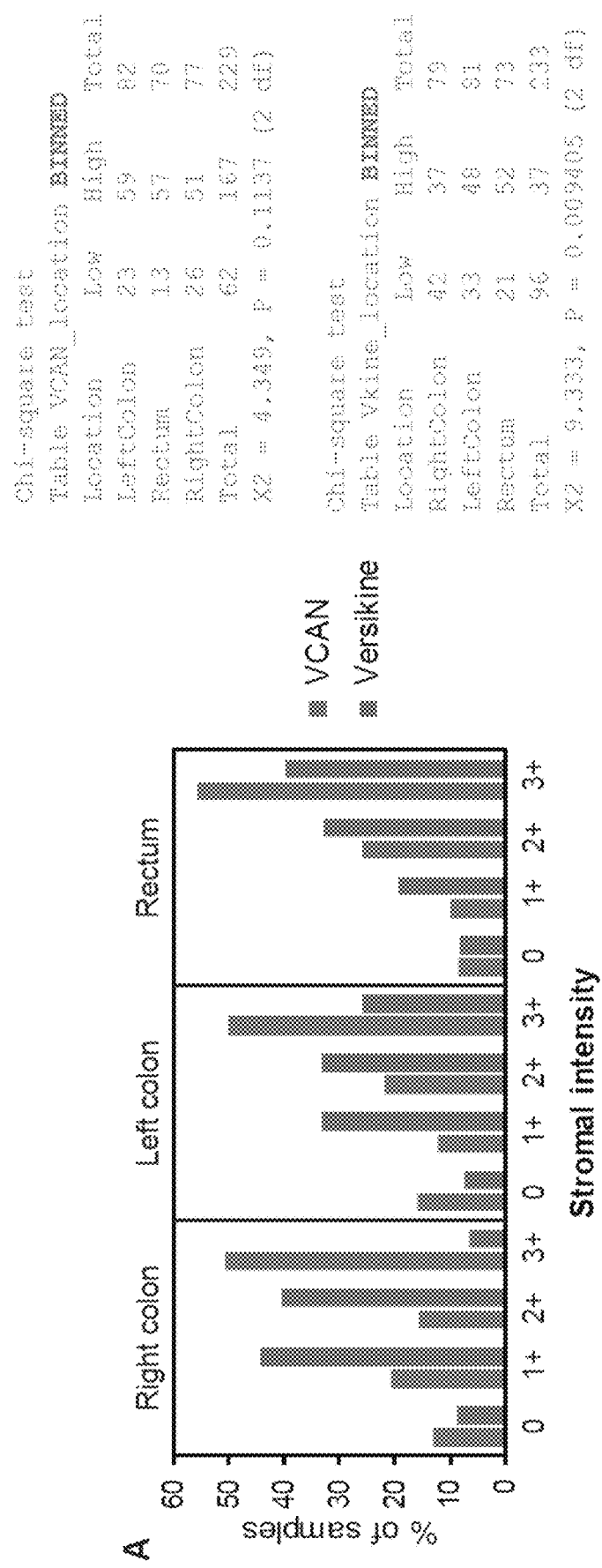
Figure 11:
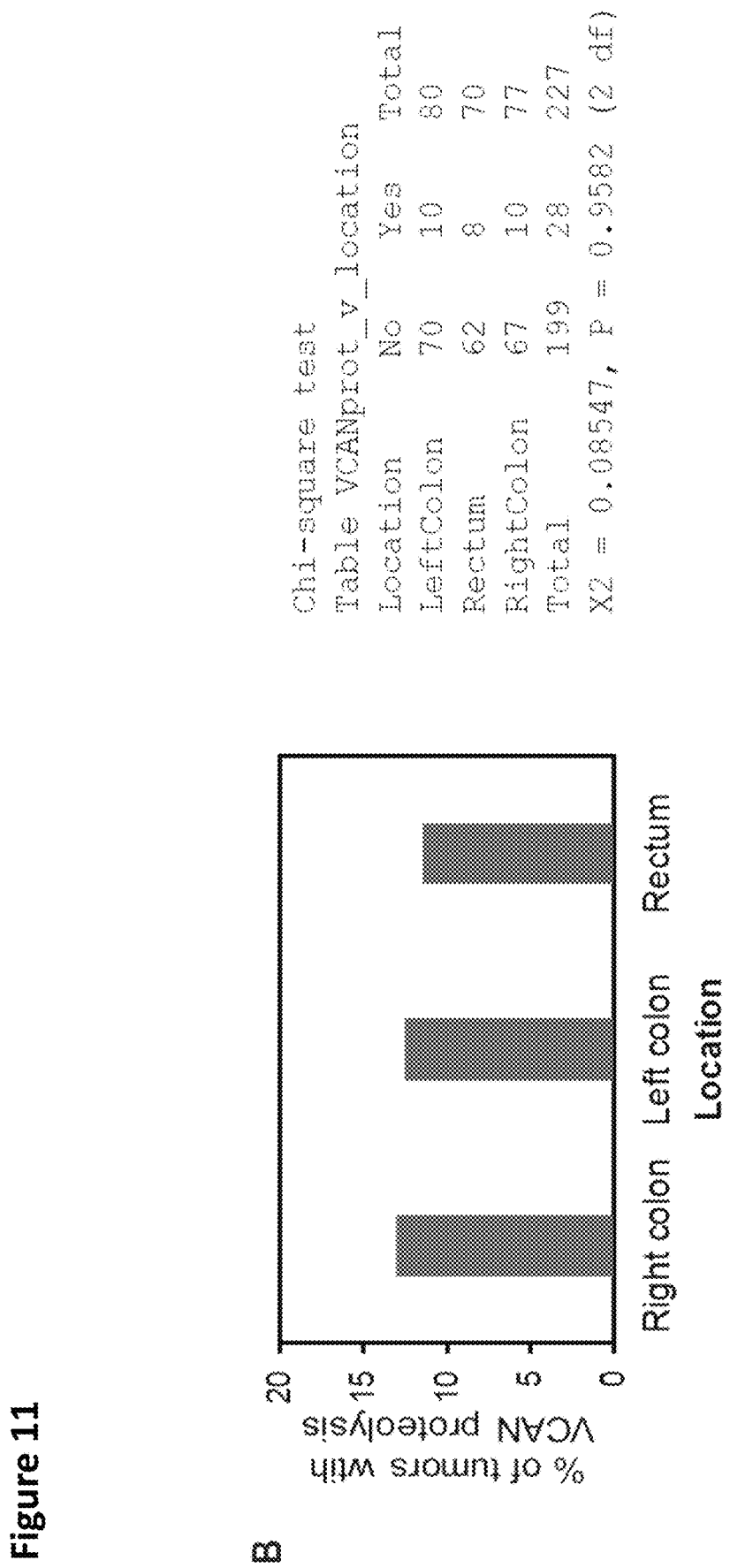
Figure 11:
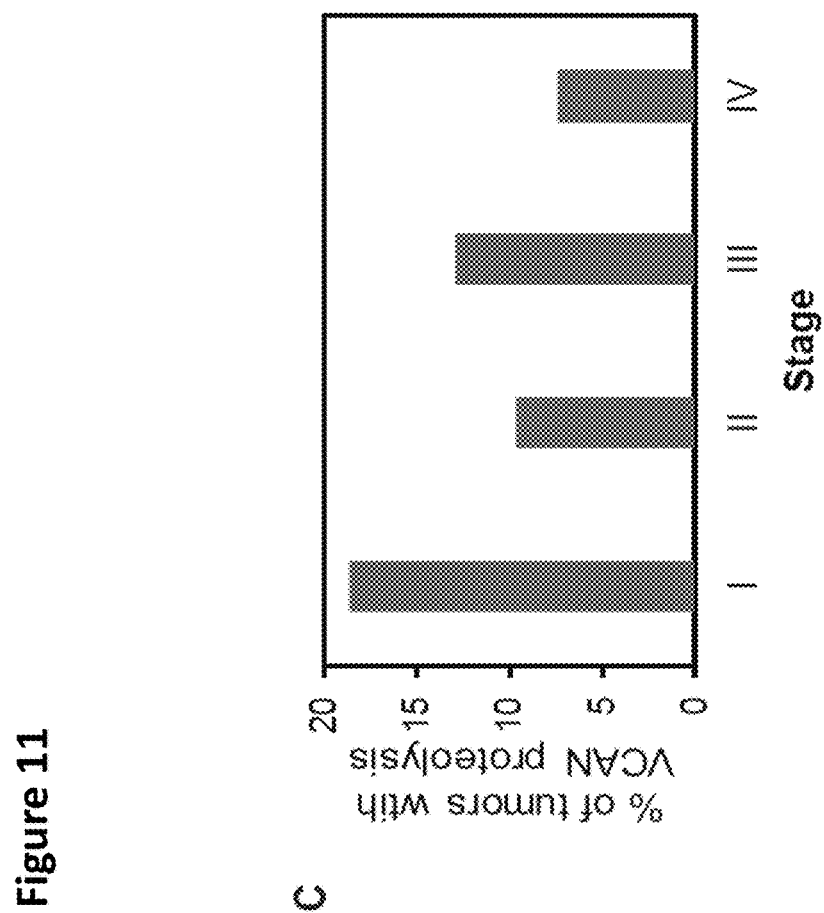

FIG. 11. VCAN and αDPEAAE staining across tumor locations and stages. There was no correlation between total VCAN staining and location of primary tumor (A). Increased αDPEAAE staining was observed in the rectum compared to the left or right colon (Chi-square test, p=0.009; A). Despite a greater staining for αDPEAAE being identified within the rectum, there was no significant correlation between the VCAN proteolysis-predominant classification and tumor location (Chi-square test, p=0.96; B). A trend toward an increased prevalence staining for the VCAN proteolysis-predominant classification was seen in colon cancers of earlier stage, albeit not statistically significant (Chi-square test, p=0.28; C).

Figure 12:
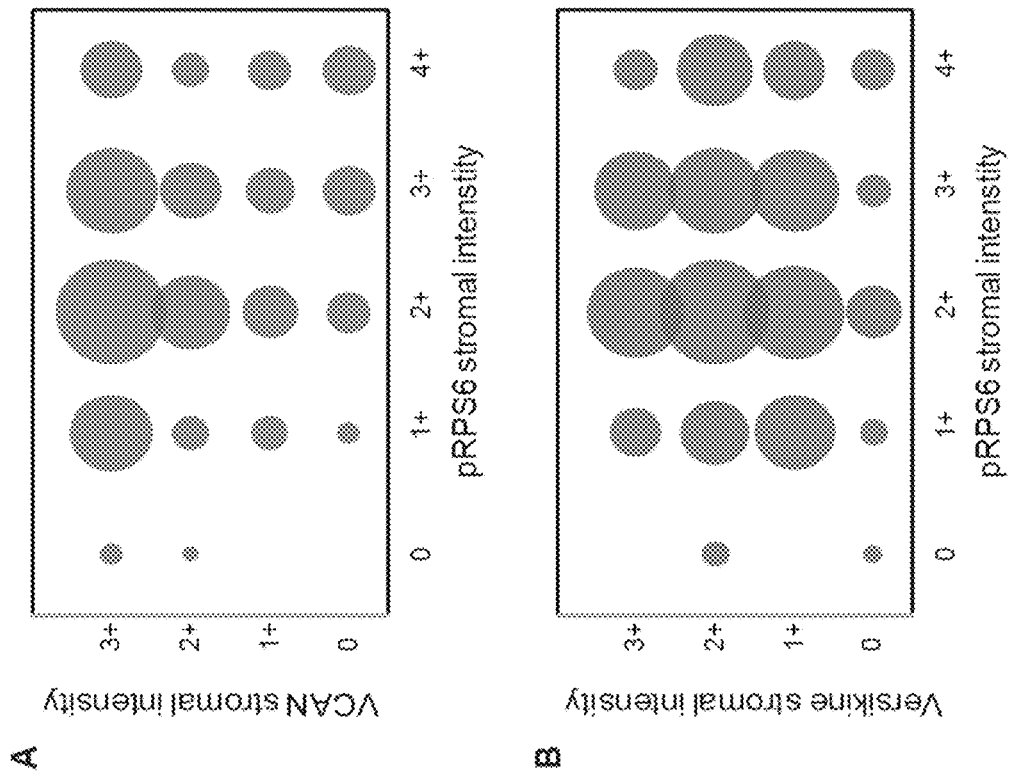
Figure 12:
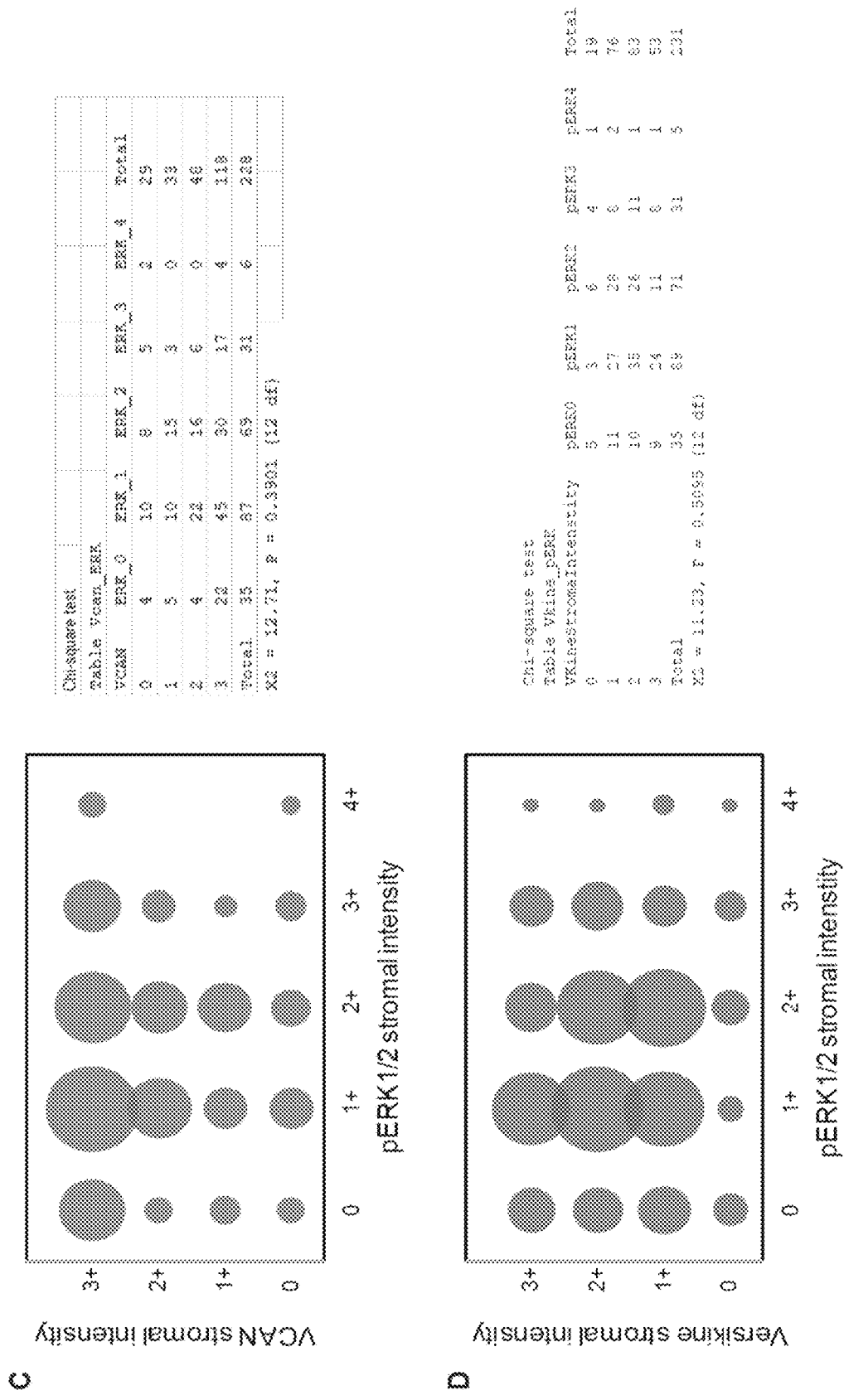

FIG. 12. Association of VCAN and αDPEAAE staining with phosphorylation of RPS6 and ERK1/2. There was not a significant correlation between stromal intensity of VCAN or αDPEAAE staining and phosphorylation of RPS6 (A and B) or phosphorylation of ERK1/2 (C and D).

Figure 13:
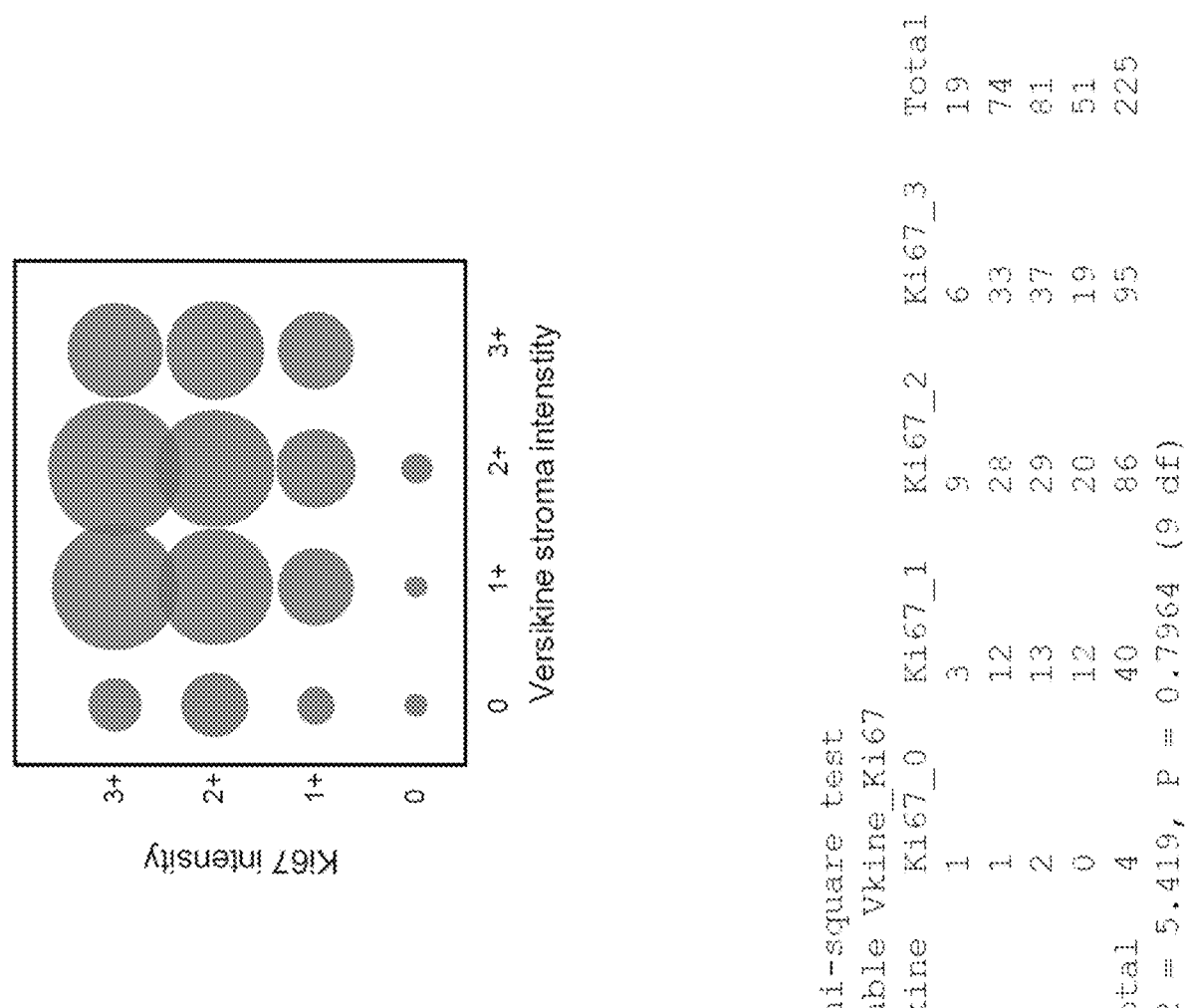

FIG. 13. αDPEAAE stromal intensity and cellular proliferation. Ki67 was staining was categorized by the percent of cells with nuclear staining for Ki67. No correlation was identified between αDPEAAE staining and the percent of Ki67 positive nuclei (Chi-square test, p=0.9).

DETAILED DESCRIPTION

The present invention is described herein using several definitions, as set forth below and throughout the application.

Definitions

Unless otherwise specified or indicated by context, the terms "a", "an", and "the" mean "one or more." For example, "a polypeptide" should be interpreted to mean "one or more polypeptides."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus ≥10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, a "subject" may be interchangeable with "patient" or "individual" and means an animal, which may be a human or non-human animal, in need of treatment. Non-human animals may include dogs, cats, horses, cows, pigs, sheep, and the like.

A "subject in need thereof" may include a patient having a disease, disorder, or condition that is characterized by the lack of, or by a deficient or impaired T-cell mediated immune response, which may include, but is not limited to a T-cell response characterized as a T-cell inflamed phenotype. A T-cell inflamed phenotype may include, but is not limited to a type 1 interferon signature (i.e., a type 1 interferon expression profile), expression of chemokines that attract T-cells such as $T_{regs}$ (i.e., FoxP3$^+$ cells) or CD8$^+$ T-cells into tumor sites (e.g., CCL2, CCL3, CCL, 4, CCL, 5, CCL22, CXCL9, ad CXCL10), expression of T-cell specific transcripts, and/or expression of macrophage-activation markers. Diseases characterized by the lack of, or by a deficient or impaired T-cell mediated immune response, may include but are not limited to cell proliferative diseases and disorders (e.g., cancer).

A "subject in need thereof" may include a subject having a cell proliferative disease or disorder such as cancer. Cancer types may include, but are not limited to adenocarcinoma, leukemia, lymphoma, melanoma, myeloma, sarcoma, and teratocarcinoma. Cancer types may include, but are not limited to cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus. A "subject in need thereof" may include a subject having a cancer that is characterized by a non-T-cell inflamed tumor microenvironment. (See Gajewski, "The Next Hurdle in Cancer Immunotherapy: Overcoming the Non-T-Cell-Inflamed Microenvironment," Seminars in Oncology, Vol. 42, No. 4, August 2015, pp 663-671, the content of which is incorporated herein by reference in its entirety).

Reference is made herein to polypeptides and pharmaceutical compositions comprising polypeptides such as versikine and variants of versikine. An exemplary polypeptide may comprise the amino acid sequence of any of SEQ ID NOs:1-27, or may comprises an amino acid sequence having at least about 80%, 90%, 95%, 96%, 97%, 98%, or 99% sequence identity to any of SEQ ID NOs:1-27. Variant polypeptides may include polypeptides having one or more amino acid substitutions, deletions, additions and/or amino acid insertions relative to a reference polypeptide. Also disclosed are nucleic acid molecules that encode the disclosed polypeptide (e.g., polynucleotides that encode the polypeptide of any of SEQ ID NOs:1-27 or variants thereof).

SEQ ID NOs:1-27 provide amino acid sequences as follows: SEQ ID NO:1—full length versican V1 including signal peptide sequence (i.e., aa 1-2339); SEQ ID NO:2—full length versican V1 minus signal peptide sequence (i.e., aa 21-2339); SEQ ID NO:3—full length versican V1 minus signal peptide sequence, plus N-terminal methionine; SEQ ID NO:4—non-versikine sequence of versican V1 (i.e., aa 442-2339); SEQ ID NO:5—full length versican including signal peptide sequence (i.e., aa 1-441); SEQ ID NO:6—full length versikine minus signal peptide sequence (i.e., aa 21-441); SEQ ID NO:7—full length versikine minus signal peptide sequence, plus N-terminal methionine; SEQ ID NO:8—Ig-like domain of versikine including signal peptide sequence (i.e., aa 1-146); SEQ ID NO:9—Ig-like domain of versikine minus signal peptide sequence (i.e., aa 21-146); SEQ ID NO:10—Ig-like domain of versikine minus signal peptide sequence, plus N-terminal methionine; SEQ ID NO:11—Linker domain 1 of versikine (i.e., aa 150-245); SEQ ID NO:12—Linker domain 1 of versikine plus N-terminal methionine; SEQ ID NO:13—Linder domain 2 of versikine (i.e., aa 251-347); SEQ ID NO:14—Linker domain 2 of versikine plus N-terminal methionine; SEQ ID NO:15—Portion of GAG-β domain in versikine (i.e., aa 349-441); SEQ ID NO:16—N-terminal portion of versikine including signal peptide sequence, Ig-like domain, and Linker domain 1 (i.e., aa 1-245); SEQ ID NO:17—N-terminal portion of versikine including Ig-like domain and Linker domain 1 (i.e., aa 21-245); SEQ ID NO:18—N-terminal portion of versikine including Ig-like domain and Linker domain 1 plus N-terminal methionine; SEQ ID NO:19—N-terminal portion of versikine including signal peptide sequence, Ig-like domain, Linker domain 1, and Linker domain 2 (i.e., aa 1-347); SEQ ID NO:20—N-terminal portion of versikine including Ig-like domain, Linker domain 1, and Linker domain 2 (i.e., aa 21-347); SEQ ID NO:21—N-terminal portion of versikine including Ig-like domain, Linker domain 1, and Linker domain 2, plus N-terminal methionine; SEQ ID NO:22—Internal portion of versikine including Linker domain 1 and Linker domain 2 (i.e., aa 150-347); SEQ ID NO:23—Internal portion of versikine including Linker domain 1 and Linker domain 2, plus N-terminal methionine (i.e., aa 150-347); SEQ ID NO:24—C-terminal portion of versikine including Linker domain 1, Linker domain 2, and portion of Gag-β domain (i.e., aa 150-441); SEQ ID NO:25—C-terminal portion of versikine including Linker domain 1, Linker domain 2, and portion of Gag-β domain, plus N-terminal methionine; SEQ ID NO:26—C-terminal portion of versikine including Linker domain 2 and portion of Gag-β domain (i.e., aa 251-441); SEQ ID NO:27—C-terminal portion of versikine including Linker domain 2 and portion of Gag-β domain, plus N-terminal methionine.

The disclosed versikine polypeptides or variant polypeptide preferably exhibit one or more biological activities that include inducing and/or potentiating a T-cell mediated immune response, and in particular, inducing and/or potentiating a T-cell inflamed phenotype. A T-cell inflamed phenotype may be characterized by a number of criteria, including but not limited to a type 1 interferon signature (i.e., a type 1 interferon expression profile), expression of chemokines that attract T-cells such as Tregs (i.e., FoxP3$^+$ cells) or CD8$^+$ T-cells into tumor sites (e.g., CCL2, CCL3, CCL, 4, CCL, 5, CCL22, CXCL9, ad CXCL10), expression of T-cell specific transcripts, and/or expression of macrophage-activation markers. (See, e.g., Gajewski, "The Next Hurdle in Cancer Immunotherapy: Overcoming the Non-T-Cell-Inflamed Tumor Microenvironment, Seminars in Oncology, Vol. 42, No. 4, August 2015, pp. 663-671; Zitvogel et al., "Type 1 interferons in anticancer immunity," Nature Reviews, Vol. 15, July 2015, pp. 405-414; and Harlin et al., "Chemokine Expression in Melanoma Metastases Associated with CD8+ T-cell Recruitment," Cancer Res. 2009 Apr.

1; 69(7)). A type 1 interferon signature can be used to characterize a number of diseases and disorders, including cell proliferative diseases and disorders as well as other diseases and disorder. (See, e.g., Gajewski, "The Next Hurdle in Cancer Immunotherapy: Overcoming the Non-T-Cell-Inflamed Tumor Microenvironment, Seminars in Oncology, Vol. 42, No. 4, August 2015, pp. 663-671; Zitvogel et al., "Type 1 interferons in anticancer immunity," Nature Reviews, Vol. 15, July 2015, pp. 405-414Häupl et al., "The type 1 interferon signature: facts, fads and fallacies," Ann. Rheum Dis 2011; 70:A24; Ronnblom et al., "The interferon signature in autoimmune diseases," Curr Opin. Rheumatol. 2013 March; 25(2):248-53; Ferreira et al., "A type 1 interferon transcriptional signature precedes autoimmunity in children genetically at risk for type 1 diabetes," Diabetes, 2014 July; 63(7):2538-50; Cornabella et al., "A type 1 interferon signature in monocytes is associated with poor response to interferon-beta in multiple sclerosis," Brain 2009 December; 132(Pt 12):3353-65; the contents of which are incorporated herein by reference in their entireties).

The disclosed polynucleotides encoding the disclosed polypeptides may be present in a replication vector and/or expression vector. Suitable vectors may include bacterial, plant, fungal, insect, or animal host cell replication and/or expression vectors that express the disclosed versikine polypeptides or variants thereof. Vectors may be used to transform appropriate host cells (e.g., *E. coli*). The transformed host cell may be cultivated or fermented such that the polypeptide is expressed constitutively or after adding a reagent that induces expression (e.g., via an inducible promoter). Expression vectors as contemplated herein may include control sequences that modulate expression of the encoded polypeptide. Expression control sequences may include constitutive or inducible promoters (e.g., T3, T7, Lac, trp, or phoA), ribosome binding sites, or transcription terminators.

The vectors disclosed herein may be utilized to transform host cells. Suitable host cells include bacterial, plant, fungal, insect, or animal host cell. Suitable bacteria include, but are not limited to: Gram-negative bacteria such as *Escherichia* species (e.g., *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., in particular *Bacillus subtlis*). Suitable fungal cells may include yeast (e.g., *Saccharomyces cerevisiae*).

Also disclosed are methods for expressing, preparing, isolating, separating, or purifying the disclosed versikine polypeptides or variants thereof. In some embodiments, the methods may be utilized to produce the versikine polypeptides as disclosed herein. The steps of the methods may include: (i) cultivating or fermenting a transformed host cell (e.g., a bacterial host cell as contemplated herein) which comprises an expression vector (as contemplated herein) which in turn comprises a nucleic acid molecule encoding the disclosed versikine polypeptides or variants thereof (as contemplated herein), wherein cultivation occurs under conditions which cause expression of the versikine polypeptides; and (ii) isolating, separating, or purifying the versikine polypeptide. The transformed bacteria may be cultivated or fermented using methods known in the art in order to express the versikine polypeptide. An exemplary isolation, separation, or purification method may include one or more of the following steps: a cell disruption step, a clarification step (e.g., via centrifugation or filtration), a chromatographic separation step, a dialysis step, and a precipitation step.

The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

The amino acid sequences contemplated herein may include conservative amino acid substitutions relative to a reference amino acid sequence. For example, a variant versikine polypeptide may include conservative amino acid substitutions relative to the natural versikine polypeptide. "Conservative amino acid substitutions" are those substitutions that are predicted to interfere least with the properties of the reference polypeptide. In other words, conservative amino acid substitutions substantially conserve the structure and the function of the reference protein. Conservative amino acid substitutions may include:

| Original Residue | Conservative Substitutions |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least (or no more than) 5, 10, 15, 20, 25, 30, 40, 50, 60, 70, 80, 90, 100, 150, 250, or 500 contiguous nucleotides or contiguous amino acid residues of a reference polynucleotide or reference polypeptide, respectively. A fragment may comprise a range of contiguous nucleotides or contiguous amino acid residues of a reference polynucleotide or reference polypeptide, respectively, bounded by endpoints selected from any of 5, 10, 15, 20, 25, 30, 40, 50, 60, 70, 80, 90, 100, 150, 250, or 500 contiguous nucleotides or contiguous amino acid residues, respectively (e.g., a peptide fragment having 100-150 contiguous amino acid residues of a reference polypeptide). Fragments may be preferentially selected from certain regions of a molecule. The term "at least a fragment" encompasses the full length polynucleotide or full length polypeptide.

Fusion proteins also are contemplated herein. A "verskine fusion protein" refers to a protein formed by the fusion (e.g., genetic fusion) of at least one molecule of versikine (or a fragment or variant thereof) to at least one molecule of a heterologous protein (or fragment or variant thereof), which may include a therapeutic protein. A versikine fusion protein comprises at least a fragment or variant of the heterologous protein and at least a fragment or variant of versikine, which are associated with one another, preferably by genetic fusion (i.e., the versikine fusion protein is generated by translation of a nucleic acid in which a polynucleotide encoding all or a portion of the heterologous protein is joined in-frame with a polynucleotide encoding all or a portion of versikine or a fragment or variant thereof). The heterologous protein and versikine protein, once part of the versikine fusion protein, may each be referred to herein as a "portion", "region" or "moiety" of the versikine fusion protein (e.g., a "a heterologous protein portion" or a "versikine protein portion").

Conjugate proteins also are contemplated herein. A "versikine conjugate protein" refers to a protein formed by the conjugation (i.e., covalently bonding) of at least one molecule of versikine (or a fragment or variant thereof) to at least one molecule of a heterologous protein (or fragment or variant thereof), which may include a therapeutic protein. A versikine conjugate protein comprises at least a fragment or variant of the heterologous protein and at least a fragment or variant of versikine, which are associated with one another by covalent bonding. The heterologous protein and versikine protein, once part of the versikine conjugate protein, may each be referred to herein as a "portion," "region" or "moiety" of the versikine conjugate protein (e.g., "a heterologous protein portion" or a "versikine protein portion").

Suitable heterologous proteins for the contemplated versikine fusion protein and versikine conjugate proteins may include therapeutic antibodies or antigen-binding fragments thereof. Suitable antibodies may include, but are not limited to, antibodies that bind to the protein CD20 (e.g., rituximab or an antigen-binding fragments thereof that binds the protein CD20), antibodies that bind to the protein CD38 (e.g., daraturumab or an antigen-binding fragment thereof that binds the protein CD38), antibodies that bind to the protein CD30 (e.g., brentuximab or an antigen-binding fragment thereof that binds the protein CD30), antibodies that bind to the protein CD19 (e.g., blinatumomab or an antigen-binding fragment thereof that binds the protein CD19), antibodies that bind to the protein CD40 (e.g. ipilimumab or an antigen-binding fragment thereof that binds CD40), antibodies that bind to the protein PD-1 (e.g., nivolumab or an antigen-binding fragment thereof that binds PD-1). Suitable heterologous proteins may also include ligands for receptor present on T-cells and immunoadhesins (e.g., immunoadhesins that target any of CD20, CD38, CD30, CD19, CD40, and/or PD-1).

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide. For example, a variant of versikine may exhibit or more biological activities associated with versikine, including inducing of a type 1 interferon signature.

The disclosed polypeptides may be modified so as to comprise an amino acid sequence or modified amino acids, such that the disclosed polypeptides cannot be said to be naturally occurring. In some embodiments, the disclosed polypeptides are modified and the modification is selected from the group consisting of acylation, acetylation, formylation, lipolylation, myristoylation, palmitoylation, alkylation, isoprenylation, prenylation, and amidation. An amino acid in the disclosed polypeptides may be thusly modified, but in particular, the modifications may be present at the N-terminus and/or C-terminus of the polypeptides (e.g., N-terminal acylation or acetylation, and/or C-terminal amidation). The modifications may enhance the stability of the polypeptides and/or make the polypeptides resistant to proteolysis.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below).

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth"). Preferably, a 5-fold, or more preferably a 10-fold or greater, enhancement in an immune response may be obtained by administering the polypeptides and pharmaceutical compositions disclosed herein. In some embodiments, potentiating or enhancing an immune response means overcoming a non-T-cell-inflamed tumor microenvironment in a subject having cancer (e.g., by increasing the number of T-cells that are infiltrating the tumor, by increasing the number of cells that are exhibiting a type 1 interferon signature, and/or by increasing the number of cells that are expressing macrophage-activation markers).

The disclosed pharmaceutical composition may comprise the disclosed versikine polypeptides and variants at any suitable dose. Suitable doses may include, but are not limited to, about 0.01 µg/dose, about 0.05 µg/dose, about 0.1 µg/dose, about 0.5 µg/dose, about 1 µg/dose, about 2 µg/dose, about 3 µg/dose, about 4 µg/dose, about 5 µg/dose, about 10 µg/dose, about 15 µg/dose, about 20 µg/dose, about 25 µg/dose, about 30 µg/dose, about 35 µg/dose, about 40 µg/dose, about 45 µg/dose, about 50 µg/dose, about 100 µg/dose, about 200 µg/dose, about 500 µg/dose, or about 1000 µg/dose. Suitable doses may be within dose ranges bounded by any of about 0.01 µg/dose, about 0.05 µg/dose, about 0.1 µg/dose, about 0.5 µg/dose, about 1 µg/dose, about 2 µg/dose, about 3 µg/dose, about 4 µg/dose, about 5 µg/dose, about 10 µg/dose, about 15 µg/dose, about 20 µg/dose, about 25 µg/dose, about 30 µg/dose, about 35 µg/dose, about 40 µg/dose, about 45 µg/dose, about 50 µg/dose, about 100 µg/dose, about 200 µg/dose, about 500 µg/dose, or about 1000 µg/dose (e.g., about 50 µg/dose to about 100 µg/dose)

The disclosed versikine polypeptides and variants may be administered at any suitable dose level. In some embodiments, a subject in need thereof is administered a versikine polypeptide or variant thereof at a dose level of from about 1 ng/kg up to about 2000 ng/kg. In some embodiments, the versikine polypeptide or variant thereof is administered to the subject in need thereof at a dose level of at least about 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg. In other embodiments, the versikine polypeptide or variant thereof is administered to the subject in need thereof at a dose level of less than about 2000 ng/kg, 1000 ng/kg, 500 ng/kg, 200 ng/kg, 100 ng/kg, 50 ng/kg, 20 ng/kg, 10 ng/kg, 5 ng/kg, 2 ng/kg, or 1 ng/kg. In further embodiments, the versikine polypeptide or variant thereof is administered to a subject in need thereof within a dose level range bounded by any 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg (e.g., a dose level range of 100 ng/kg to 200 ng/kg).

The disclosed versikine polypeptides and variants may be administered under any suitable dosing regimen. Suitable dosing regimens may include, but are not limited to, daily regimens (e.g., 1 dose/day for 1, 2, 3, 4, 5, 6, 7 or more days), twice daily regimens (e.g., 2 doses/day for 1, 2, 3, 4, 5, 6, 7 or more days), and thrice daily regiments (e.g., 3 doses/day for 1, 2, 3, 4, 5, 6, 7 or more days). Suitable regiments also may include dosing every other day, 3 times/week, once a week, for 1, 2, 3, 4, or more weeks.

The disclosed versikine polypeptides and variants (or pharmaceutical compositions comprising the disclosed versikine polypeptides and variant) may be administered to a subject in need thereof by any suitable route. In some embodiments, the disclosed versikine polypeptides and variant are administered to a subject in need thereof via an injectable delivery route selected from the group consisting of intradermal, intramuscular, intraperitoneal, intravenous, subcutaneous, intratumorally, or epidural routes. In another embodiment, the disclosed versikine polypeptides and variant are administered to a subject near a site of a tumor or cancer. The disclosed versikine polypeptides and variants may be administered to cells or tissue that has been explanted from a subject. For example, the explanted cells or tissue may be contacted or treated with the disclosed versikine polypeptides and variants ex vivo, and after treatment/contact, the explanted cells or tissue may be administered to the patient, for example, but re-infusion and/or transplant.

Use of Versikine and Variants Thereof in Treatment Methods

Disclosed are methods and compositions for inducing and/or potentiating an immune response. The present inventors have determined that versikine can be administered in order to induce and or potentiate a T-cell mediated immune response, which may be characterized as a T-cell inflamed phenotype. As such, the inventors have determined that versikine may be administered to potentiate T-cell activating immunotherapies.

The disclosed methods include methods for inducing and/or potentiating an immune response in a subject in need thereof, including a T-cell mediated immune response. The disclosed methods may include administering to the subject in need thereof a pharmaceutical composition comprising an effective amount of versikine or a variant thereof that induces and/or potentiates the T-cell mediated immune response. The pharmaceutical composition may be administered by any suitable route including, for example, systemically (e.g., intervenously) or by injecting the pharmaceutical composition directly into tissue (e.g., tumor tissue).

In some embodiments, the T-cell mediated immune response induced and/or potentiated in the disclosed methods may be characterized by a type 1 interferon signature (i.e., type 1 interferon expression profile). As such, in the disclosed methods versikine or a variant thereof may be administered in order to induce and/or potentiate expression of one or more genes whose expression is observed to be induced by type 1 interferon. In some embodiments, the enhanced expression is observed relative to a baseline or control of one or more genes encoding any of IF16, MX1, XAF1, IFITM1, OAS3, IFI44L, TRIM22, STAT1, IFI44, CCL2, MX2, IFIT1, OAS2, SIGLEC1, TTSAD2, OASL, SIGLEC11, IFITM1, and ISG15. Expression may be measured and assessed by methods known in the art, including methods for detecting mRNA (e.g., via RT-PCR) and methods for detecting encoded proteins (e.g., via immunoassay).

The disclosed versikine polypeptides and variants may be administered in order to induce production of other cytokines. In some embodiments, the disclosed versikine polypeptides and variants may be administered in order to induce or enhance production of IL1β, IL6, or both (e.g., by macrophages). Induction or enhanced production of cytokines may be measured and assessed by methods known in the art (e.g., via immunoassays or via assays that measure biological activity of the cytokines).

The disclosed versikine polypeptides and variants may be administered in order to induce expression of other proteins. In some embodiments, the disclosed versikine polypeptides and variants may be administered in order to induce expression of one or more of EBI3, IRF8, and IL12p40. Expression may be measured and assessed by methods known in the art, including methods for detecting mRNA (e.g., via RT-PCR) and methods for detecting encoded proteins (e.g., via immunoassay).

The disclosed versikine polypeptides and variants may be administered in order to induce phosphorylation of other proteins. In some embodiments, the disclosed versikine polypeptides and variants may be administered to induce phosphorylation of one or more of JNK, p38-MAPK, and AKT.

The disclosed methods include administering versikine polypeptides to a subject in need thereof and also administering variants of versikine to a subject in need thereof. Typically, the variants exhibit one or more biological activities associated with versikine, such as induction of a T-cell mediated immune response. In some embodiments, the versikine polypeptide or variant thereof comprises, consists essentially of, or consists of the amino acid sequence of any of SEQ ID NOs:1-27 or an amino acid sequence having a least about 80%, 85%, 90%, 95%, 96%, 97%, 98%, or 99% sequence identity to any of SEQ ID NOs:1-27.

The disclosed versikine polypeptides and variants thereof optionally comprise an N-terminal methionine which optionally may not be present in naturally occurring versikine. In some embodiments, the disclosed versikine polypeptides and variants thereof may comprise, consist essentially of, or consist of the amino acid sequence of any of SEQ ID NOs:3-27 or an amino acid sequence having a least about 80%, 85%, 90%, 95%, 96%, 97%, 98%, or 99% sequence to any of SEQ ID NOs:3-27, wherein the versikine polypeptides or variants thereof comprise a non-naturally occurring N-terminal methionine. Exemplary polypeptides include polypeptides comprising, consisting essentially of, or consisting of the amino acid sequence of any of SEQ ID NOs:3, 7, 10, 12, 14, 18, 21, 23, 25 and 27.

The disclosed versikine polypeptides and variants thereof may comprise, consist essentially of, or consist of a fragment of a reference polypeptide. In some embodiments, the disclosed versikine polypeptides and variants thereof comprise, consist essentially of, or consist of a fragment of any of SEQ ID NOs:1-27. In some embodiments, the disclosed versikine polypeptides and variants thereof do not comprise the amino acid sequence of SEQ ID NOs:4 or 8-27. In embodiments where the versikine polypeptides and variants thereof comprise a fragment of a reference polypeptide that does not include the naturally occurring N-terminal methionine, the versikine polypeptides and variants thereof may be modified to include a non-naturally occurring N-terminal methionine.

The disclosed versikine polypeptides and variants thereof may comprise post-translational modifications or may lack post-translation modifications. In some embodiments, the disclosed versikine polypeptides and variants thereof do not have any chondroitin sulfate side chains. In other embodiments, the disclosed versikine polypeptides and variants thereof include one or more amino acid modifications selected from the group consisting of acylation (e.g., N-terminal acylation), acetylation (e.g., N-terminal acetylation), formylation, lipolylation, myristoylation, palmitoylation, alkylation, isoprenylation, prenylation, pegylation, and amidation (e.g., C-terminal amidation).

The disclosed versikine polypeptides and variants thereof may be modified to replace a natural amino acid residue by an unnatural amino acid. Unnatural amino acids may include, but are not limited to an amino acid having a D-configuration, an N-methyl-α-amino acid, a non-proteogenic constrained amino acid, or a β-amino acid.

The disclosed versikine polypeptides and variants thereof may be modified in order to increase the stability of the versikine polypeptides and variants thereof in plasma. For example, the disclosed peptides may modified in order to make the versikine polypeptides and variants thereof resistant to peptidases. The disclosed versikine polypeptides and variants thereof may be modified to replace an amide bond between two amino acids with a non-amide bond. For example, the carbonyl moiety of the amide bond can be replaced by $CH_2$ (i.e., to provide a reduced amino bond: —$CH_2$—NH—). Other suitable non-amide replacement bonds for the amide bond may include, but are not limited to: an endothiopeptide, —C(S)—NH, a phosphonamide, —P(O)OH—NH—), the NH-amide bond can be exchanged by O (depsipeptide, —CO—O—), S (thioester, —CO—S—) or $CH_2$ (ketomethylene, —CO—$CH_2$—). The peptide bond can also be modified as follows: retro-inverso bond (—NH—CO—), methylene-oxy bond (—$CH_2$—), thiomethylene bond (—$CH_2$—S—), carbabond (—$CH_2$—$CH_2$—), hydroxyethylene bond (—CHOH—$CH_2$—) and so on, for example, to increase plasma stability of the versikine polypeptides and variants thereof (notably towards endopeptidases).

The disclosed versikine polypeptides and variants thereof may include a non-naturally occurring N-terminal and/or C-terminal modification. For example, the N-terminal of the disclosed versikine polypeptides and variants thereof may be modified to include a N-acylation or a N-pyroglutamate modification (e.g., as a blocking modification). The C-terminal end of the disclosed versikine polypeptides and variants thereof may be modified to include a C-amidation.

The disclosed versikine polypeptides and variants thereof may include an N-terminal esterification (e.g., a phosphoester modification) or a pegylation modification, for example, to enhance plasma stability (e.g. resistance to exopeptidases) and/or to reduce immunogenicity.

The disclosed versikine polypeptides and variants thereof may be fused to additional functional polypeptide domains. In some embodiments, the disclosed versikine polypeptides and variants thereof are fused to an antibody or an antigen-binding domain thereof (e.g., one or more scFv or other antigen-binding domains). Optionally, the antigen-binding domain binds to an epitope of a tumor antigen and the versikine/antigen-binding fusion polypeptide is administered to a subject having a cancer for which the tumor antigen is associated in order to target the versikine/antigen-binding fusion polypeptide to the subject's tumor.

The disclosed versikine polypeptides and variants thereof may be conjugated to a resin or a solid support. For example, the disclosed versikine polypeptides and variants thereof maybe conjugated via there N-terminus and/or C-terminus to a solid support, either directly or via a linking moiety that conjugates the peptides to the resin or the solid support. Solid supports may include microparticles or nanoparticles such as polymeric microparticles or polymeric nanoparticles comprising a biodegradable polymer (e.g., poly(lactic-co-glycolic acid) (PLGA) polylactic acid, and poly(caprolactone)).

The disclosed versikine polypeptides and variants thereof may be formulated as a pharmaceutical composition for use in the methods disclosed herein. Typically, the pharmaceutical compositions contemplated herein will comprise an effective amount of a versikine polypeptide or variant thereof for inducing a T-cell mediated immune response in a subject after the pharmaceutical composition is administered to the subject or in cells or tissues explanted from the subject after the cells or tissues are contacted with the pharmaceutical composition.

The disclosed methods also may include administering the pharmaceutical composition comprising an effective amount of versikine or a variant thereof that induces a T-cell mediated immune response to explanted cells from a subject, for example, in a method in which the explanted cells are treated with the pharmaceutical composition ex vivo. The explanted cells thus treated may then be administered back to the subject, for example, by re-infusion. The explanted cells may include immune cells (e.g., T-cells or dendritic cells), which optionally are treated, contacted, or primed with an antigen (e.g., a tumor antigen), either before, concurrently with, or after treatment with the pharmaceutical composition comprising an effective amount of versikine or a variant thereof. The explanted cells may include tumor cells.

The disclosed methods include methods for treating cell proliferative diseases and disorders such as cancers in a subject by administering to the subject a pharmaceutical composition comprising an effective amount of versikine or a variant thereof that induces a T-cell mediated immune response. As such, cancers treated by the disclosed methods may include cancers that are characterized the absence of, or by a defective or impaired T-cell mediated response (e.g., cancers that are characterized the absence of, or by a defective T-cell inflamed phenotype). Cancers treated by the presently disclosed methods may include tissue type cancers selected from, but not limited to adenocarcinoma, leukemia, lymphoma, melanoma, myeloma, sarcoma, and teratocarcinoma. Cancers treated by the presently disclosed methods may include organ type cancers selected from, but not limited to the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus. In particular, a subject in need thereof may include a subject having a hematological malignancy, including but not limited to myeloma.

In the disclosed methods for treating cancer in a subject, the methods further may include administering to the subject cancer therapy before, concurrently with, or after administering the pharmaceutical composition comprising versikine or the variant thereof. Suitable cancer therapies may include, but are not limited to, administering chemotherapeutic agents. Suitable chemotherapeutic agents for administration in the disclosed methods may include, but are not limited to Abitrexate, Adcetris, Ambochlorin, Aredia (Pamidronate Disodium), Arranon, Asparaginase Erwinia chrysanthemi, Becenum (Carmustine), Beleodaq, Belinostat, Bendamustine Hydrochloride, Bexxar, BiCNU (Carmustine), Blenoxane, Bleomycin, Blinatumomab, Blincyto, Bortezomib, Brentuximab Vedotin, Carfilzomib, Carmubris (Carmustine), Carmustine, Cerubidine, Chlorambucil, Clafen (Cyclophosphamide), Clofarex, Clolar, Cyclophosphamide, Cytarabine, Cytarabine Liposome, Cytosar-U, Cytoxan (Cyclophosphamide), Daratumumab, Darzalex (Daratumumab), Dasatinib, Daunorubicine Hydrochloride, Denileukin Diftitox, DepoCyt, Dexamethasone, Docetaxel, Doxil (Doxorubicin Hydrochloride Liposome), Doxorubicin Hydrochloride Liposome, Dox-SL (Doxorubicin Hydrochloride Liposome), Elotuzumab, Empliciti (Elotuzumab), Epirubicin, Erwinaze, Estramustine, Etoposide, Evacet (Doxorubicin Hydrochloride Liposome), Farydak (Panobinostat), Folex, Folex PFS, Folotyn, Ibrutumomab Tiuxetan, Ibrutinib, Iclusig, Idarubicin, Idelalisib, Imatinib Mesylate, Imbruvica, Intron A, Irinotecan, Istodax, Ixabepilone, Ixazomib Citrate, Kyprolis (Carfilzomib), Lenalidomide, Leukeran, Linfolizin, LipoDox (Doxorubicin Hydrochloride Liposome), Marqibo, Mechlorethamine Hydrochloride, Mercaptopurine, Methotrexate, Methotrexate LPF, Mexate, Mexate-AQ, Mitoxantrone, Mozobil (Plerixafor), Mustargen, Nelarabine, Neosar (Cyclophosphamide), Ninlaro (Ixazomib Citrate), Oncaspar, Ontak, Paclitaxel, Pamidronate Disodium, Panobinostat, Pegaspargase, Plerixafor, Pomalidomide, Pomalyst (Pomalidomide), Ponatinib Hydrochloride, Pralatrexate, Prednisone, Purinethol, Purixan, Recombinant Interferon Alfa-2b, Revlimid (Lenalidomide), Rituxanab, Romidepsin, Rubidomycin, Sprycel, Synovir (Thalidomide), Tarabiune PFS, Teniposide, Thalidomide, Thalomid (Thalidomide), Topotecan, Tositumomab, Treanda, Velban, Velcade (Bortezomib), Vinblastine Sulfate, Vincasar PGS, Vincristine Sulfate, Vincristine Sulfate Liposome, Vinorelbine, Vorinostat, Zevalin, Zoledronic Acid, Zolinza, Zometa (Zoledronic Acid), and Zydelig.

Other suitable cancer therapies that may be administered before, concurrently with, or after administering the pharmaceutical composition comprising versikine or the variant thereof may include therapies in which oncolytic viruses are administered, therapies in which immunomodulatory drugs are administered, therapies in which anthracyclines are administered, and therapies in which check-point blockers are administered. Other suitable cancer therapies that may be administered before, concurrently with, or after administering the pharmaceutical composition comprising versikine or the variant thereof may include therapies in which chimeric antigen receptor (CAR) T-cells are administered, therapies in which tumor infiltrating lymphocyte (TIL) are administered. Other suitable cancer therapies that may be administered before, concurrently with, or after administering the pharmaceutical composition comprising versikine or the variant thereof may include radiation therapy.

Also disclosed are methods for determining whether a subject will benefit from a method that includes administering to the subject a pharmaceutical composition comprising an effective amount of versikine or a variant thereof that induces a T-cell mediated immune response. The methods may include determining the concentration of versikine in a biological sample from the subject (e.g., a blood product), and if the determined level is determined to be below a selected baseline, then administering the pharmaceutical composition comprising versikine or the variant thereof. Suitable blood products as biological samples may include blood itself, plasma, and serum. Suitable tissue samples as biological samples may include biopsies, for example, from a tumor. Immunoassays as known in the art may be utilized to determine the concentration of versikine in the biological sample.

Also disclosed are kits comprising components that optionally may be utilized to perform the methods disclosed herein. The kits may include one or more of (a) versikine or a variant thereof, where the versikine or the variant thereof optionally is provided as a pharmaceutical composition; and (b) a reagent for detecting the concentration of versikine in a biological sample (e.g., an anti-versikine antibody which optionally is labelled with a detectable label). The kit optionally may include implements for administering the versikine or variant thereof (e.g., a syringe/needle type implement). The kit optionally may include an immunoassay for detecting versikine in a biological sample, for example, where the reagent for detecting the concentration of versikine in a biological sample is an anti-versikine antibody. The anti-versikine antibody may be labelled, or optionally, the kit may include a labelled secondary antibody that binds to the anti-versikine antibody, which functions as the primary antibody. Suitable labels may include fluorescent labels, chemiluminescent labels, enzyme labels, radio labels, and the like.

Also disclosed are isolated polynucleotides encoded any of the versikine polypeptides and variants disclosed herein. The isolated polynucleotide may be present in vectors for replication of the polynucleotides or for expression of the encoded polypeptides, for example, where the polynucleotides are operably linked to a promoter, which optionally may be an inducible promoter. Also disclosed are isolated cells that comprise the isolated polynucleotides, particular the isolated polynucleotides as present in the disclosed vectors. Isolated cells that comprise vectors for expression of the encoded versikine polypeptides and variants may be cultured in methods in order to produce the encoded versikine polypeptides and variants.

ILLUSTRATIVE EMBODIMENTS

The following embodiments are illustrative and are not intended to limit the scope of the claimed subject matter.

Embodiment 1

A method for inducing and/or potentiating a T-cell mediated immune response in a subject in need thereof, the method comprising administering to the subject or to explanted cells of the subject a pharmaceutical composition comprising an effective amount of versikine or a variant thereof that induces and/or potentiates the T-cell mediated immune response.

Embodiment 2

The method of embodiment 1, wherein the T-cell mediated immune response is characterized by a type 1 interferon signature.

Embodiment 3

The method of embodiment 2, wherein the type 1 interferon signature is characterized by increased expression of one or more of IL1β, IL6, EBI3, IRF8, IL12p40, IF16, MX1, XAF1, IFITM1, OAS3, IFI44L, TRIM22, STAT1, IFI44, CCL2, MX2, IFIT1, OAS2, SIGLEC1, TTSAD2, OASL, SIGLEC11, IFITM1, and ISG15.

Embodiment 4

The method of embodiment 2 or 3, wherein the type 1 interferon signature is characterized by increased phosphorylation of one or more of JNK, p38-MAPK, and AKT.

Embodiment 5

The method of any of the foregoing embodiments, wherein the variant comprises the amino acid sequence of any of SEQ ID NOs:1-27 or an amino acid sequence having a least about 80% sequence identity to any of SEQ ID NOs:1-27.

Embodiment 6

The method of any of the foregoing embodiments, wherein the variant comprises an N-terminal methionine.

Embodiment 7

The method of any of the foregoing embodiments, wherein the variant comprises a fragment of any of SEQ ID NOs:1-27.

Embodiment 8

The method of any of the foregoing embodiments, wherein the variant does not comprise the amino acid sequence of SEQ ID NOs:4 or 8-27.

Embodiment 9

The method of any of the foregoing embodiments, wherein the variant does not have any chondroitin sulfate side chains.

Embodiment 10

The method of any of the foregoing embodiments, wherein the variant has one or more amino acid modifications selected from the group consisting of acylation (e.g., N-terminal acylation), acetylation (e.g., N-terminal acetylation), formylation, lipolylation, myristoylation, palmitoylation, alkylation, isoprenylation, prenylation, and amidation (e.g., C-terminal amidation).

Embodiment 11

The method of any of the foregoing embodiments, wherein the variant comprises a fused antigen-binding domain.

Embodiment 12

The method of embodiment 11, wherein the antigen-binding domain binds to an epitope of a tumor antigen.

Embodiment 13

The method of any of the foregoing embodiments, wherein administering comprising intravenously administering to the subject the pharmaceutical composition comprising an effective amount of versikine or a variant thereof.

Embodiment 14

The method of any of the foregoing embodiments, wherein administering comprising injecting locally into tissue of the subject the pharmaceutical composition comprising an effective amount of versikine or a variant thereof.

Embodiment 15

The method of embodiment 14, wherein the tissue is a tumor.

Embodiment 16

The method of any of the foregoing embodiments, wherein administering comprises treating explanted cells of the subject with the pharmaceutical composition comprising an effective amount of versikine or a variant thereof, and administering the treated explanted cells to the subject.

Embodiment 17

The method of embodiment 16, wherein the explanted cells comprise T-cells or dendritic cells.

Embodiment 18

The method of embodiments 16 or 17, further comprising contacting the explanted cells with an antigen prior to administering the treated cells to the subject.

Embodiment 19

The method of any of the foregoing embodiments, further comprising administering an antigen to the subject before, concurrently with, or after administering the pharmaceutical composition comprising versikine or the variant thereof to the subject.

Embodiment 20

The method of embodiment 18 or 19, wherein the antigen is a tumor antigen.

Embodiment 21

The method of any of the foregoing embodiments, wherein the subject has a cell proliferative disease or disorder such as cancer.

Embodiment 22

The method of embodiment 21, wherein the cancer is selected from the group consisting of adenocarcinoma, leukemia, lymphoma, melanoma, myeloma, sarcoma, and teratocarcinoma.

Embodiment 23

The method of embodiment 21, wherein the cancer is selected from cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

Embodiment 24

The method of any of the foregoing embodiments, wherein the subject has a hematological malignancy.

Embodiment 25

The method of any of the foregoing embodiments, wherein the subject has myeloma.

Embodiment 26

The method of any of embodiments 21-25, further comprising administering to the subject cancer therapy before, concurrently with, or after administering the pharmaceutical composition comprising versikine or the variant thereof.

Embodiment 27

The method of embodiment 26, wherein the cancer therapy comprises administering a chemotherapeutic agent.

Embodiment 28

The method of embodiment 27, wherein the chemotherapeutic agent is selected from a group consisting of Abitrexate, Adcetris, Ambochlorin, Aredia (Pamidronate Disodium), Arranon, Asparaginase Erwinia chrysanthemi, Becenum (Carmustine), Beleodaq, Belinostat, Bendamustine Hydrochloride, Bexxar, BiCNU (Carmustine), Blenoxane, Bleomycin, Blinatumomab, Blincyto, Bortezomib, Brentuximab Vedotin, Carfilzomib, Carmubris (Carmustine), Carmustine, Cerubidine, Chlorambucil, Clafen (Cyclophosphamide), Clofarex, Clolar, Cyclophosphamide, Cytarabine, Cytarabine Liposome, Cytosar-U, Cytoxan (Cyclophosphamide), Daratumumab, Darzalex (Daratumumab), Dasatinib, Daunorubicine Hydrochloride, Denileukin Diftitox, DepoCyt, Dexamethasone, Docetaxel, Doxil (Doxorubicin Hydrochloride Liposome), Doxorubicin Hydrochloride Liposome, Dox-SL (Doxorubicin Hydrochloride Liposome), Elotuzumab, Empliciti (Elotuzumab), Epirubicin, Erwinaze, Estramustine, Etoposide, Evacet (Doxorubicin Hydrochloride Liposome), Farydak (Panobinostat), Folex, Folex PFS, Folotyn, Ibrutumomab Tiuxetan, Ibrutinib, Iclusig, Idarubicin, Idelalisib, Imatinib Mesylate, Imbruvica, Intron A, Irinotecan, Istodax, Ixabepilone, Ixazomib Citrate, Kyprolis (Carfilzomib), Lenalidomide, Leukeran, Linfolizin, LipoDox (Doxorubicin Hydrochloride Liposome), Marqibo, Mechlorethamine Hydrochloride, Mercaptopurine, Methotrexate, Methotrexate LPF, Mexate, Mexate-AQ, Mitoxantrone, Mozobil (Plerixafor), Mustargen, Nelarabine, Neosar (Cyclophosphamide), Ninlaro (Ixazomib Citrate), Oncaspar, Ontak, Paclitaxel, Pamidronate Disodium, Panobinostat, Pegaspargase, Plerixafor, Pomalidomide, Pomalyst (Pomalidomide), Ponatinib Hydrochloride, Pralatrexate, Prednisone, Purinethol, Purixan, Recombinant Interferon Alfa-2b, Revlimid (Lenalidomide), Rituxanab, Romidepsin, Rubidomycin, Sprycel, Synovir (Thalidomide), Tarabiune PFS, Teniposide, Thalidomide, Thalomid (Thalidomide), Topotecan, Tositumomab, Treanda, Velban, Velcade (Bortezomib), Vinblastine Sulfate, Vincasar PGS, Vincristine Sulfate, Vincristine Sulfate Liposome, Vinorelbine, Vorinostat, Zevalin, Zoledronic Acid, Zolinza, Zometa (Zoledronic Acid), and Zydelig.

Embodiment 29

The method of embodiment 26, wherein the cancer therapy comprises one or more of therapies in which oncolytic viruses are administered, therapies in which immunomodulatory drugs are administered, therapies in which anthracyclines are administered, and therapies in which check-point blockers are administered.

Embodiment 30

The method of embodiment 26, wherein the cancer therapy comprises one or more of therapies in which chimeric antigen receptor (CAR) T-cells are administered, and therapies in which tumor infiltrating lymphocyte (TIL) are administered.

Embodiment 31

The method of embodiment 26, wherein the cancer therapy comprises radiation therapy.

Embodiment 32

The method of any of the foregoing embodiments, further comprising, before administering the pharmaceutical composition comprising versikine or the variant thereof, determining the concentration of versikine in a biological sample from the subject.

Embodiment 33

The method of embodiment 32, wherein the biological sample is blood or a blood product.

Embodiment 34

The method of embodiment 32, wherein the biological sample is tissue.

Embodiment 35

The method of embodiment 34, wherein the tissue is obtained from a tumor.

Embodiment 36

A kit, which optionally may be used to perform any of the foregoing methods, the kit comprising one or more of: (a) versikine or a variant thereof, wherein the versikine or the variant thereof optionally is provided as a pharmaceutical composition; and (b) a reagent for detecting the concentration of versikine in a biological sample (e.g., an anti-versikine antibody which optionally is labelled with a detectable label).

Embodiment 37

An isolated polypeptide comprising, consisting essentially of, or consisting of the amino acid sequence of any of SEQ ID NOs:3-27 or an amino acid sequence having a least about 80% sequence identity to any of SEQ ID NOs:3-27, wherein the polypeptide comprises a non-naturally occurring N-terminal methionine and the polypeptide induces expression of an interferon type 1 signature.

Embodiment 38

The isolated polypeptide of embodiment 37 comprising, consisting essentially of, or consisting of the amino acid sequence of any of SEQ ID NOs:3, 7, 10, 12, 14, 18, 21, 23, 25 and 27.

Embodiment 39

The isolated polypeptide of embodiment 37 or 38 comprising, consisting essentially of, or consisting of a fragment of any of SEQ ID NOs:1-27.

Embodiment 40

The isolated polypeptide of any of embodiments 37-39, wherein the polypeptide does not comprise the amino acid sequence of SEQ ID NOs:4 or 8-27.

Embodiment 41

The isolated polypeptide of any of embodiments 37-40, wherein the polypeptide does not have any chondroitin sulfate side chains.

Embodiment 42

The isolated polypeptide of any of embodiments 37-41, wherein the polypeptide has one or more amino acid modifications selected from the group consisting of acylation (e.g., N-terminal acylation), acetylation (e.g., N-terminal acetylation), formylation, lipolylation, myristoylation, palmitoylation, alkylation, isoprenylation, prenylation, and amidation (e.g., C-terminal amidation).

Embodiment 43

The isolated polypeptide of any of embodiments 37-42, wherein the polypeptide comprises a fused antigen-binding domain.

Embodiment 44

The isolated polypeptide of embodiment 43, wherein the antigen-binding domain binds to an epitope of a tumor antigen.

Embodiment 45

A pharmaceutical composition comprising an effective amount of any of the polypeptides of embodiments 37-44 for inducing expression of an interferon type 1 signature in a subject in need thereof.

Embodiment 46

An isolated polynucleotide encoding the isolated polypeptide of any of embodiments 37-44.

Embodiment 47

An expression vector comprising the isolated polynucleotide of embodiment 46 operably linked to a promoter.

Embodiment 48

An isolated cell comprising the expression vector of embodiment 47.

Embodiment 49

An anti-tumor vaccine comprising versikine, optionally wherein the vaccine stimulates and/or activates dendritic cells.

Embodiment 50

A method for treating a subject having a cell proliferative disease or disorder such as cancer or at risk for developing a cell proliferative disease or disorder such as cancer, the method comprising administered to the subject a pharmaceutical composition comprising versikine, optionally, wherein the pharmaceutical composition is an anti-tumor vaccine.

Embodiment 51

A method comprising detecting versican proteolysis in a biological sample comprising cancer cells.

Embodiment 52

The method of embodiment 51, wherein detecting versican proteolysis comprises detecting a fragment of versikine.

EXAMPLES

The following Examples are illustrative and are not intended to limit the scope of the claimed subject matter.

Example 1—Immunoregulatory Roles of Versican Proteolysis in the Myeloma Microenvironment Reference is made to the manuscript: Hope et al., "Immunoregulatory Roles of Versican Proteolysis in the Myeloma Microenvironment," Blood. 2016 Aug. 4; 128(5):680, which is incorporated herein by reference in its entirety.

Abstract

Myeloma immunosurveillance remains incompletely understood. We have demonstrated proteolytic processing of the matrix proteoglycan, versican, in myeloma tumors. Whereas intact versican exerts tolerogenic activities through Toll-like receptor (TLR)-2 binding, the immunoregulatory consequences of versican proteolysis remain unknown. Here we show that human myeloma tumors displaying CD8+ aggregates underwent versican proteolysis at a site predicted to generate a glucosaminoglycan-bereft N-terminal fragment, versikine. Myeloma-associated macrophages (MAM), but not tumor cells, produced V1-versican, the precursor to versikine, whereas stromal cell-derived ADAMTS1 was the most robustly expressed versican-degrading protease. Purified versikine induced early expression of inflammatory cytokines IL1β and IL6 by freshly-explanted MAM. We show that versikine signals through pathways both dependent and independent of Tp12 kinase, a key regulator of NF☐B1-mediated MAPK activation in macrophages. Unlike intact versican, versikine-induced IL6 production was partially independent of Tlr2. Versikine stimulated expression of type I-interferon (IFN)-stimulated genes in a model of macrophage-myeloma cell crosstalk without detectable type-I or -III interferon induction. Our data suggest that versikine, generated by ADAMTS proteolysis, constitutes a novel bioactive damage-associated-molecular-pattern (DAMP) that may promote T-cell-inflammation and modulate the tolerogenic consequences of intact versican accumulation. Therapeutic versikine administration may potentiate anti-cancer T-cell-activating immunotherapies.

Introduction

Myeloma is a tumor of plasma cells which are terminally differentiated B lymphocytes that produce antibody (Palumbo and Anderson, 2011). Myeloma plasma cells typically live within the bone marrow microenvironment ("canonical" myeloma niche). However malignant plasma cells can often thrive in extramedullary sites and soft tissues ("non-canonical" niche).

We have hypothesized that infiltrating myeloid cells may exert crucial trophic and immunoregulatory functions in both "canonical" and "non-canonical" niches, in part through their regulation of extracellular matrix composition and remodeling (Asimakopoulos et al., 2013). We and others have previously demonstrated that versican, a chondroitin-sulfate large matrix proteoglycan, accumulates in myeloma lesions and have hypothesized that versican may contribute to the regulation of their inflammatory milieu (Gupta et al., 2015; Hope et al., 2014). Versican has crucial, non-redundant significance in embryonic development (Nandadasa et al., 2014) and emerging roles in cancer inflammation, immunoregulation and metastasis (Gao et al., 2012; Kim et al., 2009; Ricciardelli et al., 2009; Wight et al., 2014). Versican promotes tolerogenic polarization of antigen-presenting cells through TLR2 (Tang et al., 2015). Versican is proteolytically cleaved by ADAMTS-type proteases in a highly-regulated manner (Nandadasa et al., 2014). A cleavage product generated by proteolysis of the $Glu^{441}$-$Ala^{442}$ bond within the versican V1 isoform, has been termed versikine (Nandadasa et al., 2014). Versikine has been shown to be bioactive (proapoptotic) during interdigital web regression in the mouse embryo (McCulloch et al., 2009); however, the roles of versican proteolysis and/or versikine in tumor immunomodulation or progression remain unknown.

Results and Discussion

Myeloma Tumors Displaying CD8+ Aggregates Undergo Versican Proteolysis.

Because versican exerts tolerogenic activities in the tumor microenvironment, we hypothesized that versican proteolysis may promote "T-cell inflammation". We stained myeloma bone marrow biopsy specimens with antibodies against a versican neoepitope ($DPEAAE^{441}$) generated by $Glu^{441}$-$Ala^{442}$ cleavage of V1-versican (corresponding to $Glu^{1428}$ in V0-versican). Consecutive sections were stained for CD68, an immunohistochemical marker for tissue-resident macrophages and CD8, a marker of cytotoxic T cells. We observed four patterns of staining in 19 core biopsies arrayed on a UW myeloma tissue array as well as a commercially-obtained myeloma tissue array (FIG. 1). Myeloma tumors displaying CD8+ aggregates (n=5 out of 19) (Gerard et al., 2013) demonstrated intense/moderate versican proteolysis, as detected by the anti-DPEAAE antibody.

All Four Versican Isoforms are Expressed by CD14+ Monocytic Cells in the Myeloma Microenvironment.

Figure 2:
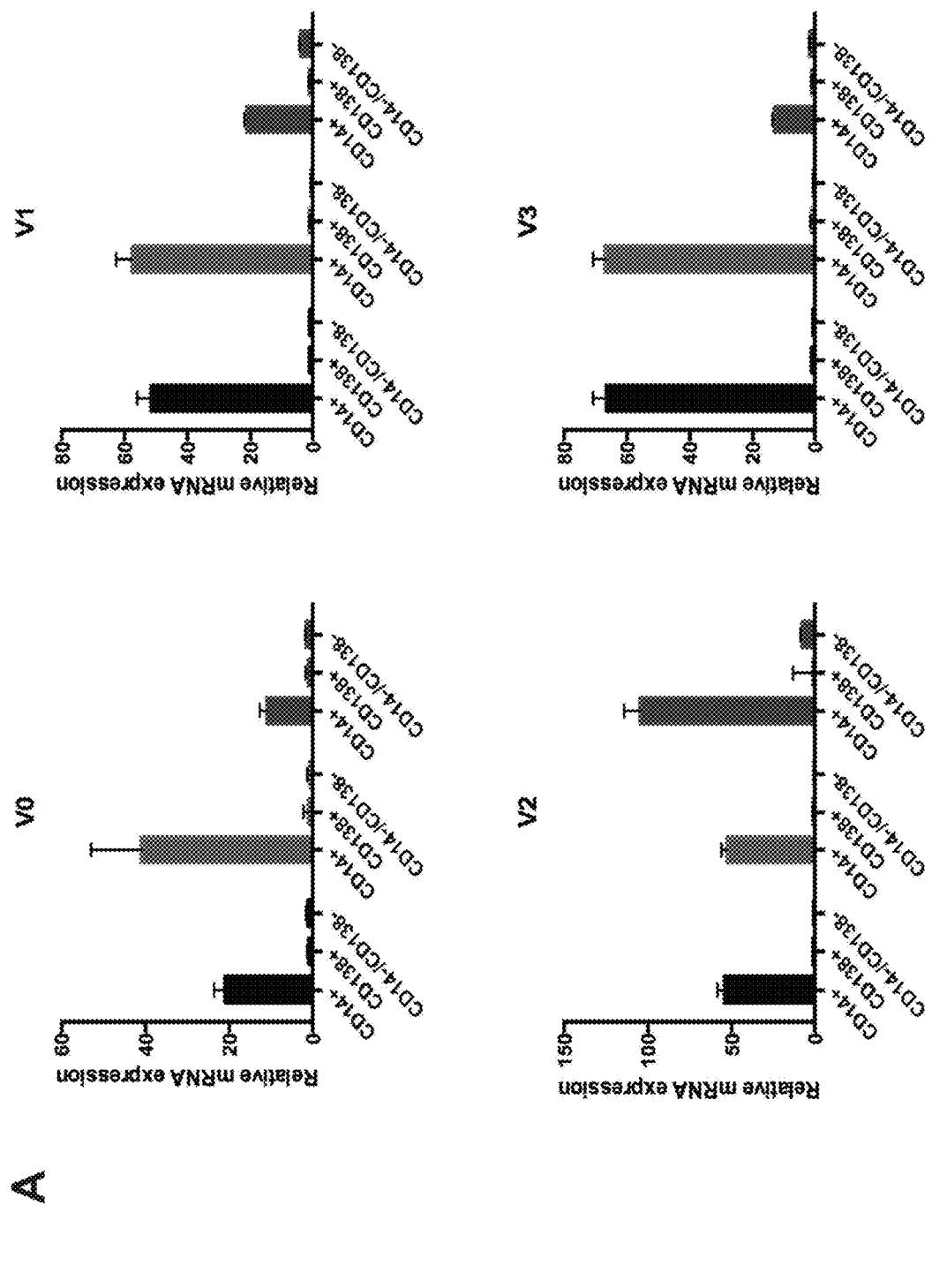
Figure 2:
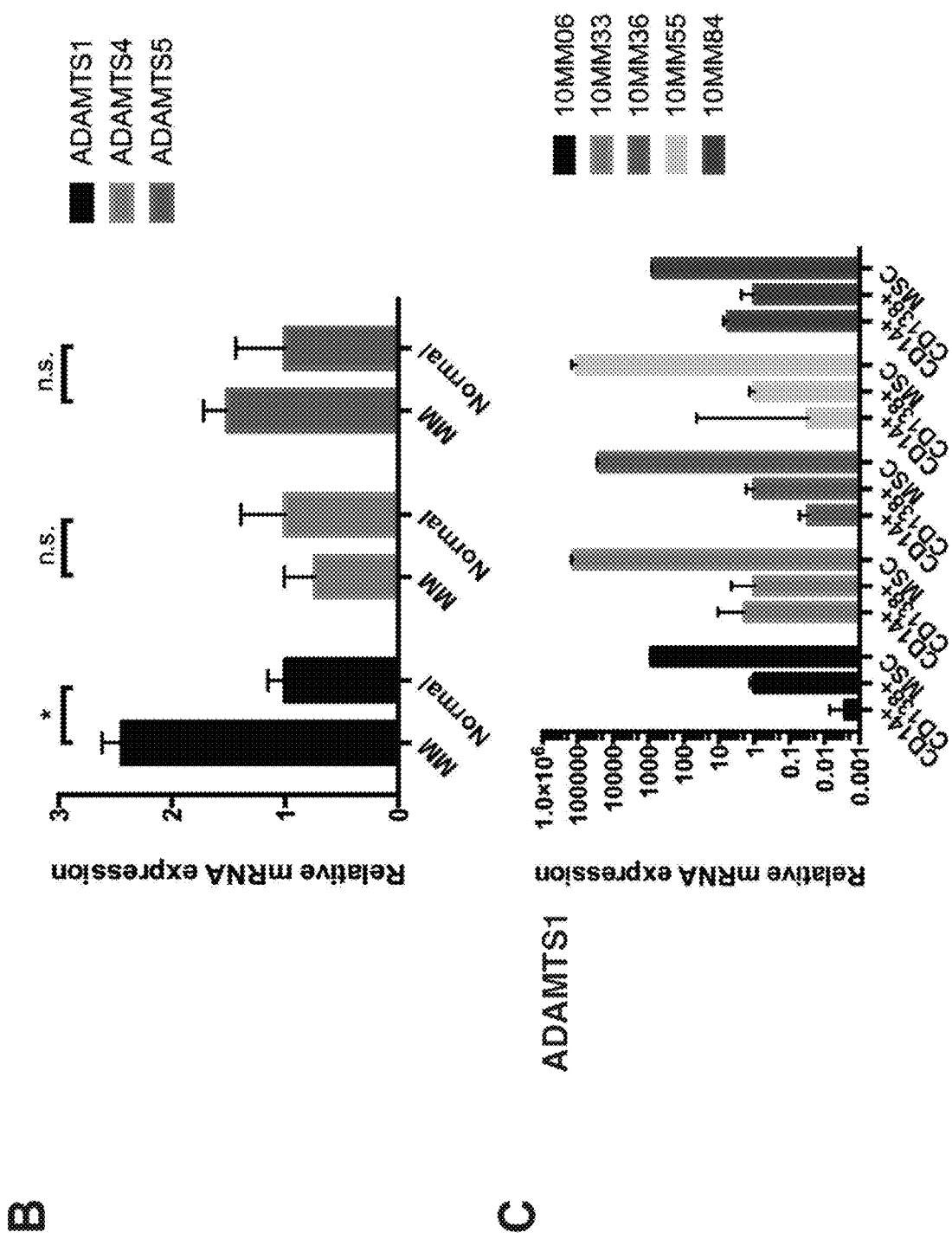

Versican has been variably reported to be expressed by tumor cells or the microenvironment in carcinomas, however its cellular origin in the myeloma niche is unknown. We carried out RT-PCR using versican isoform-specific primers in paired CD138+ malignant plasma cells, CD14+ monocytic cells and bone-marrow stromal cells (BM-MSC) from 3 patients with newly-diagnosed myeloma. We found that CD14+ monocytic cells were the predominant versican producers. Moreover, all four isoforms were expressed by myeloma CD14+ cells (FIG. 2A). This was somewhat surprising, given the reported tissue-specific distribution of certain versican isoforms (e.g., V2 in neural tissue). Importantly, V1-versican, the precursor to versikine, was expressed robustly by myeloma-associated CD14+ monocytic cells. We next determined the relative expression of mRNAs for ADAMTS proteases that may degrade versican in the myeloma microenvironment, i.e., ADAMTS-1, -4, -5, -15, -19 and -20 (Nandadasa et al., 2014). We readily detected ADAMTS1, ADAMTS4 and ADAMTS5 mRNA expression in mononuclear cell lysate from myeloma bone marrow whereas ADAMTS15, ADAMTS19 and ADAMTS20 mRNAs were undetectable (data not shown). A previous report showed low expression of ADAMTS proteases in components of the myeloma microenvironment with the exception of bone marrow-derived mesenchymal stromal cells (BM-MSC) (Bret et al., 2011). Therefore, we compared expression levels for ADAMTS1, ADAMTS4 and ADAMTS5 between myeloma and BM-MSC from normal donors and found that ADAMTS1 was expressed at higher levels by myeloma-derived BM-MSC (FIG. 2B). Within the myeloma microenvironment, BM-MSC expressed much higher levels of ADAMTS1 message than either tumor cells or macrophages (FIG. 2C).

Versikine Stimulates Inflammatory Cytokine Production by Primary MAM but does not have a Direct Impact on Tumor Cell Turnover.

Figure 3:
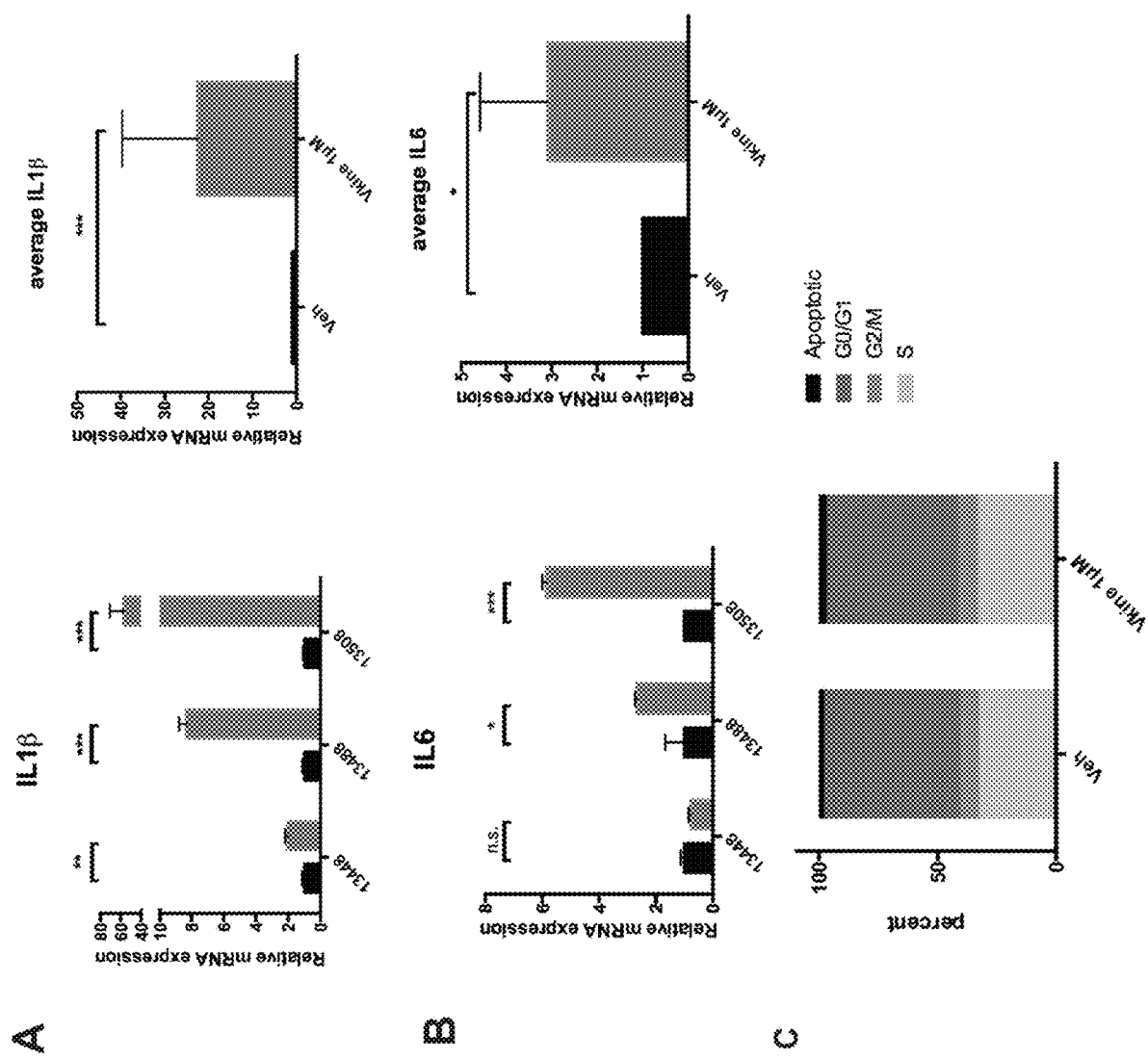

To determine whether versican degradation products possessed immunoregulatory activity, we exposed freshly explanted primary myeloma CD14+ cells to recombinant purified human versikine (1 µM) overnight. Addition of versikine to primary CD14+ cells resulted in induction of inflammatory cytokines IL1β and IL6 (FIG. 3A/B). These data demonstrate that versican chondroitin-sulfate side chains are unnecessary for inflammatory cytokine production, since they are not present on versikine. To determine whether versikine has direct effects on tumor cell turnover in a cell-autonomous fashion, we treated MM1.S human myeloma cells as well as primary bone marrow-derived myeloma cells with recombinant versikine. There was no discernible effect on cell cycle profiles of MM1.S myeloma cells treated with 1 µM versikine (FIG. 3C). Similarly, primary bone marrow-derived, CD138+ myeloma plasma cells did not show detectable changes in cell cycle progression following versikine treatment (not shown). We conclude that versikine does not directly impact on cell cycle progression of human myeloma cells. Our results do not exclude non-cell-autonomous effects on cell cycle progression of myeloma cells through the actions of versikine-induced growth factors, such as IL6.

Versikine Signals Through Tpl2-Dependent and Independent Pathways and May Dispense of Tlr2 for IL6 Production.

Versican stimulates TLR2 complexes to promote immunomodulatory cytokine production (Kim et al., 2009). Signaling downstream of TLRs engages the MAP3K Tpl2 (Cot, MAP3K8), a master regulator of macrophage activation and cytokine production in response to TLR or TNF-like stimuli (Hope et al., 2014; Vougioukalaki et al., 2011). Tpl2 loss in primary bone-marrow-derived macrophages (BMDM) abrogated IL1β production in response to purified versikine (FIG. 4A). However, Tpl2 deletion in macrophages did not significantly affect versikine-induced IL6 (FIG. 4B). Interestingly, versikine did not induce IL10 production (FIG. 4C) and Tpl2 was a negative regulator of IL12p40 production in response to versikine (FIG. 4D), similar to TLR agonists (Jensen et al., 2015).

Our results indicate that versikine may control cytokine production in both a Tp12-dependent and a Tp12-independent manner. To define the signaling cascades induced by versikine, we exposed BMDM to 1 µM purified versikine and collected cell lysate at sequential timepoints post-exposure. Versikine stimulation of wild-type BMDM rapidly induced JNK, p38-MAPK and AKT phosphorylation (FIG. 4E). JNK and AKT phosphorylation were independent of Tpl2 status, whereas Tpl2 loss affected p38-MAPK phosphorylation (FIG. 4E).

Intact versican is thought to signal through TLR2 (Tang et al., 2015). To determine whether versikine-induced IL6 required TLR2, we exposed wild-type and Tlr2−/− BMDM to TLR2 agonist Pam2CSK3 as well as versikine. Whereas Tlr2−/− BMDM showed a complete IL6 production defect in response to Pam2CSK3 (data not shown), they were still able to produce IL6 in response to versikine, albeit at 50% levels compared to WT-BMDM (FIG. 4F). These data demonstrate that versikine signaling pathways may not overlap entirely with those activated by intact versican.

Versikine Modulates Macrophage Polarization.

Addition of versikine to BMDM induced expression of Th1-type cytokine IL12p40 (FIG. 4G). Concurrent Fcγ receptor ligation through addition of ovalbumin (OVA)/anti-OVA immune complexes promoted IL10 production and induced macrophage polarization towards an immunoregulatory M2b phenotype (Th12$^{lo}$-IL10$^{hi}$) (Edwards et al., 2006). Therefore, versikine can act as an endogenous damage-associated molecular pattern (DAMP) that may modulate macrophage polarization in response to extracellular cues.

Versikine Induces Type-I-Interferon-Regulated Genes in a Model of Macrophage-Myeloma Cell Crosstalk.

Figure 5:
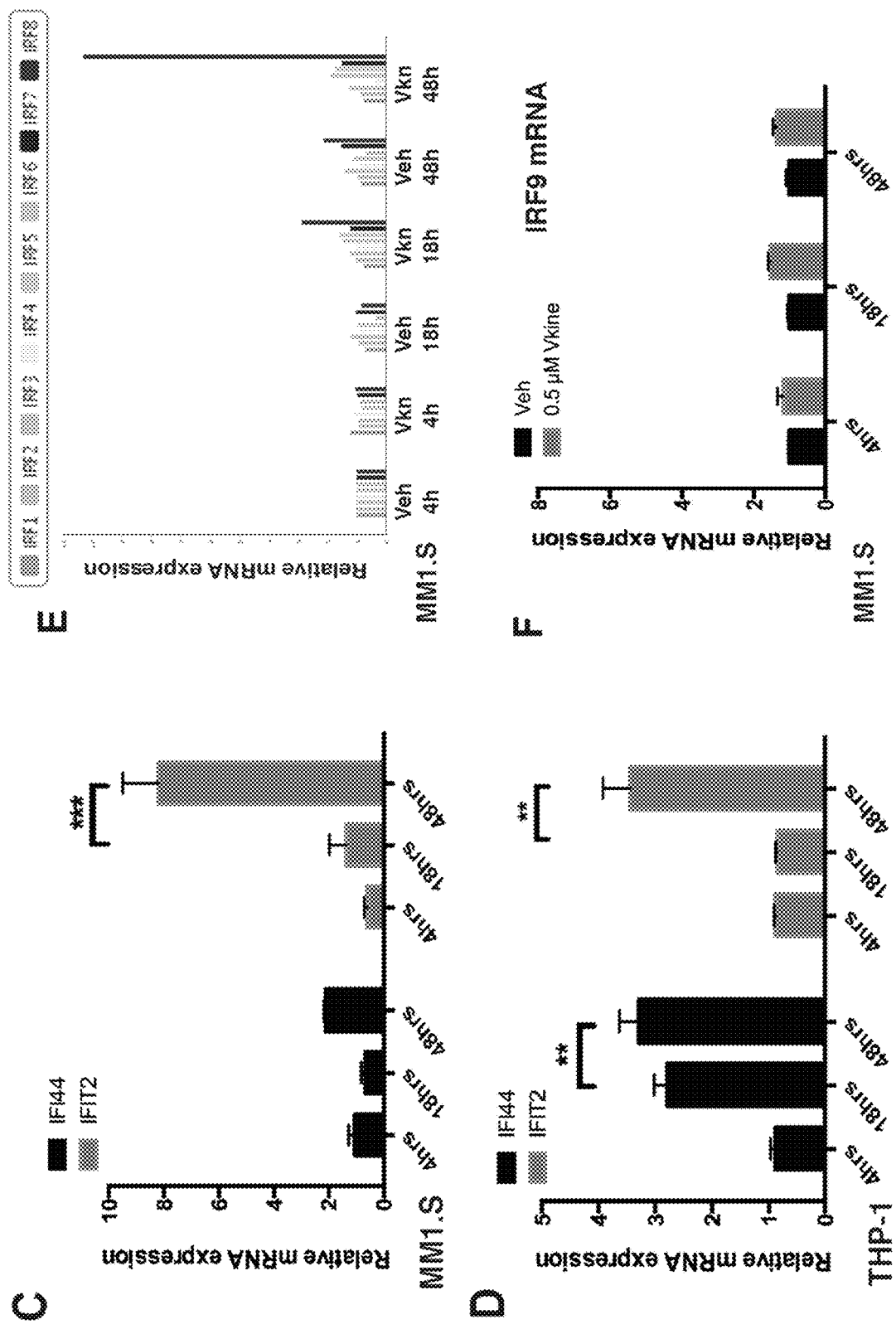
Figure 5:
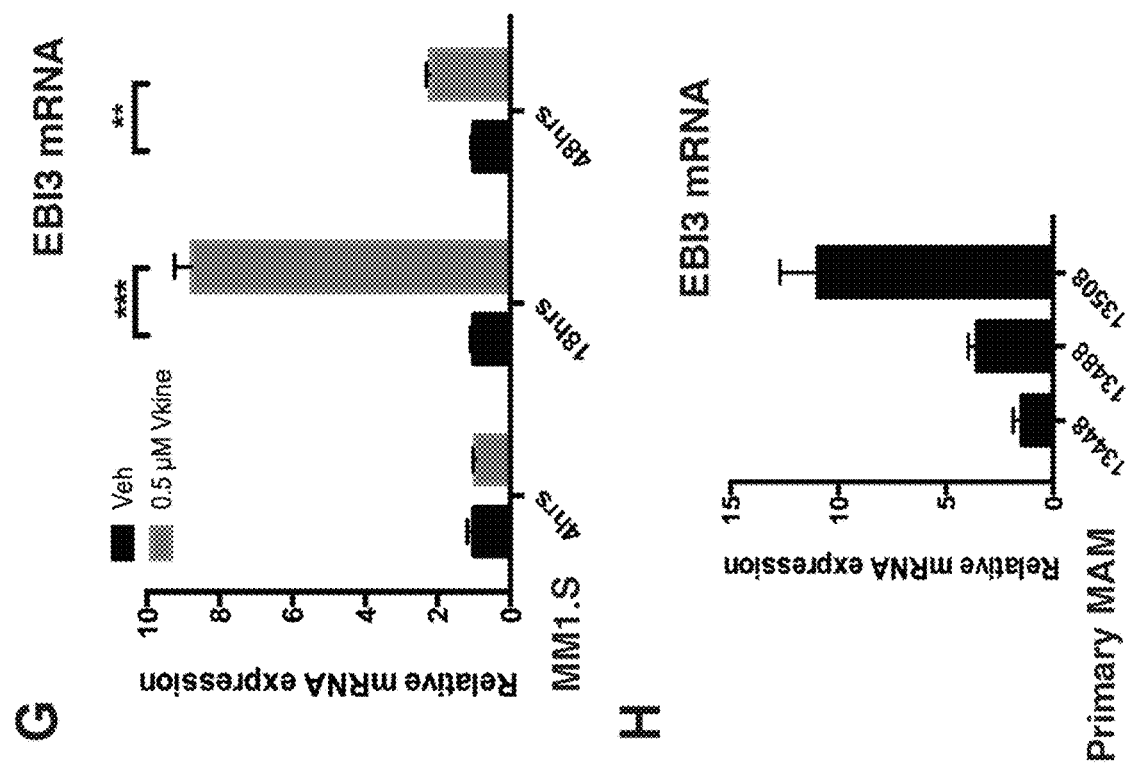

Our data suggested that versican proteolysis results in the generation of versikine, a bioactive fragment that may act as a DAMP in the myeloma microenvironment. We then characterized the effects of versikine expression in a model of myeloma-macrophage crosstalk. Human THP-1 monocytic cells can be induced to generate macrophages that provide a functional platform to study macrophage regulation, including polarization by defined stimuli (Genin et al., 2015). We introduced a versikine-expressing plasmid into THP-1 cells prior to macrophage differentiation. Macrophages transduced with versikine-plasmid or empty-vector control, were co-cultured with human myeloma MM1.S cells for 48 hours. RNA-seq analysis was performed on each cell type after 48 h co-culture. Remarkably, only 23 genes were differentially expressed in MM1.S cells exposed to versikine-secreting macrophages versus control and all 23 genes were overexpressed (FIG. 5A). Of the 23 genes, 13 genes were interferon-stimulated-genes (ISG), suggesting that versikine exposure induced a type I-interferon signature in myeloma cells. Differentially expressed genes did not include those coding for type I- or III-interferons. Interestingly, VCAN transcription was itself induced, suggesting a positive autoregulatory loop responding to cleaved versican. THP-1 macrophages expressing versikine demonstrated differential regulation of 39 genes (4 downregulated, 35 upregulated) when a cutoff of 2-fold expression change was used with a false discovery rate (FDR) threshold of 0.05. 12 upregulated genes defined a type-I-interferon signature (FIG. 5B), again without overt transcription changes in type I or III-interferon genes.

We subsequently treated myeloma-macrophage co-cultures with recombinant versikine. RNA was extracted from each cell type at defined timepoints and subjected to analysis using a parallel RT-PCR array platform focusing on interferon signaling (Human Interferons and Receptors array; see Materials and Methods). As shown in FIG. 5C, 0.5 µM versikine induced upregulation of ISGs in MM1.S myeloma cells as well as THP-1 macrophages (FIG. 5D). IRF8 expression was upregulated at 18 and 48 hours in MM1.S cells (FIG. 5E), whereas IRF9 expression remained relatively constant (FIG. 5F). Interestingly, IRF8 was upregulated in MM1.S cells only in the presence of co-cultured macrophages (data not shown). Irf8 expression in transplanted tumor cells has been shown to be inducible through an 1127-dependent mechanism (Mattei et al., 2012). We observed upregulation of the IL27 subunit, EBI3, in tumor cells and in primary MAM treated with versikine (FIGS. 5G and 5H).

Versican has been proposed to promote immunosuppression and tolerance in tumor microenvironments through a TLR2-dependent mechanism (Tang et al., 2015). We previously reported versican proteolysis in myeloma bone marrow tissue (Hope et al., 2014). We hypothesized that the regulated degradation of versican by ADAMTS-type versicanases may modulate its tolerogenic potential by controlling versican bioavailability, disrupting its extracellular matrix networks and/or by generating novel bioactive fragments. Myeloma marrows with CD8 aggregates showed active versican proteolysis. Interestingly, only 5 out of 19 myeloma marrows showed evidence of CD8 infiltration/aggregates. This low preponderance of CD8-infiltrated myeloma tumors is consistent with the reported failure of checkpoint inhibition as monotherapy in myeloma (Suen et al., 2015). Macrophages, on the other hand, were abundant in all biopsies.

We report that versikine, a product of versican proteolysis, possesses immunoregulatory activities that may promote "T-cell-inflammation" (Gajewski, 2015; Zitvogel et al., 2015). The induction of IRF8 transcription in response to versikine is particularly intriguing and could provide a mechanistic link to ISG upregulation. IRF8 is a transcription factor with central non-redundant roles in dendritic cell development and maturation as well as homeostasis of myeloid-derived suppressor cells (Merad et al., 2013; Waight et al., 2013). IRF8 and IL27 can operate in a regulatory loop (Mattei et al., 2012). IL27 subunit EBI3 was induced by versikine. Ebi3−/− animals are prone to impaired anti-tumor T cell responses and accelerated tumor growth (Liu et al., 2015). Taken together, our results suggest that versikine may antagonize the tolerogenic actions of intact versican and thus, may provide a novel anti-tumor strategy. The findings also suggest that, in addition to small leucine-rich proteoglycans, previously shown to act as DAMPs (Schaefer, 2014), fragments of large aggregating proteoglycans may have the capacity to stimulate innate immunity and provide a bridge to adaptive immunity.

Materials and Methods

Patient Sample Collection and Processing.

Bone marrow aspirates were collected with informed consent under a University of Wisconsin IRB-approved protocol (HO07403). Mononuclear cells were separated using Ficoll-Hypaque 1.073 (GE Healthcare Bio-sciences, Piscataway, N.J., USA) and were immune-magnetically sorted using anti-CD138 or anti-CD14 microbeads (Miltenyi Biotec, Auburn, Calif., USA). Purity was over 90% for both CD14+ and CD138+ fractions. For mesenchymal stromal cells, the CD138−/CD14− double-negative fraction was plated in aMEM supplemented with 10% FBS (Hyclone, Logan, Utah, USA). Attached cells were harvested and passaged using TrypLE (Invitrogen, Carlsbad, Calif., USA) until reaching passage 4.

Versikine Production, Purification and Analysis.

Methods for expression and purification of recombinant versikine from mammalian cells have been previously published (Foulcer et al., 2015; Foulcer et al., 2014, the contents of which are incorporated herein by referenece in their entireties). In brief, a plasmid vector for expression of human versikine (residues 1-441 of the V1 isoform) with a C-terminal myc-His6 tag was transfected into CHO-K1 cells. Serum-free medium was collected from stably transfected cells and combined with Ni-NTA agarose. Bound versikine was sequentially washed with 4 M Guanidine-HCl and 500 mM NaCl and eluted with 250 mM imidazole. Purified versikine was extensively dialysed into phosphate buffered saline. Purified versican was characterized by Coomassie Brilliant Blue staining and LC-MS/MS at the Lerner Research Institute Proteomics Core to identify associated bioactive proteins and by fluorophore-assisted carbohydrate electrophoresis (FACE) for co-purifying hyaluronan (at the Lerner Research Institute Program of Excellences in Glycobiology Glycomics Core). Presence of hyaluronan was ruled out by FACE and by solid phase binding assay and size exclusion chromatography.

Each versikine aliquot used in this study tested negative for endotoxin contamination using ToxinSensor Gel Clot kit (Genscript, sensitivity limit 0.25 endotoxin units (EU)/mL) (roughly equivalent to 25-50 pg/mL). The ultra-sensitive Chromogenic LAL Endotoxin Assay Kit (Genscript) was used to obtain a quantitative determination of the endotoxin concentration in versikine stock: it was determined to be 0.1 EU/mL (roughly equivalent to 10-20 pg endotoxin/mL prior to 1/10 dilution in versikine-treated wells). To definitively exclude the possibility of spurious endotoxin-mediated transcriptional changes, we exposed THP-1 macrophages to graded endotoxin concentrations, 10 ng/mL, 1 ng/mL and each of 500/250/100/75/50/25/10/5/1 pg/mL for 12 hours. RNA was isolated and EBI3 transcripts by RT-PCR were compared to a zero-endotoxin control. EBI3 transcriptional induction was not observed at endotoxin concentrations equal or less than 100 pg/mL.

Mice and Primary Cell Culture.

C57BL6/J, Tpl2−/− (Dumitru et al., 2000), Tlr2−/− (Jax stock #004650) mice were housed, cared for, and used in accordance with the *Guide for Care and Use of Laboratory Animals* (NIH Publication 86-23) under an IACUC-approved protocol (M2395). Bone marrow was extracted from spine and long bones as previously described. BMDM were derived and cultured as previously described (Hope et al., 2014).

Cell and Tissue Culture.

MM1.S cells were generously provided by Dr. Constantine Mitsiades (Dana-Farber Cancer Institute, Boston, Mass.). THP-1 (ATCC® TIB-202™) cells were maintained in tissue culture according to ATCC protocols. Cell culture was carried out in complete RPMI 1640 media supplemented with 10% fetal bovine serum (HyClone), a standard antibiotic/antimycotic solution (Life Technologies, 35050-061), and GlutaMax (Mediatech, 30-004-CI). In co-cultures shown in FIG. 5, the ratio of THP-1 macrophages: MM1.S cells were 5:1 for RNA-seq experiments and 1:1 for recombinant versikine experiments.

RNA Extraction and Real-Time RT-PCR.

RT-PCR was performed using Applied Biosystems® StepOnePlus™ with accompanying software and Power SYBR® Green (Applied Biosystems® No. 4309155). Primer sequences are listed in Supplementary Methods. Human Interferon and Receptor $RT^2$-Profiler PCR array was obtained from Qiagen (PAHS-064Z). Relative expression was determined by ΔΔCt calculation. All RT-PCR protocols were performed in accordance with MIQE standards.

Immunohistochemistry.

The University of Wisconsin myeloma tissue microarray (TMA) has been previously reported (Hope et al., 2014). A second myeloma TMA was purchased from US Biomax (catalog no. T291b). Slides were deparaffinized using standard xylene/ethanol methods followed by antigen retrieval in citrate (DPEAAE and CD68 detection) or EDTA buffer (CD8 detection). Primary antibodies are listed in the Supplementary File.

Immunoblot Analysis.

Whole cell lysates were prepared by boiling cells in Laemmli Sample buffer (Bio-Rad) supplemented with 100 mM DTT for 10 minutes at a final concentration of $10^7$ cells/ml. Protein was quantified using Bradford assay reagent (BioRad). $10^5$ cells or 20 µg protein was resolved by SDS-PAGE and transferred to Immobilon-P PVDF membrane (Millipore). Primary antibodies are listed in the Supplementary File.

Cell Cycle Analysis.

Cells were harvested after exposure to BrdU for 30 minutes. Cells were washed in PBS, fixed and permeabilized in 70% ethanol and stained with anti-BrdU-FITC and propidium iodide per standard protocols. Flow cytometry was carried out on FACSCalibur analyzer (Becton Dickinson). FlowJo software was used for flow data analysis.

Cytokine Measurement.

Cytokine levels were measured in culture supernatant using the bead-based Bio-Plex system (Bio-Rad).

RNA-Seq and Data Analysis.

Total RNA submitted to the University of Wisconsin-Madison Biotechnology Center was verified for purity and integrity via the NanoDrop2000 Spectrophotometer and Agilent 2100 BioAnalyzer, respectively. Samples that met the Illumina sample input guidelines were prepared according to the TruSeq® Stranded Total RNA Sample Preparation Guide (Rev. E) using the Illumina® TruSeq® Stranded Total RNA Sample Preparation kits (Illumina Inc., San Diego, Calif., USA) with minor modifications. For each library preparation, lug of total RNA was ribosomally reduced as directed. Ribosomally depleted. RNA samples were purified by paramagnetic beads (AgencourtRNA Clean XP beads, Beckman Coulter, Indianapolis Ind., USA). Subsequently, each rRNA-depleted sample was fragmented using divalent cations under elevated temperature. The fragmented RNA was synthesized into double-stranded cDNA using SuperScript IIReverse Transcriptase (Invitrogen, Carlsbad, Calif., USA) and random primers for first strand cDNA synthesis followed by second strand synthesis using DNA Polymerase land RNAse H for removal of mRNA. Double-stranded cDNA was purified by paramagnetic beads (Agencourt AMPure XP beads, Beckman Coulter). The cDNA products were incubated with Klenow DNA Polymerase to add an 'A' base (Adenine) to the 3' end of the blunt DNA fragments. DNA fragments were ligated to Illumina adapters, which have a single 'T' base (Thymine) overhang at their 3'end. The adapter-ligated DNA products were purified by paramagnetic beads. Adapter ligated DNA was amplified in a Linker Mediated PCR reaction (LM-PCR) for 10 cycles using Phusion™ DNA Polymerase and Illumina's PE genomic DNA primer set and then purified by paramagnetic beads. Quality and quantity of the finished libraries were assessed using an Agilent DNA1000 chip (Agilent Technologies, Inc., Santa Clara, Calif., USA) and Qubit® dsDNA HS Assay Kit (Invitrogen, Carlsbad, Calif., USA), respectively. Libraries were standardized to 2 µM. Cluster generation was performed using standard Cluster Kits (v3) and the Illumina Cluster Station. Single 100 bp sequencing was performed, using standard SBS chemistry (v3) on an Illumina HiSeq2000 sequencer. Images were analyzed using the standard Illumina Pipeline, version 1.8.2. The RNA-seq reads were trimmed and filtered to remove contaminant and low quality bases prior to the analysis. Filtered reads were aligned to the reference genome using open source software STAR followed by RSEM (Li et al., 2010) for reads assignment and expression estimation. We used EdgeR (Robinson et al., 2010) to compare differential expression (DE) between conditions/treatment. The DE gene list can be obtained by filtering result by FDR value and relative fold changes.

REFERENCES

Asimakopoulos, F., J. Kim, R. A. Denu, C. Hope, J. L. Jensen, S. J. Ollar, E. Hebron, C. Flanagan, N. Callander, and P. Hematti. 2013. Macrophages in multiple myeloma: emerging concepts and therapeutic implications. Leuk Lymphoma 54:2112-2121.

Bret, C., D. Hose, T. Reme, A. Kassambara, A. Seckinger, T. Meissner, J. F. Schved, T. Kanouni, H. Goldschmidt, and B. Klein. 2011. Gene expression profile of ADAMs and ADAMTSs metalloproteinases in normal and malignant plasma cells and in the bone marrow environment. Exp Hematol 39:546-557 e548.

Coster et al., 1979. Isolation of 35S- and 3H-labelled proteoglycans from cultures of human embryonic skin fibroblasts. Biochem. J. 183, 669-681.

Dobin, A., C. A. Davis, F. Schlesinger, J. Drenkow, C. Zaleski, S. Jha, P. Batut, M. Chaisson, and T. R. Gingeras. 2013. STAR: ultrafast universal RNA-seq aligner. Bioinformatics 29:15-21.

Dours-Zimmermann, et al., 1994. A novel glycosaminoglycan attachment domain identified in two alternative splice variants of human versican. J. Biol. Chem. 269, 32992-32998.

Dumitru, C. D., J. D. Ceci, C. Tsatsanis, D. Kontoyiannis, K. Stamatakis, J. H. Lin, C. Patriotis, N. A. Jenkins, N. G. Copeland, G. Kollias, and P. N. Tsichlis. 2000. TNF-alpha induction by LPS is regulated post-transcriptionally via a Tp12/ERK-dependent pathway. Cell 103:1071-1083.

Edwards, J. P., X. Zhang, K. A. Frauwirth, and D. M. Mosser. 2006. Biochemical and functional characterization of three activated macrophage populations. J Leukoc Biol 80:1298-1307.

Foulcer, S. J., A. J. Day, and S. S. Apte. 2015. Isolation and purification of versican and analysis of versican proteolysis. Methods Mol Biol 1229:587-604.

Foulcer, S. J., C. M. Nelson, M. V. Quintero, B. Kuberan, J. Larkin, M. T. Dours-Zimmermann, D. R. Zimmermann, and S. S. Apte. 2014. Determinants of versican-V1 proteoglycan processing by the metalloproteinase ADAMTS5. J Biol Chem 289:27859-27873.

Gajewski, T. F. 2015. The Next Hurdle in Cancer Immunotherapy: Overcoming the Non-T-Cell-Inflamed Tumor Microenvironment. Semin Oncol 42:663-671.

Gao, D., N. Joshi, H. Choi, S. Ryu, M. Hahn, R. Catena, H. Sadik, P. Argani, P. Wagner, L. T. Vandat, J. L. Port, B. Stiles, S. Sukumar, N. K. Altorki, S. Rafii, and V. Mittal. 2012. Myeloid progenitor cells in the premetastatic lung promote metastases by inducing mesenchymal to epithelial transition. Cancer Res 72:1384-1394.

Genin, M., F. Clement, A. Fattaccioli, M. Raes, and C. Michiels. 2015. M1 and M2 macrophages derived from THP-1 cells differentially modulate the response of cancer cells to etoposide. BMC Cancer 15:577.

Gerard, A., O. Khan, P. Beemiller, E. Oswald, J. Hu, M. Matloubian, and M. F. Krummel. 2013. Secondary T cell-T cell synaptic interactions drive the differentiation of protective CD8+ T cells. Nat Immunol 14:356-363.

Gupta, N., R. Khan, R. Kumar, L. Kumar, and A. Sharma. 2015. Versican and its associated molecules: potential diagnostic markers for multiple myeloma. Clin Chim Acta 442:119-124.

Hope, C., S. J. Ollar, E. Heninger, E. Hebron, J. L. Jensen, J. Kim, I. Maroulakou, S. Miyamoto, C. Leith, D. T. Yang, N. Callander, P. Hematti, M. Chesi, P. L. Bergsagel, and F. Asimakopoulos. 2014. TPL2 kinase regulates the inflammatory milieu of the myeloma niche. Blood 123:3305-3315.

Jensen, J. L., A. Rakhmilevich, E. Heninger, A. T. Broman, C. Hope, F. Phan, S. Miyamoto, I. Maroulakou, N. Callander, P. Hematti, M. Chesi, P. L. Bergsagel, P.

Sondel, and F. Asimakopoulos. 2015. Tumoricidal Effects of Macrophage-Activating Immunotherapy in a Murine Model of Relapsed/Refractory Multiple Myeloma. Cancer Immunol Res 3:881-890.

Kischel, et al. 2010. Versican overexpression in human breast cancer lesions: known and new isoforms for stromal tumor targeting. Int. J. Cancer 126, 640-650.

Kim, S., H. Takahashi, W. W. Lin, P. Descargues, S. Grivennikov, Y. Kim, J. L. Luo, and M. Karin. 2009. Carcinoma-produced factors activate myeloid cells through TLR2 to stimulate metastasis. Nature 457:102-106.

Li, B., V. Ruotti, R. M. Stewart, J. A. Thomson, and C. N. Dewey. 2010. RNA-Seq gene expression estimation with read mapping uncertainty. Bioinformatics 26:493-500.

Liu, Z., J. Q. Liu, Y. Shi, X. Zhu, Z. Liu, M. S. Li, J. Yu, L. C. Wu, Y. He, G. Zhang, and X. F. Bai. 2015. Epstein-Barr virus-induced gene 3-deficiency leads to impaired antitumor T-cell responses and accelerated tumor growth. Oncoimmunology 4:e989137.

Mattei, F., G. Schiavoni, P. Sestili, F. Spadaro, A. Fragale, A. Sistigu, V. Lucarini, M. Spada, M. Sanchez, A. Scala, A. Battistini, F. Belardelli, and L. Gabriele. 2012. IRF-8 controls melanoma progression by regulating the cross talk between cancer and immune cells within the tumor microenvironment. Neoplasia 14:1223-1235.

McCulloch, D. R., C. M. Nelson, L. J. Dixon, D. L. Silver, J. D. Wylie, V. Lindner, T. Sasaki, M. A. Cooley, W. S. Argraves, and S. S. Apte. 2009. ADAMTS metalloproteases generate active versican fragments that regulate interdigital web regression. Dev Cell 17:687-698.

Merad, M., P. Sathe, J. Helft, J. Miller, and A. Mortha. 2013. The dendritic cell lineage: ontogeny and function of dendritic cells and their subsets in the steady state and the inflamed setting. Annu Rev Immunol 31:563-604.

Mosser, D. M., and J. P. Edwards. 2008. Exploring the full spectrum of macrophage activation. Nat Rev Immunol 8:958-969.

Nandadasa, S., S. Foulcer, and S. S. Apte. 2014. The multiple, complex roles of versican and its proteolytic turnover by ADAMTS proteases during embryogenesis. Matrix Biol 35:34-41.

Palumbo, A., and K. Anderson. 2011. Multiple myeloma. N Engl J Med 364:1046-1060.

Ricciardelli, C., A. J. Sakko, M. P. Ween, D. L. Russell, and D. J. Horsfall. 2009. The biological role and regulation of versican levels in cancer. Cancer Metastasis Rev 28:233-245.

Robinson, M. D., D. J. McCarthy, and G. K. Smyth. 2010. edgeR: a Bioconductor package for differential expression analysis of digital gene expression data. Bioinformatics 26:139-140.

Schaefer, L. 2014. Complexity of danger: the diverse nature of damage-associated molecular patterns. J Biol Chem 289:35237-35245.

Suen, H., R. Brown, S. Yang, P. J. Ho, J. Gibson, and D. Joshua. 2015. The failure of immune checkpoint blockade in multiple myeloma with PD-1 inhibitors in a phase 1 study. Leukemia 29:1621-1622.

Sugimoto, K., M. Ohata, J. Miyoshi, H. Ishizaki, N. Tsuboi, A. Masuda, Y. Yoshikai, M. Takamoto, K. Sugane, S. Matsuo, Y. Shimada, and T. Matsuguchi. 2004. A serine/threonine kinase, Cot/Tp12, modulates bacterial DNA-induced IL-12 production and Th cell differentiation. J Clin Invest 114:857-866.

Tang, M., J. Diao, H. Gu, I. Khatri, J. Zhao, and M. S. Cattral. 2015. Toll-like Receptor 2 Activation Promotes Tumor Dendritic Cell Dysfunction by Regulating IL-6 and IL-10 Receptor Signaling. Cell Rep 13:2851-2864.

Vougioukalaki, M., D. C. Kanellis, K. Gkouskou, and A. G. Eliopoulos. 2011. Tpl2 kinase signal transduction in inflammation and cancer. Cancer Lett 304:80-89.

Waight, J. D., C. Netherby, M. L. Hensen, A. Miller, Q. Hu, S. Liu, P. N. Bogner, M. R. Farren, K. P. Lee, K. Liu, and S. I. Abrams. 2013. Myeloid-derived suppressor cell development is regulated by a STAT/IRF-8 axis. J Clin Invest 123:4464-4478.

Wight, T. N., I. Kang, and M. J. Merrilees. 2014. Versican and the control of inflammation. Matrix Biol 35:152-161.

Xu, H., V. K. Chaudhri, Z. Wu, K. Biliouris, K. Dienger-Stambaugh, Y. Rochman, and H. Singh. 2015. Regulation of bifurcating B cell trajectories by mutual antagonism between transcription factors IRF4 and IRF8. Nat Immunol 16:1274-1281.

Zhang, J., X. Qian, H. Ning, J. Yang, H. Xiong, and J. Liu. 2010. Activation of IL-27 p28 gene transcription by interferon regulatory factor 8 in cooperation with interferon regulatory factor 1. J Biol Chem 285:21269-21281.

Zitvogel, L., L. Galluzzi, O. Kepp, M. J. Smyth, and G. Kroemer. 2015. Type I interferons in anticancer immunity. Nat Rev Immunol 15:405-414.

Zimmermann et al., 1989. Multiple domains of the large fibroblast proteoglycan, versican. EMBO J. 8, 2975-2981.

Example 2—Versican Proteolysis Predicts Robust CD8+ T-Cell Infiltration in Human Mismatch Repair-Proficient and -Deficient Colorectal Cancers: Mechanistic Implications Abstract Colorectal cancer (CRC) originates within immunologically complex microenvironments. To date the benefits of immunotherapy have been modest except in neoantigen-laden mismatch repair (MMR)-deficient tumors. Approaches to enhance tumor-infiltrating lymphocytes in the tumor bed may substantially augment clinical immunotherapy responses. We recently reported that proteolysis of the tolerogenic matrix proteoglycan versican (VCAN), in myeloma tumors, generates a bioactive fragment, versikine, with putative immunostimulatory activities. Here we report that VCAN proteolysis strongly correlated with CD8+ T-cell infiltration in CRC. Tumors displaying active VCAN proteolysis and low total VCAN were associated with robust (10-fold) CD8+ T-cell infiltration. The correlation between VCAN proteolysis and CD8+ T-cell infiltration was maintained in MMR-proficient and -deficient CRCs. Tumor-intrinsic WNT pathway activation was associated with CD8+ T-cell exclusion and correlated with VCAN accumulation. VCAN proteolytic fragment, versikine, promoted the generation of CD103+CD11c$^{hi}$MHCII$^{hi}$ conventional dendritic cells (cDC) from flt3L-mobilized primary bone marrow-derived cultures, suggesting that versican proteolysis in the tumor microenvironment may favor differentiation of tumor-seeding DC precursors towards IRF8-expressing CD103+DC, endowed with enhanced tumor antigen presentation capacity. Our findings indicate that VCAN proteolysis may shape CRC immune contexture and provide a rationale for testing VCAN proteolysis as a predictive and/or prognostic immune biomarker.

Significance

This study identifies VCAN proteolysis as a potential key regulator of CD8+ T-cell infiltration in colorectal cancer. Further studies are warranted to determine the role of VCAN proteolysis as an immune biomarker. In addition, therapeutic manipulation of the VCAN-versikine axis may augment immunotherapy efficacy against CRC.

Introduction

CRC is the second leading cause of cancer-related mortality in the United States (1). The 5-year survival rate for patients with metastatic disease is unacceptably low (12%), generating an impetus for rapid progress to improve outcomes. Recent advances in cancer immunotherapy have only marginally impacted outcomes in CRC (2, 3). The noteworthy exception includes patients with mismatch repair-deficient (dMMR) tumors where genetic instability generates an expanded neo-antigenic repertoire (4). In dMMR cancers, treatment with the anti-PD1 antibodies pembrolizumab and nivolumab result in deep and prolonged therapeutic responses for a large proportion of patients (2, 4, 5). Unfortunately, not all patients with dMMR CRCs respond to these agents indicating that other regulatory factors play a key role in the response of CRCs to checkpoint blockade. In addition, an effective means to utilize immuno-oncology agents for mismatch repair proficient (pMMR) CRCs, which encompass greater than 95% of all metastatic CRCs, has yet to be identified.

The presence of infiltrating lymphocytes (TILs) is linked to favorable clinical outcomes and increased response rates to immune checkpoint inhibition (5, 6). Thus, TIL infiltration possesses both prognostic and predictive biomarker utility. However, at a mechanistic level, the tumor-cell autonomous and non-autonomous networks controlling immune infiltration into the tumor bed are mostly unknown. Approaches to enhance TIL entry/activation could have a major impact on immunotherapy efficacy.

We recently demonstrated that versican (VCAN), a large matrix proteoglycan with immunoregulatory activity, accumulates in the extracellular matrix of multiple myeloma tumors (7). VCAN contributes to cancerous and non-cancerous inflammation by promoting leukocyte-derived elaboration of inflammatory mediators (8-13) but also immunodeficiency through dendritic cell (DC) dysfunction (14). Interestingly, we also detected in situ VCAN proteolysis in a pattern consistent with the activities of a disintegrin and metalloproteinase with thrombospondin motifs (ADAMTS)-type proteases (15). Whereas tumor-associated macrophages produce all known VCAN isoforms, tumor-associated mesenchymal stromal cells secrete ADAMTS proteases that cleave VCAN. We hypothesized that VCAN proteolysis serves to generate bioactive fragments. Indeed, we demonstrated a fragment containing VCAN's N-terminal 441 amino acids, "versikine" (16), elicits a transcriptional program that is predicted to promote immunogenicity, and thus, antagonize the tolerogenic actions of its parent, intact VCAN (15). However, it is unclear whether VCAN-dependent immunoregulatory mechanisms are operative in non-myeloma, or indeed non-hematopoietic, settings. We chose to investigate CRC because both myeloma and CRC are driven by chronic inflammatory networks (17) and because better understanding of CRC immunosurveillance mechanisms will likely result in improved outcomes for large patient populations. Here we demonstrate that VCAN proteolysis correlates with CD8+ T-cell infiltration in CRC, regardless of mismatch-repair status and provide mechanistic implications. These results provide strong rationale for investigation of VCAN processing in immunotherapy prognostication and therapy across several solid and liquid tumor types.

Materials and Methods

Colorectal Cancer (CRC) Tissue Microarray (TMA).

A CRC TMA was created through the University of Wisconsin Carbone Cancer Center Translational Science Biocore Biobank. This TMA contains samples from 122 subjects with colorectal cancer across all stages. For each subject, the TMA contains 2 cores from the primary tumor and 1 core of tumor-associated normal tissue. The tumors utilized in the TMA were selected for their location and stage, such that an equal distribution of right, left and rectal tumors and stage I through IV cancers are present.

Immunohistochemical (IHC) Methods and Antibodies.

Unstained 4-5 µm-thick TMA sections were deparaffinized and rehydrated using standard methods. Antigen retrieval was carried out in EDTA buffer (CD8 detection) or citrate (all others). The slides were treated with chondroitinase ABC prior to staining with the total VCAN antibody (18). Primary antibodies included total VCAN (HPA004726, Sigma, St. Louis, Mo.), αDPEAAE (PA1-1748A, Thermo Fisher, Waltham, Mass.), CD8 (c4-0085-80, Ebioscience, San Diego, Calif., USA), phosphorylated ERK 1/2 (Thr202/Tyr204, 4370, Cell Signaling Technology, Danvers, Mass.), phosphorylated ribosomal protein S6 (RPS6) (Ser235/236, 4858, Cell Signaling Technology), and CTNNB1 (β-catenin, 8480, Cell Signaling Technology). The αDPEAAE neoepitope antibody has been previously validated (18).

Scoring and Analysis of Staining Patterns.

Cytoplasmic and membrane staining of the epithelium and stroma was scored for each core sample by a pathologist (K.A.M.) blinded to clinical parameters. Stained slides were examined using an Olympus BX43 microscope with attached Olympus DP73 digital camera (Olympus Corp, Waltham, Mass.). Epithelium and stroma were evaluated separately for total VCAN and αDPEAAE staining. Immunostaining for VCAN, αDPEAAE, phosphorylated ERK1/2, and phosphorylated RPS6 was assessed by scoring staining intensity (0 for no staining, 1 for low/weak staining, 2 for moderate staining and 3 for strong/intense staining) and the percentage of cells staining positive (0 for no staining, 1 for >0-10%, 2 for 11-50%, 3 for 51-75% and 4 for >75% staining; FIG. 10). For CD8+ detection, the number of tumor infiltrating lymphocytes (TILs) per high-power field (HPF) within the malignant epithelium was calculated using a single area at 400× magnification (ocular 10× with an objective of 40×). Nuclear localization of β-catenin was recorded as present or absent. Tissue cores that were missing, damaged, contained staining artifacts, or had uncertain histology were excluded from the analysis.

Mismatch Repair (MMR) Analyses.

MMR status was determined by IHC for MLH1, MSH6, MSH2, and PMS2. The following prediluted primary antibodies were utilized: MLH1 ((M1) mouse monoclonal, Ventana Medical Systems, Inc, Tucson, Ariz.), MSH6 ((44) mouse monoclonal, Ventana Medical Systems, Inc), MSH2 ((G219-1129) mouse monoclonal, Ventana Medical Systems, Inc), and PMS2 ((EPR3947) rabbit monoclonal, Ventana Medical Systems, Inc). Staining was performed on a BenchMark ULTRA automated slide staining system and detected using the Opitview DAB IHC detection kit. Absence of staining for these proteins was scored by independent pathology review (K.A.M.). Tumor infiltrating leukocytes were utilized as an internal control.

KI67 Proliferation Index.

Immunofluorescence was performed by placing the TMA slides into a humidity chamber after slides were deparaffinized and rehydrated. Slides were blocked with 5% bovine serum albumin in Tris Buffered Saline (TBS) with 0.05%

Tween 20 for one hour at room temperature. Slides were then washed in TBS. The KI67 primary antibody (#11882 (Alexa Fluor 488 conjugate), Cell Signaling Technology) was diluted in PBS and incubated overnight at 4° C. overnight. After incubation, coverslips were washed in TBS and mounted using Prolong Gold DAPI mounting media (#P36931, Invitrogen, Carlsbad, Calif.) and sealed. TMA cores were classified based on the number of KI67 positive nuclei per core.

Generation of Recombinant Versikine.

Recombinant versikine was purified from mammalian cells and endotoxin-tested as previously described (15).

Bone Marrow Harvesting, flt3L-Mobilized Cultures and Flow Cytometry.

Bone marrow (BM) cells were harvested from C57BL/6J mice under IACUC-approved protocol M005476. Total BM cells were cultured for 9 days in the presence of 200 ng/mL flt3L, as previously described (19) with the addition of 1 mM recombinant versikine or vehicle at the beginning of culture. Harvested cells were resuspended in FACS buffer (PBS pH7.4, 2 mM EDTA, 0.5% BSA). Cell viability was established by Trypan Blue exclusion and $2 \times 10^6$ live cells were stained the following antibodies: anti-CD11c (N418-PE-Cy7, Tonbo); anti-CD103 (2E7-PE, Biolegend); anti-MHCII (M5/114.152-AlexaFluor 700, Biolegend), anti-SiglecH (551-PerCP-Cy5.5, Biolegend); anti-CD11b (P84-FITC, Biolegend) for 30 minutes on 4° C. Cells were washed and analyzed on a BD LSR II instrument-viability was assessed by DAPI staining. The instrument was calibrated daily according to manufacturer's protocol using the BD FACSDiva (v.6) Cytometer Setting & Tracking software application. Flow cytometry data was analyzed by FlowJo version 9.7.6 software (Tree Star, Ashland, Oreg.).

Immunoblot Analysis.

Whole cell lysates were prepared by boiling cells in Laemmli Sample buffer (Bio-Rad) supplemented with 100 mM DTT for 10 minutes at a final concentration of $10^7$ cells/ml. $10^5$ cells or 20 μg protein was resolved by SDS-PAGE and transferred to Immobilon-P PVDF membrane (Millipore). Membranes were blocked in 5% Milk in TBS-T [25 mM Tris-HCl (pH 7.4), 0.13M NaCl, 2.7 mM KCl]. Primary antibodies [anti-IRF8 (Cell Signaling Technologies, D20D8), anti-Batf3 (LSBio, B12B125)] were diluted in 5% Milk-TBST and membranes were incubated overnight at 4° C. Secondary antibody-HRP-conjugates as well as anti-GAPDH-HRP conjugate (Genscript A00192) incubations were carried out for 1 hour at room temperature. Signal detection was achieved using Amersham ECL Plus chemiluminescent solution (GE Healthcare). Blots were developed on Classic Blue Autoradiography Flim BX (MidSci).

Statistical Analyses.

Descriptive statistics were utilized to present the data including mean+standard deviation. Wilcoxon rank sum and chi-square analyses were utilized where noted. A p-value of <0.05 is considered statistically significant.

Results

VCAN Accumulation and Proteolysis in Normal and Malignant Colorectal Tissue.

Figure 6:
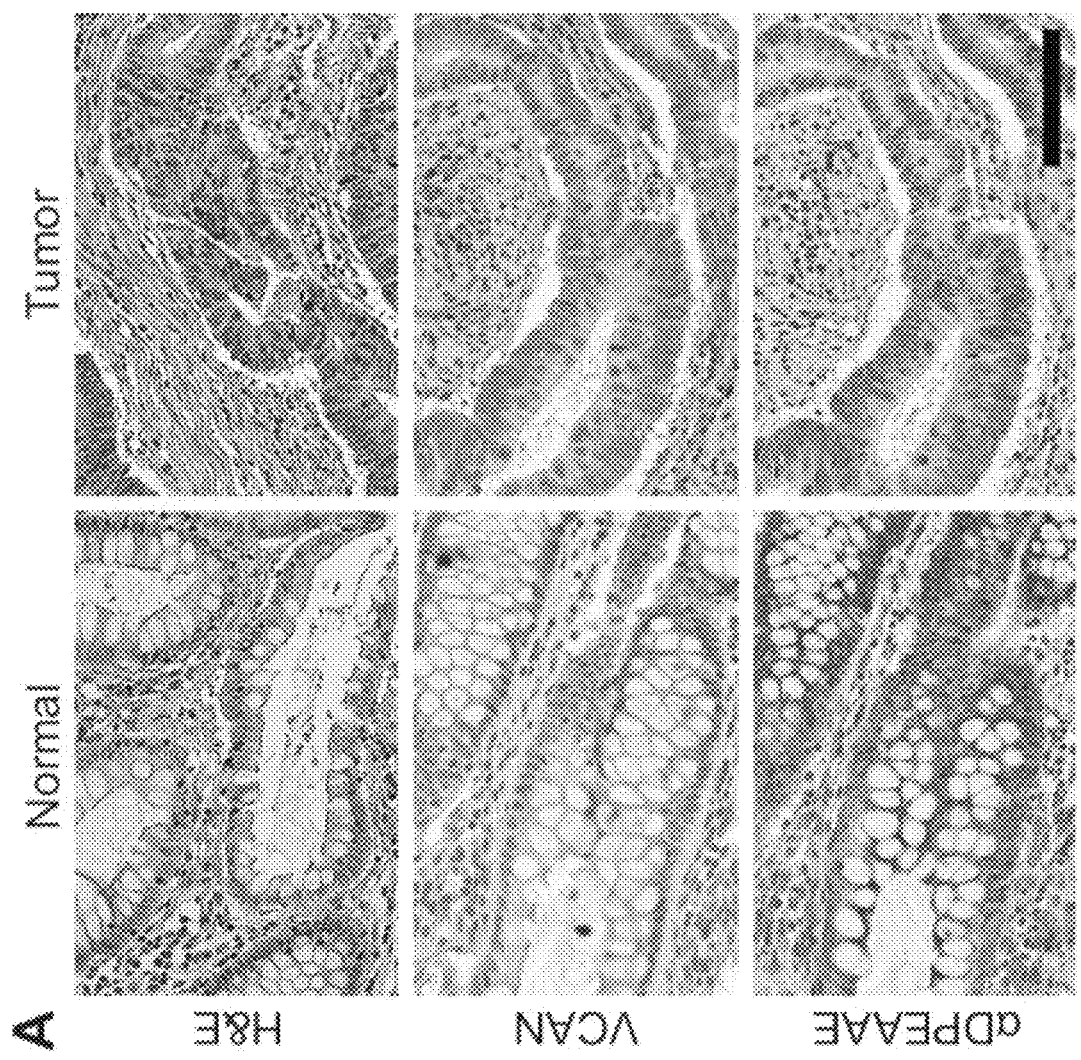
Figure 6:
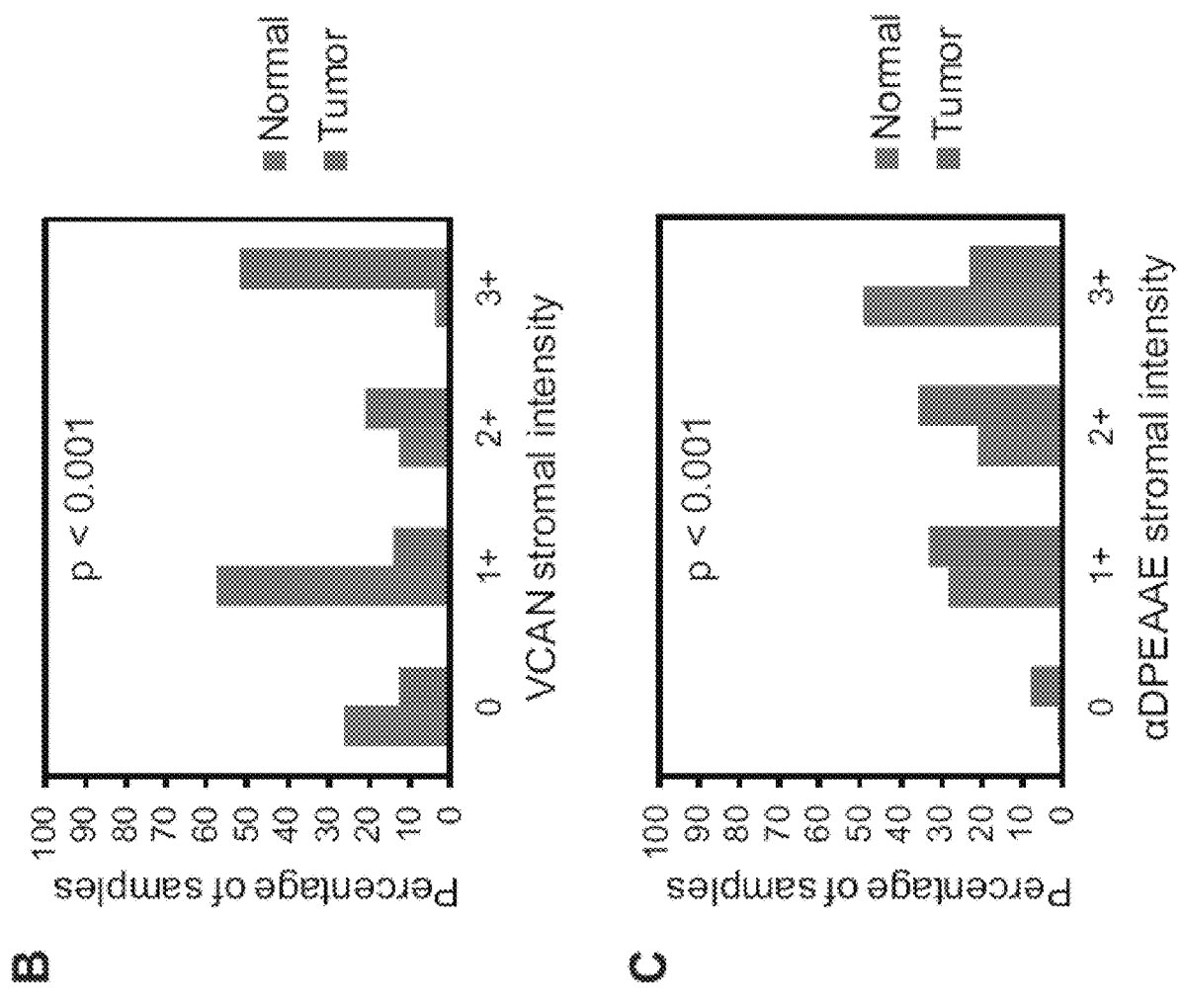

The University of Wisconsin CRC TMA consists of 122 cases with matched cores from colorectal cancer and tumor-associated normal colon tissues. We stained the TMA with antibodies raised against a neoepitope (αDPEAAE) generated through VCAN cleavage at the $Glu^{441}$-$Ala^{442}$ bond of the V1-VCAN isoform (16). DPEAAE constitutes the C-terminal end of the bioactive VCAN fragment, versikine. Serial tissue TMA sections were stained with an antibody recognizing the immunoglobulin-like domain at VCAN's N-terminal end. The latter would be expected to recognize all intact VCAN isoforms (total VCAN). Although its immunogen sequences are also included within cleaved VCAN, detection of cleaved/mobilized VCAN appears far less sensitive with the latter antibody. Intense total VCAN staining was observed in tumor stroma (FIGS. 6A and 6B). By contrast, highest intensity staining for the αDPEAAE neoepitope (2+, 3+) was detected within normal stroma and only variably within tumor stroma (Chi-square test, p<0.001; FIGS. 6A and 6C; FIG. 10).

There was no correlation between total VCAN staining and location of primary tumor (left/right colon, rectum) (FIG. 11). Increased αDPEAAE staining was observed in the rectum compared to the colon (Chi-square test, p=0.009). To determine whether VCAN processing correlated with tumor location, tumors were classified according to the degree of VCAN accumulation and processing in their stroma. Tumors were classified as "VCAN proteolysis-predominant" if their staining for total VCAN staining intensity was ≤1+ and staining for VCAN proteolysis (αDPEAAE antibody) was ≥2. Conversely, tumors were classified as "proteolysis-weak" if intact VCAN staining intensity was >1+ or αDPEAAE intensity was <2+. Despite a greater staining for αDPEAAE neoepitope being identified within the rectum, there was no significant correlation between the VCAN proteolysis-predominant classification and tumor location (Chi-square test, p=0.96; FIG. 11B).

"VCAN Proteolysis-Predominant" Tumors Show Robust CD8+ T-Cell Infiltration.

Given the immunosuppressive properties of VCAN and immunostimulatory properties of its proteolytic product, versikine (15), we hypothesized that VCAN proteolysis-predominant tumors are primed for immune infiltration. To determine whether VCAN processing correlated with CD8+ T-cell infiltration, the TMA was stained for the effector T-cell marker, CD8, and correlated with the VCAN proteolysis classification. We detected a statistically significant correlation between proteolysis-predominant status and CD8+ T-cell infiltration. CD8+ scores in "proteolysis-predominant" tumors were on average 10-fold higher than "proteolysis-weak" tumors (mean of 22 CD8+ T-cells per HPF versus 2, respectively; Wilcoxon rank sum test, p<0.001; FIG. 7A-B).

CD8+ T-cell infiltration was highest in tumors that displayed intense VCAN proteolysis together with low amounts of total VCAN (FIG. 7C). This finding suggests that low VCAN accumulation may not adequately promote T-cell infiltration unless VCAN is actively processed to generate proteolytic fragments. This observation is consistent with our hypothesis that VCAN proteolysis generates bioactive fragments with novel activities. Conversely, in tumors with high total VCAN, CD8+ T-cell infiltration may be impeded through an unfavorable stoichiometry between intact VCAN and VCAN fragments. In summary, these data suggest that VCAN proteolytic fragments are not mere markers of VCAN turnover but are endowed with important novel immunomodulatory activities. We have previously elucidated the immunoregulatory role of the VCAN fragment, versikine (15).

Since tumors with greater degrees of CD8+ T-cell infiltration are known to result in a better prognosis, the association between VCAN proteolysis and tumor stage was assessed. A trend toward an increased prevalence of staining for the VCAN proteolysis-predominant classification was seen in colon cancers of earlier stage, albeit not statistically significant (Chi-square test, p=0.28; FIG. 11C).

CD8+ T-Cell Infiltration Correlates with VCAN Proteolysis Regardless of MMR Status.

dMMR is observed in 15% of localized CRCs and 3-4% of metastatic cases (2, 4, 5). MLH1 and MSH2 are the most commonly lost MMR proteins. These proteins can be lost secondary to somatic or germline mutations or epigenetic silencing. dMMR status has been associated with an improved prognosis and increased response to immune checkpoint blockade (2, 4, 5). Since dMMR is one of the strongest predictors of CD8+ T-cell infiltration, we next examined the potential for a correlation between VCAN proteolysis and MMR status. IHC staining for the MMR proteins MLH1, MSH2, PMS2 and MSH6 was performed to determine MMR status. Consistent with prior reports, CD8+ T-cell infiltration was increased in dMMR tumors (Wilcoxon rank sum test, p<0.001; FIG. 8A). MMR status was then correlated with VCAN and αDPEAAE staining. We observed all potential staining combinations in both pMMR and dMMR cancers (FIG. 8B). A trend towards increased intensity of VCAN staining in pMMR cancers was observed. No significant differences were observed in the proportions of tumors staining for VCAN and αDPEAAE across dMMR cancers (FIG. 8B). The correlation between VCAN proteolysis and CD8+ T-cell infiltration was maintained in both pMMR and dMMR (FIG. 8C). In both pMMR and dMMR, those tumors staining for the VCAN proteolysis-predominant classification had the greatest degree of CD8+ T-cell infiltration (Wilcoxon rank sum tests: pMMR p=0.006; dMMR p=0.03). Among the VCAN proteolysis-predominant tumors there was a greater degree of CD8+ T cell infiltration in the dMMR cancers compared to pMMR cancers (35 versus 14.8 TILs per HPF, Wilcoxon rank sum test, p=0.04).

The VCAN Proteolysis Predominant Phenotype is More Common in dMMR Cancers.

Since the VCAN proteolysis predominant phenotype predicts CD8+ T-cell infiltration in both dMMR and pMMR cancers the prevalence of this phenotype was examined. Of the dMMR tumor samples, 25% possessed the VCAN proteolysis predominant phenotype, while this was observed in only 10% of pMMR samples (FIG. 3D, Wilcoxon rank sum test, p=0.01). In addition, another 25% of dMMR cancers demonstrated 1+ or less staining for both total VCAN and αDPEAAE, while this was observed in an additional 14% of pMMR cancers.

CD8+ T-Cell Exclusion is Associated with WNT Pathway Activation in Tumor Cells.

In a recent report by the Gajewski group (20), WNT signaling activation in melanoma tumor cells correlated with CD8 T-cell exclusion. Because activation of WNT signaling is a frequent molecular event in CRC secondary to the presence of truncating mutations in APC or activation mutations in CTNNB1 (21), we investigated whether analogous mechanisms operated in CRC. Indeed, we detected a statistically significant negative correlation between nuclear CTNNB1 (β-catenin, a marker of active WNT signaling) and CD8+ T-cell infiltration in CRC (Wilcoxon rank sum test, p=0.014; FIG. 8E). In addition, VCAN accumulation correlated with the presence of nuclear β-catenin (Chi-square test, p<0.001, FIG. 8F) and was more common in the pMMR cancers (8 vs. 53%, respectively, Chi-square test, p<0.001, FIG. 8G).

VCAN Accumulation and/or Proteolysis is not Associated with Tumor-Intrinsic Activation of the MAPK and PI3K Pathways, Nor with KI67 Index in CRC.

We investigated a potential correlation between MAPK pathway activation in tumor cells (detected through ERK1/2 phosphorylation), PI3K pathway activation (detected through RPS6 phosphorylation) or tumor cell proliferation (as measured through KI67 staining). The results are shown in FIGS. 12 and 13. There was no correlation between activation of these key oncogenic pathways and/or KI67 index with VCAN processing.

Versikine Promotes the Generation of CD103+ cDC from flt3L-Mobilized Primary Bone Marrow Cultures.

Versican proteolysis may impact on tumor immune contexture through regulation of intact versican bioavailability and/or the generation of novel bioactive fragments. We have previously shown that versikine, a fragment generated through versican proteolysis at the $Glu^{440}$-$Ala^{441}$ bond, activates an IRF8-dependent transcriptional program in cultured myeloid cells (15). IRF8 is a terminal selector for CD8a/CD103+ cDC (22), a DC subset with crucial roles in T-cell-mediated immunosurveillance (20, 23, 24).

Flt3L-mobilized BM cultures have long provided a faithful ex vivo model of DC differentiation (19). Addition of recombinant versikine at the onset of culture (together with flt3L) consistently and reproducibly promoted expansion of the CD103+CD11c+MHCII$^{hi}$ DC subset at both early and late culture timepoints (FIG. 9A/B). These cells were SIR-Pα$^{lo}$, CD11b$^{lo-int}$ and SiglecH$^{lo}$ confirming their identity as CD103+ conventional DC (cDC). There was no difference in the prevalence of SiglecH$^{hi}$ cells at Day 4 (data not shown). Versikine-treated cultures displayed increased expression of Irf8 and Batf3, both essential transcription factors for cDC1 development (FIG. 9C). By contrast, addition of the TLR2/6 ligand, FSL-1 (Pam2CGDPKHPKSF) conferred a disadvantage to CD103+DC development (FIG. 9D). Because intact VCAN is thought to act through TLR2/6 heterodimers (13), these results suggest that versikine may signal through pathways other than those triggered by intact VCAN. Taken together, our data suggest that tumor-seeding, bone-marrow-derived DC precursors may preferentially develop into immunogenic CD103+ DC in tumor microenvironments undergoing active VCAN proteolysis.

Discussion

Colorectal cancer remains a challenging problem of public health proportions. Recent advances in immunotherapy of solid tumors previously thought to be non-immunogenic, such as lung cancer, raised hopes that CRC patients might also benefit. However, CRC responses to novel immunotherapy modalities have been modest at best, with the exception of a small number of patients with mismatch repair-deficient CRC. Future challenges include the selection of patients most likely to respond (through the identification and validation of novel predictive biomarkers) as well as the devising and testing of innovative combinatorial immunotherapy regimens that augment efficacy with acceptable toxicity. CD8+ T-cell infiltration has been associated with an improved prognosis and response to immune checkpoint blockade, especially in the setting of dMMR. However, the mechanisms regulating immune cell infiltration are largely yet to be determined.

We report here the strong association between VCAN proteolysis and CD8+ T-cell infiltration. At a mechanistic level, proteolysis of intact VCAN can be postulated to produce three alternative consequences, not mutually exclusive: Firstly, proteolysis may regulate the amount and bioavailability of tolerogenic intact VCAN at the tumor site and the resultant degree of DC dysfunction (14). Secondly, proteolysis may disrupt VCAN's complex interactions with other immunoregulatory matrix components, such as hyaluronan or tenascin C (25). Thirdly, VCAN proteolysis generates fragments with novel activities. We recently showed that versikine, a bioactive fragment generated through VCAN proteolysis, elicits an IRF8-dependent type-I interferon transcriptional program as well as IL12 but not IL10 production from myeloid cells (15). These actions are predicted to enhance immunogenicity and tumor "sensing" by the immune system. Indeed, in a small myeloma panel, VCAN proteolysis was necessary, albeit not sufficient, for CD8+ T-cell infiltration (15). In this manuscript we demonstrate that versikine promotes generation of CD103+ CD11c$^{hi}$MHCII$^{hi}$ conventional DC from flt3L-mobilized BM progenitors. The data support a model in which DC precursors seeding tumor sites undergoing active versican proteolysis may preferentially differentiate towards CD103+ DC implicated in T-cell mediated immunosurveillance and response to immunotherapies (20, 23, 24).

We observed intense VCAN proteolysis in normal colonic epithelium. The colon constitutes an immunologically active microenvironment that has evolved to cope with the continuous exposure to exogenous antigens provided by food processing as well as intestinal microbiota. The implications of this regulation are profound and bear significance well beyond the confines of the gastrointestinal tract. Importantly, a correlation between the composition of intestinal flora and degree of response to anti-tumor immunotherapy is established and beginning to be clinically exploited (26-28). The mechanisms accounting for the regulation and "fine-tuning" of immune responses in normal colonic epithelium are poorly understood (29). It is tempting to associate VCAN processing, and the resultant generation of bioactive immunoregulatory fragments, with homeostatic DC maturation in normal colon. Because the effects of intestinal microbiota on anti-tumor immunity are thought to be regulated at the level of DCs, we hypothesize that VCAN proteolysis may collaborate with the microbiome to influence immune priming against distally-located tumors. Alternatively or additionally, versican proteolysis may specifically shape the immunological milieu of the normal epithelium located adjacent to the "expanding rim" of colonic cancers.

Moreover, VCAN accumulation and turnover may impact on the local immunoregulation of several types of solid tumors that arise in normally "sterile" sites. For example, in prostate tissue, immunosuppressive signaling from TGFβ increases expression of VCAN, reduces expression of VCAN-cleaving ADAMTS proteases and enhances expression of ADAMTS metalloproteinase inhibitor, TIMP-3 (30). Interestingly, prostate cancer constitutes another common type of solid tumor that has yet to benefit from the recent advances in immunotherapy (31). It is intriguing to hypothesize that the VCAN-versikine axis may regulate immune infiltration across a wide spectrum of solid tumors.

Our data confirm and extend previous findings regarding the mechanisms regulating T-cell infiltration or exclusion from the tumor site. In particular, we confirm previous observations implicating melanoma-intrinsic WNT signaling in T-cell exclusion and extend these findings to CRC (20). Mechanistic analyses in melanoma suggested that WNT signaling acts through CCL4 to regulate tumor infiltration by Batf3-lineage DC (CD103+DC in peripheral tissues). Our data raise the testable hypothesis that WNT signaling enhances VCAN accumulation in the tumor microenvironment, potentially through the recruitment of immunosuppressive, VCAN-producing, macrophages. VCAN promotes DC dysfunction through Toll-like receptor-2 (TLR2) signaling (14). It is tempting to speculate that tumor-intrinsic WNT signaling radically remodels the myeloid immune contexture of the tumor through inhibition of immunogenic, Batf3-expressing DC together with recruitment of immunosuppressive, VCAN-producing, macrophages. We are currently testing these hypotheses.

The data presented in this manuscript suggest that VCAN processing may influence the balance between tolerogenic and immunogenic inflammation in common solid tumors. Further to our earlier work (15), corroborating evidence has lately come from different angles. A recent paper suggested a link between VCAN turnover and anti-viral T-cell responses in mice (32). We speculate the analogous mechanisms may operate during innate immune sensing of tumors (33). VCAN-producing, immunosuppressive macrophages were shown to expand post-therapy in myeloma and inhibit T-cell proliferation (34). The abundance of VCAN in CRCs is likely regulated both at the transcriptional level through WNT signaling and post-translationally, through ADAMTS proteases encoded by loci that are epigenetically regulated upon CRC progression (35). The data provide a rationale for investigating VCAN proteolysis as a novel immune biomarker in solid tumor settings. Moreover, therapeutic manipulation of the VCAN-versikine axis through targeted proteolysis of VCAN or administration of recombinant proteolytic fragment, versikine, could be clinically tested for synergy with modern immunotherapy modalities against CRC regardless of mismatch repair status.

REFERENCES

1. Marley A R, Nan H. Epidemiology of colorectal cancer. Int J Mol Epidemiol Genet 2016; 7(3):105-14.
2. Lynch D, Murphy A. The emerging role of immunotherapy in colorectal cancer. Ann Transl Med 2016; 4(16): 305.
3. Topalian S L, Hodi F S, Brahmer J R, Gettinger S N, Smith D C, McDermott D F, et al. Safety, activity, and immune correlates of anti-PD-1 antibody in cancer. N Engl J Med 2012; 366(26):2443-54.
4. Westdorp H, Fennemann F L, Weren R D, Bisseling T M, Ligtenberg M J, Figdor C G, et al. Opportunities for immunotherapy in microsatellite instable colorectal cancer. Cancer Immunol Immunother 2016; 65(10):1249-59.
5. Bupathi M, Wu C. Biomarkers for immune therapy in colorectal cancer: mismatch-repair deficiency and others. J Gastrointest Oncol 2016; 7(5):713-20.
6. Galon J, Costes A, Sanchez-Cabo F, Kirilovsky A, Mlecnik B, Lagorce-Pages C, et al. Type, density, and location of immune cells within human colorectal tumors predict clinical outcome. Science 2006; 313(5795):1960-4.
7. Hope C, Ollar S J, Heninger E, Hebron E, Jensen J L, Kim J, et al. TPL2 kinase regulates the inflammatory milieu of the myeloma niche. Blood 2014; 123(21):3305-15.
8. Du W W, Yang W, Yee A J. Roles of versican in cancer biology—tumorigenesis, progression and metastasis. Histol Histopathol 2013; 28(6):701-13.
9. Ricciardelli C, Sakko A J, Ween M P, Russell D L, Horsfall D J. The biological role and regulation of versican levels in cancer. Cancer Metastasis Rev 2009; 28(1-2):233-45.
10. Wight T N, Kang I, Merrilees M J. Versican and the control of inflammation. Matrix Biol 2014; 35:152-61.
11. Zhang Z, Miao L, Wang L Inflammation amplification by versican: the first mediator. Int J Mol Sci 2012; 13(6): 6873-82.
12. Gao D, Joshi N, Choi H, Ryu S, Hahn M, Catena R, et al. Myeloid progenitor cells in the premetastatic lung promote metastases by inducing mesenchymal to epithelial transition. Cancer Res 2012; 72(6):1384-94.

13. Kim S, Takahashi H, Lin W W, Descargues P, Grivennikov S, Kim Y, et al. Carcinoma-produced factors activate myeloid cells through TLR2 to stimulate metastasis. Nature 2009; 457(7225):102-6.
14. Tang M, Diao J, Gu H, Khatri I, Zhao J, Cattral M S. Toll-like Receptor 2 Activation Promotes Tumor Dendritic Cell Dysfunction by Regulating IL-6 and IL-10 Receptor Signaling. Cell Rep 2015; 13(12):2851-64.
15. Hope C, Foulcer S, Jagodinsky J, Chen S X, Jensen J L, Patel S, et al. Immunoregulatory roles of versican proteolysis in the myeloma microenvironment. Blood 2016; 128(5):680-5.
16. Nandadasa S, Foulcer S, Apte S S. The multiple, complex roles of versican and its proteolytic turnover by ADAMTS proteases during embryogenesis. Matrix Biol 2014; 35:34-41.
17. Wang K, Karin M. Tumor-Elicited Inflammation and Colorectal Cancer. Adv Cancer Res 2015; 128:173-96.
18. Foulcer S J, Day A J, Apte S S. Isolation and purification of versican and analysis of versican proteolysis. Methods Mol Biol 2015; 1229:587-604.
19. Brasel K, De Smedt T, Smith J L, Maliszewski C R. Generation of murine dendritic cells from flt3-ligand-supplemented bone marrow cultures. Blood 2000; 96(9):3029-39.
20. Spranger S, Bao R, Gajewski T F. Melanoma-intrinsic beta-catenin signalling prevents anti-tumour immunity. Nature 2015; 523(7559):231-5.
21. Markowitz S D, Bertagnolli M M. Molecular origins of cancer: Molecular basis of colorectal cancer. N Engl J Med 2009; 361(25):2449-60.
22. Sichien D, Scott C L, Martens L, Vanderkerken M, Van Gassen S, Plantinga M, et al. IRF8 Transcription Factor Controls Survival and Function of Terminally Differentiated Conventional and Plasmacytoid Dendritic Cells, Respectively. Immunity 2016.
23. Broz M L, Binnewies M, Boldajipour B, Nelson A E, Pollack J L, Erle D J, et al. Dissecting the tumor myeloid compartment reveals rare activating antigen-presenting cells critical for T cell immunity. Cancer Cell 2014; 26(5):638-52.
24. Salmon H, Idoyaga J, Rahman A, Leboeuf M, Remark R, Jordan S, et al. Expansion and Activation of CD103(+) Dendritic Cell Progenitors at the Tumor Site Enhances Tumor Responses to Therapeutic PD-L1 and BRAF Inhibition. Immunity 2016; 44(4):924-38.
25. Wu Y J, La Pierre D P, Wu J, Yee A J, Yang B B. The interaction of versican with its binding partners. Cell Res 2005; 15(7):483-94.
26. Pitt J M, Vetizou M, Waldschmitt N, Kroemer G, Chamaillard M, Boneca I G, et al. Fine-Tuning Cancer Immunotherapy: Optimizing the Gut Microbiome. Cancer Res 2016; 76(16):4602-7.
27. Spranger S, Sivan A, Corrales L, Gajewski T F. Tumor and Host Factors Controlling Antitumor Immunity and Efficacy of Cancer Immunotherapy. Adv Immunol 2016; 130:75-93.
28. Goldszmid R S, Dzutsev A, Viaud S, Zitvogel L, Restifo N P, Trinchieri G. Microbiota modulation of myeloid cells in cancer therapy. Cancer Immunol Res 2015; 3(2):103-9.
29. Coombes J L, Powrie F. Dendritic cells in intestinal immune regulation. Nat Rev Immunol 2008; 8(6):435-46.
30. Cross N A, Chandrasekharan S, Jokonya N, Fowles A, Hamdy F C, Buttle D J, et al. The expression and regulation of ADAMTS-1, -4, -5, -9, and -15, and TIMP-3 by TGFbeta1 in prostate cells: relevance to the accumulation of versican. Prostate 2005; 63(3):269-75.
31. Rekoske B T, McNeel D G. Immunotherapy for prostate cancer: False promises or true hope? Cancer 2016; 122 (23):3598-607.
32. McMahon M, Ye S, Izzard L, Dlugolenski D, Tripp R A, Bean A G, et al. ADAMTS5 Is a Critical Regulator of Virus-Specific T Cell Immunity. PLoS Biol 2016; 14(11): e1002580.
33. Woo S R, Corrales L, Gajewski T F. Innate immune recognition of cancer. Annu Rev Immunol 2015; 33:445-74.
34. Arana P, Zabaleta A, Lasa M, Maiso P, Alignani D, Jelinek T, et al. High-Throughput Characterization and New Insight into the Role of Tumor Associated Macrophages (TAMs) in Multiple Myeloma (MM). Blood 2016; 128(22):482-82.
35. Lind G E, Kleivi K, Meling G I, Teixeira M R, Thiis-Evensen E, Rognum T O, et al. ADAMTS1, CRABP1, and NR3C1 identified as epigenetically deregulated genes in colorectal tumorigenesis. Cell Oncol 2006; 28(5-6):259-72.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. All of the cited references are incorporated by reference herein in their entireties. In the event that there is an inconsistency between a definition of a term in the specification as compared to a definition of the term in a cited reference, the term should be interpreted based on the definition in the specification.

We claim:

1. A method for inducing and/or potentiating a T-cell mediated immune response in a subject in need thereof, the method comprising administering to the subject a pharmaceutical composition comprising an effective amount of a molecule comprising a versican fragment or variant thereof, wherein the versican fragment or variant thereof consists of the amino acid sequence of SEQ ID NO: 5, SEQ ID NO:6, or SEQ ID NO: 7; and wherein the molecule induces and/or potentiates the T-cell mediated immune response.

2. The method of claim 1, wherein the molecule does not have any chondroitin sulfate side chains.

3. The method of claim 1, wherein administering comprises injecting locally into tumor tissue of the subject the pharmaceutical composition comprising an effective amount of the molecule.

4. A method for inducing and/or potentiating a T-cell mediated immune response in a subject in need thereof, wherein the subject has a cell proliferative disease or disorder, the method comprising administering to the subject a pharmaceutical composition comprising an effective amount of a molecule comprising a versican fragment or variant thereof, wherein the versican fragment or variant thereof consists of the amino acid sequence of SEQ ID NO: 5, SEQ ID NO:6, or SEQ ID NO: 7; and wherein the molecule induces and/or potentiates the T-cell mediated immune response.

5. The method of claim 4, wherein the molecule does not have any chondroitin sulfate side chains.

6. The method of claim 4, wherein administering comprises injecting locally into tumor tissue of the subject the pharmaceutical composition comprising an effective amount of the molecule.

* * * * *